United States Patent
Itoh et al.

(10) Patent No.: US 11,427,554 B2
(45) Date of Patent: Aug. 30, 2022

(54) LACTONE COMPOUND AND NOVEL ETHER COMPOUND

(71) Applicant: TAKASAGO INTERNATIONAL CORPORATION, Tokyo (JP)

(72) Inventors: Hisanori Itoh, Kanagawa (JP); Takaji Matsumoto, Kanagawa (JP); Makoto Harada, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 52 days.

(21) Appl. No.: 17/044,080

(22) PCT Filed: Apr. 8, 2019

(86) PCT No.: PCT/JP2019/015363
§ 371 (c)(1),
(2) Date: Sep. 30, 2020

(87) PCT Pub. No.: WO2019/198678
PCT Pub. Date: Oct. 17, 2019

(65) Prior Publication Data
US 2021/0047283 A1      Feb. 18, 2021

Related U.S. Application Data

(60) Provisional application No. 62/656,054, filed on Apr. 11, 2018.

(51) Int. Cl.
*C07D 307/83*      (2006.01)
*A23L 27/20*      (2016.01)
*A61K 8/49*      (2006.01)

(52) U.S. Cl.
CPC ........ *C07D 307/83* (2013.01); *A23L 27/2052* (2016.08); *A61K 8/498* (2013.01)

(58) Field of Classification Search
CPC .... C07D 307/83; A23L 27/2052; A61K 8/498
See application file for complete search history.

(56) References Cited

U.S. PATENT DOCUMENTS

| | | | |
|---|---|---|---|
| 4,407,740 A | 10/1983 | Köspel et al. | |
| 5,464,824 A | 11/1995 | Gaudin | |
| 2002/0098271 A1 | 7/2002 | Frerot et al. | |
| 2013/0030193 A1 | 1/2013 | Yagi et al. | |
| 2013/0245286 A1 | 9/2013 | Yagi et al. | |
| 2013/0245287 A1 | 9/2013 | Yagi et al. | |

FOREIGN PATENT DOCUMENTS

| | | |
|---|---|---|
| FR | 2721926 A1 | 1/1996 |
| JP | S54-080432 A | 6/1979 |
| JP | S56-169621 A | 12/1981 |
| JP | H07-503281 A | 4/1995 |
| JP | H10-120671 A | 5/1998 |
| JP | 2003-505556 A | 2/2003 |
| JP | 2004-269463 A | 9/2004 |
| WO | 2012165164 A1 | 12/2012 |

OTHER PUBLICATIONS

STN Registry database entry for CAS RN 873378-12-2, Accessed Apr. 7, 2022, Entered STN Feb. 3, 2006.*
Y. Ito et al. "A New Approach for Stereoselective Synthesis of γ Butyrolactones" Journal of Organic Chemistry, vol. 47, 1982, (pp. 741-743).
Michael P. Doyle et al. "Chiral Catalyst Controlled Diastereoselection and Regioselection in Intramolecular Carbon-Hydrogen Insertion Reactions of Diazoacetates" Journal of the American Chemical Society, vol. 118, 1996, (8837-8846).
Caroline Plessis et al. "Novel photolactonisation from xanthenoic esters" Tetrahedron Letters, vol. 42, 2001, (pp. 6519-6522).
Christian S. Jungong et al. "Synthetically useful transformations of δ-sultones and thiane-1, 1-dioxides obtained by C—H insertion" Heterocycles, vol. 78, No. 10, 2009, (pp. 2531-2539).
K. Paranjpe et al. "Synthesis of santonin" Current Science, vol. 12, 1943, pp. 150-151 (4 pages total including the cover).
Duminda S. Liyanage et al. "Oxidative conversion of δ-sultones to γ-lactones" Tetrahedron Letters, vol. 56, 2015, (pp. 2269-2271).
International Search Report (PCT/ISA/210), issued by International Searching Authority in corresponding International Application No. PCT/JP2019/015363, dated Jul. 2, 2019.

(Continued)

*Primary Examiner* — Alicia L Otton
(74) *Attorney, Agent, or Firm* — Sughrue Mion, PLLC

(57) ABSTRACT

A lactone compound is represented by general formula (A), and an ether compound is represented by general formula (B). In formula (A), R is a hydrogen atom or R1. When R is a hydrogen atom, R' is R1, the carbon bond (1) is a single bond or a double bond, and the carbon bond (2) is a single bond. When R is R1, R' is a hydrogen atom or R1, both the carbon bonds (1) and (2) are a single bond, or one of them is a double bond and the other is a single bond. In formula (B), R" is R1. R1 represents a specific alkyl group, a specific alkenyl group, a specific alkynyl group, or an aryl group. In formulas (A) and (B), n is 0 or 1.

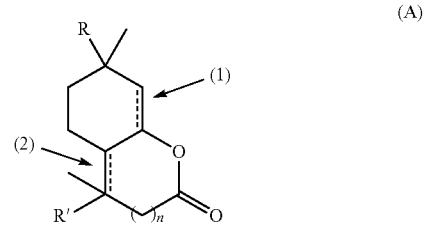

(A)

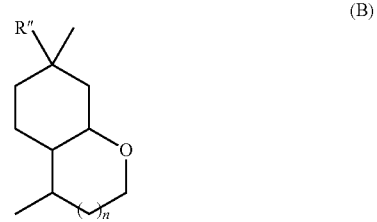

(B)

8 Claims, No Drawings

(56) References Cited

OTHER PUBLICATIONS

Written Opinion (PCT/ISA/237) issued by the International Searching Authority in corresponding International Application No. PCT/JP2019/015363, dated Jul. 2, 2019.

* cited by examiner

LACTONE COMPOUND AND NOVEL ETHER COMPOUND

CROSS-REFERENCE TO RELATED APPLICATIONS

This application is a National Stage Entry of PCT International Application No. PCT/JP2019/015363, filed on Apr. 8, 2019, which claims priority to U.S. Provisional Patent Application No. 62/656,054 filed on Apr. 11, 2018, the contents of all of which are incorporated herein by reference in their entirety.

TECHNICAL FIELD

The present invention relates to novel compounds capable of imparting novel aromas and a flavor or fragrance composition containing these compounds.

BACKGROUND ART

In the production of a flavor or fragrance, there is a wide demand for flavors or fragrances having a floral note representing the fragrance note of flowers, or flavors or fragrances having a fruity note representing the fragrance note of fruits, and in particular, peach-like and jasmine-like flavor or fragrance compounds are very useful. In the related technology, most of the peach-like and jasmine-like flavor or fragrance compounds are a lactone-based compound, and γ-nonalactone, γ-decalactone, δ-decalactone, and γ-undecalactone have been widely used as a flavor or fragrance having a peach-like aroma. In recent years, flavor or fragrance compounds such as lactones having double bonds such as Jasmine lactone (ZEON Corporation) and Jasmo lactone (Firmenich S.A.), and frutonile (Givaudan S.A.) and nectaryl (Givaudan S.A.) having a structure different from that of lactones have been developed and have been used as the peach-like and jasmine-like flavor or fragrance composition.

SUMMARY OF INVENTION

Technical Problem

However, existing compounds have fragrance notes different from the main fragrance notes, such as a coconut-like note, a fruit-like note, and a floral-like note, and it has been hard to say that a fragrance note such as a pure peach-like note or a pure jasmine-like note is reproduced. In addition, there are problems that all the flavor or fragrance compounds have problems in the persistence, an aroma is hardly felt within a few hours to a day under dilution conditions or within 1 to 2 weeks even in neat, or the original fragrance note changes to a fragrance note that is different from the original fragrance note.

In recent years, with the diversification of products such as various fragrances or cosmetics, health and hygiene materials, and pharmaceuticals, developments of flavor or fragrance substances, which have a unique odor quality, high palatability, strong retention, good stability, and high safety, have been more demanded in flavors or fragrances for the fragrances or cosmetics and the health and hygiene materials, further in flavors or fragrances for pharmaceuticals. In particular, with regard to a flavor or fragrance material having a peach-like fragrance note, a flavor or fragrance material satisfying such a requirement is insufficient, and a new flavor or fragrance material satisfying the above properties is expected to be further developed in addition to common flavor or fragrance substances.

Therefore, an object of the present invention is to provide novel compounds capable of imparting a pure peach-like or jasmine-like aroma satisfying the above requirements, and a flavor or fragrance composition containing these compounds.

Solution to Problem

As a result of intensive studies under such circumstances, the present inventors have found that bicyclic lactone-based compound and bicyclic ether-based compound are synthesized, and these compounds can have a strong peach-like aroma or jasmine-like aroma and can be a useful fragrance agent or flavoring agent. Accordingly, the present inventors have completed the present invention. Namely, the present invention includes the following [1] to [5].

[1] A lactone compound represented by the following general formula (A):

[Chem. 1]

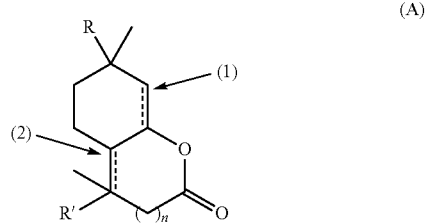

wherein R represents a hydrogen atom or R1 described below;

in the case where R represents a hydrogen atom, R' represents R1 described below, the carbon bond (1) is a single bond or a double bond, and the carbon bond (2) is a single bond;

in the case where R represents R1 described below, R' represents a hydrogen atom or R1 described below, both the carbon bonds (1) and (2) are a single bond, or one of them is a double bond and the other is a single bond;

R1 represents an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group; and n is 0 or 1.

[2] An ether compound represented by the following general formula (B):

[Chem. 2]

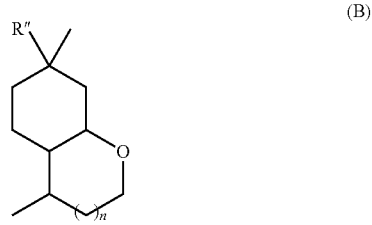

wherein R″ represents an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group; and n is 0 or 1.

[3] A flavor or fragrance composition comprising the compound according to [1] or [2].

[4] A beverage, food, fragrance or cosmetic, toiletry product, air care product, daily necessities and household goods, oral composition, hair care product, skin care product, body care product, detergent for cloth, soft finishing agent for cloth, quasi-drug, or pharmaceutical, which comprises the flavor or fragrance composition according to [3].

[5] A method for improving an aroma of a flavor or fragrance, the method comprising adding the compound according to [1] or [2] to a flavor or fragrance.

Advantageous Effects of Invention

The lactone compound and the ether compound, which are the compounds in the present invention, are a very useful flavor or fragrance material having a strong peach-like aroma or jasmine-like aroma that is pleasant and persistent. A flavor or fragrance composition having high palatability can be provided by blending the compounds in the present invention.

DESCRIPTION OF EMBODIMENTS

The present invention is described in detail below.

<Lactone Compound>

The lactone compound in the present invention is a lactone compound represented by the following general formula (A).

[Chem. 3]

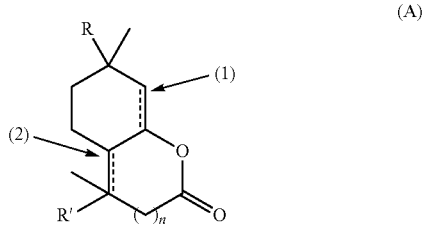

(A)

[In the above formula, R represents a hydrogen atom or R1 described below;

in the case where R represents a hydrogen atom, R' represents R1 described below, the carbon bond (1) is a single bond or a double bond, and the carbon bond (2) is a single bond;

in the case where R represents R1 described below, R' represents a hydrogen atom or R1 described below, both the carbon bonds (1) and (2) are a single bond, or one of them is a double bond and the other is a single bond;

R1 is an alkyl group having 1 to 8 carbon atoms which may have substituent(s); an alkenyl group having 2 to 8 carbon atoms which may have substituent(s); an alkynyl group having 2 to 8 carbon atoms which may have substituent(s); or an aryl group;

In the case where the carbon bond (2) is a double bond, R' is absent; and n is 0 or 1.]

R represents a hydrogen atom, an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group.

Examples of the alkyl group having 1 to 8 carbon atoms, which is represented by R, include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, and the like.

The alkyl group having 1 to 8 carbon atoms, which is represented by R, may be a cyclic alkyl, and examples thereof include a cyclopropyl group, a cyclobutyl group, a cyclopentyl group, a cyclohexyl group, a cycloheptyl group, a cyclooctyl group, and the like.

Examples of the alkenyl group having 2 to 8 carbon atoms, which is represented by R, include a vinyl group, a 1-propenyl group, a 2-propenyl group, an isopropenyl group, a 1-butenyl group, a 2-butenyl group, a 3-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a pentenyl group, a hexenyl group, a heptenyl group, an octenyl group, and the like.

The alkenyl group having 2 to 8 carbon atoms, which is represented by R, may be a cyclic alkenyl group, and examples thereof include a cyclopentenyl group, a cyclopentadienyl group, a cyclohexenyl group, a cyclohexadienyl group, a cycloheptenyl group, a cycloheptadienyl group, a cyclooctenyl group, a cyclooctadienyl group, and the like.

Examples of the alkynyl group having 2 to 8 carbon atoms, which is represented by R, include an ethynyl group, a 1-propargyl group, a 1-butynyl group, a 2-butynyl group, a 2-pentyl group, a 3-hexynyl group, a 1-heptynyl group, a 2-octynyl group, and the like.

Examples of the substituent(s) which may be contained by R include an alkyl group having 1 to 6 carbon atoms, such as a methyl group, an ethyl group, an n-propyl group, an isopropyl group, an n-butyl group, an isobutyl group, a sec-butyl group, a tert-butyl group, a pentyl group, and a hexyl group, an alkoxy group having 1 to 4 carbon atoms, such as a methoxy group, an ethoxy group, an n-propoxy group, an isopropoxy group, an n-butoxy group, an isobutoxy group, a sec-butoxy group, a tert-butoxy group, and a methylenedioxy group, and the like.

R' represents a hydrogen atom, an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group.

Examples of the alkyl group having 1 to 8 carbon atoms, which is represented by R', include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, and the like.

The alkyl group having 1 to 8 carbon atoms, which is represented by R', may be a cyclic alkyl, and examples thereof include a cyclopropyl group, a cyclobutyl group, a cyclopentyl group, a cyclohexyl group, a cycloheptyl group, a cyclooctyl group, and the like.

Examples of the alkenyl group having 2 to 8 carbon atoms, which is represented by R', include a vinyl group, a 1-propenyl group, a 2-propenyl group, an isopropenyl group, a 1-butenyl group, a 2-butenyl group, a 3-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a pentenyl group, a hexenyl group, a heptenyl group, an octenyl group, and the like.

Examples of the alkynyl group having 2 to 8 carbon atoms, which is represented by R', include an ethynyl group, a 1-propargyl group, a 1-butynyl group, a 2-butynyl group, a 2-pentyl group, a 3-hexynyl group, a 1-heptynyl group, a 2-octynyl group, and the like.

The alkenyl group having 2 to 8 carbon atoms, which is represented by R', may be a cyclic alkenyl group, and examples thereof include a cyclopentenyl group, a cyclopentadienyl group, a cyclohexenyl group, a cyclohexadienyl group, a cycloheptenyl group, a cycloheptadienyl group, a cyclooctenyl group, a cyclooctadienyl group, and the like.

Examples of the substituent(s) which may be contained by R' include an alkyl group having 1 to 6 carbon atoms, such as a methyl group, an ethyl group, an n-propyl group, an isopropyl group, an n-butyl group, an isobutyl group, a sec-butyl group, a tert-butyl group, a pentyl group, and a hexyl group, an alkoxy group having 1 to 4 carbon atoms, such as a methoxy group, an ethoxy group, an n-propoxy group, an isopropoxy group, an n-butoxy group, an isobutoxy group, a sec-butoxy group, a tert-butoxy group, and a methylenedioxy group, and the like.

In the formula (A), R may be a hydrogen atom only in the case where the carbon bond (2) is a single bond, and R' is not a hydrogen atom.

Namely, in the formula (A), both the case where the carbon bond (1) is a single bond or a double bond, the carbon bond (2) is a single bond, and R and R' represent a hydrogen atom, and the case where the carbon bond (1) is a single bond, the carbon bond (2) is a double bond, R represents a hydrogen atom, and R' is R1 described above are excluded.

<Ether Compound>

The ether compound in the present invention is an ether compound represented by the following general formula (B).

[Chem. 4]

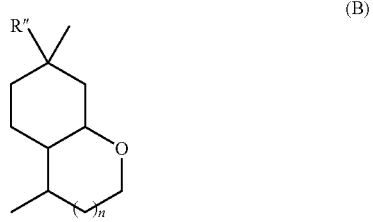

(B)

[In the above formula, R" represents an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group; and n is 0 or 1.]

Examples of the alkyl group having 1 to 8 carbon atoms, which is represented by R", include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, and the like.

The alkyl group having 1 to 8 carbon atoms, which is represented by R", may be a cyclic alkyl, and examples thereof include a cyclopropyl group, a cyclobutyl group, a cyclopentyl group, a cyclohexyl group, a cycloheptyl group, a cyclooctyl group, and the like.

Examples of the alkenyl group having 2 to 8 carbon atoms, which is represented by R", include a vinyl group, a 1-propenyl group, a 2-propenyl group, an isopropenyl group, a 1-butenyl group, a 2-butenyl group, a 3-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a pentenyl group, a hexenyl group, a heptenyl group, an octenyl group, and the like.

The alkenyl group having 2 to 8 carbon atoms, which is represented by R", may be a cyclic alkenyl group, and examples thereof include a cyclopentenyl group, a cyclopentadienyl group, a cyclohexenyl group, a cyclohexadienyl group, a cycloheptenyl group, a cycloheptadienyl group, a cyclooctenyl group, a cyclooctadienyl group, and the like.

Examples of the alkynyl group having 2 to 8 carbon atoms, which is represented by R", include an ethynyl group, a 1-propargyl group, a 1-butynyl group, a 2-butynyl group, a 2-pentyl group, a 3-hexynyl group, a 1-heptynyl group, a 2-octynyl group, and the like.

Examples of the substituent(s) which may be contained by R" include an alkyl group having 1 to 6 carbon atoms, such as a methyl group, an ethyl group, an n-propyl group, an isopropyl group, an n-butyl group, an isobutyl group, a sec-butyl group, a tert-butyl group, a pentyl group, and a hexyl group, an alkoxy group having 1 to 4 carbon atoms, such as a methoxy group, an ethoxy group, an n-propoxy group, an isopropoxy group, an n-butoxy group, an isobutoxy group, a sec-butoxy group, a tert-butoxy group, and a methylenedioxy group, and the like.

Preferred specific examples of the lactone compound represented by the general formula (A) and the ether compound represented by the general formula (B) in the present invention include, but are not limited to, the compounds shown below.

[Chem. 5]

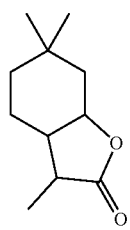

Me-1

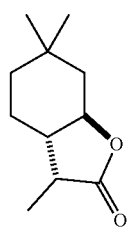

Me-1a

Me-1b
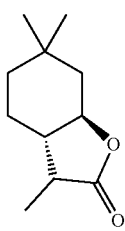
Me-1c
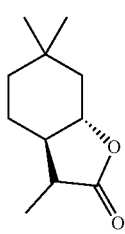
Me-2
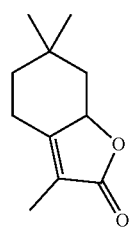
Me-3
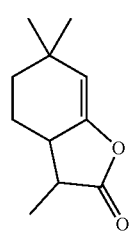
Me-4
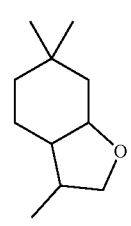
Me-5
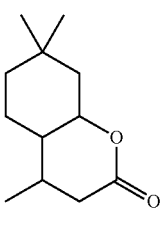
Me-6
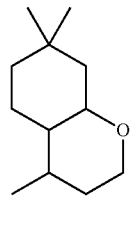
Me-7
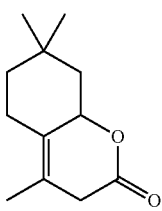
Et-1
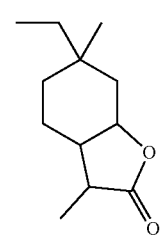
Et-1a
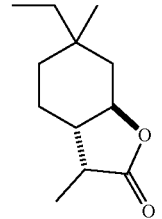
Et-2
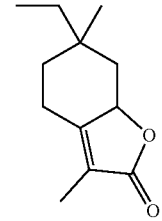
Et-3
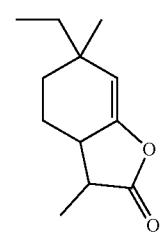
Et-4
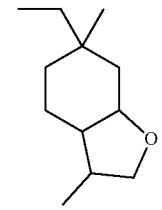
Et-5
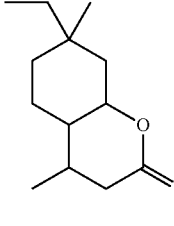

-continued
Et-6 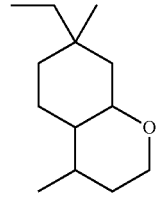
Pr-1 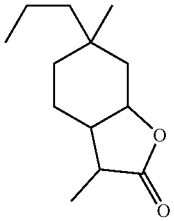
Pr-1a 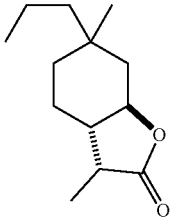
Pr-2 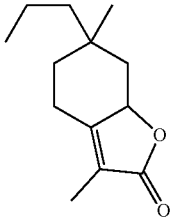
Pr-3 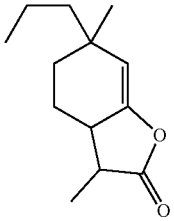
Pr-4 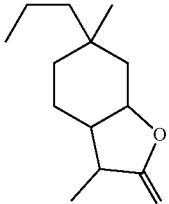
Pr-5 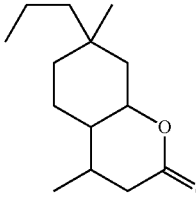
-continued
Pr-6 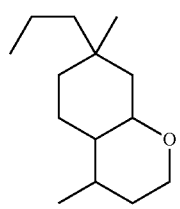
iPr-1 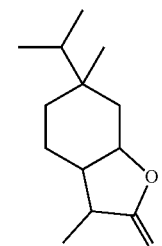
iPr-1a 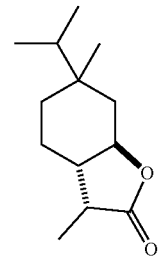
iPr-2 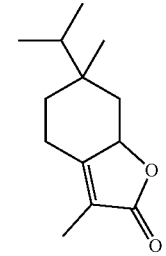
iPr-3 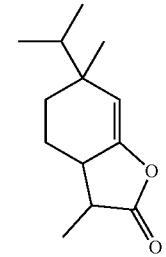
iPr-4 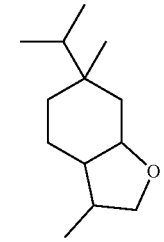

iPr-5
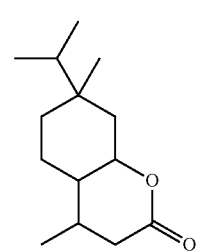
iPr-6
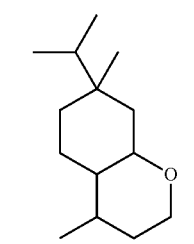
Bu-1
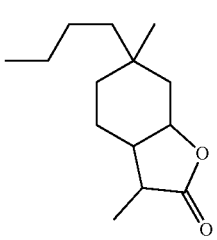
Bu-1a
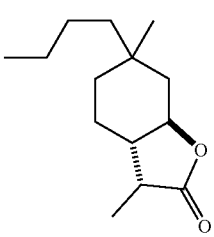
Bu-1aa
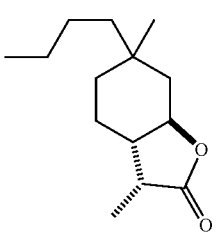
Bu-1ab
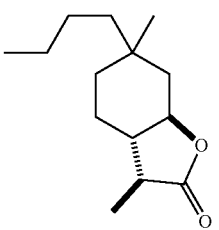
Bu-1ac
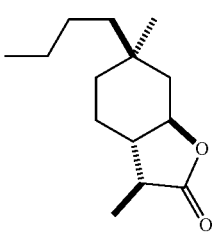
Bu-1ad
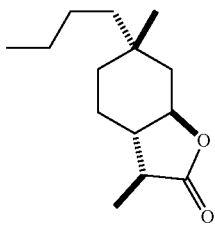
Bu-1ae
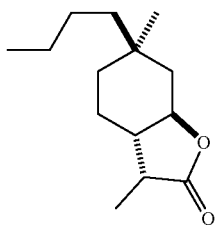
Bu-1af
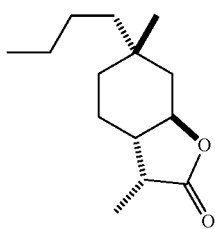
Bu-1ba
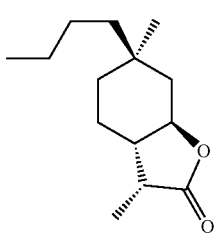
Bu-1bb
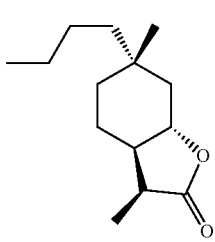
Bu-1bc
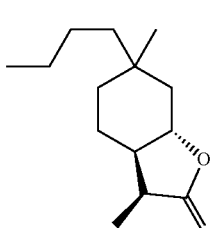
Bu-1bd
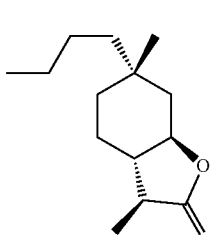

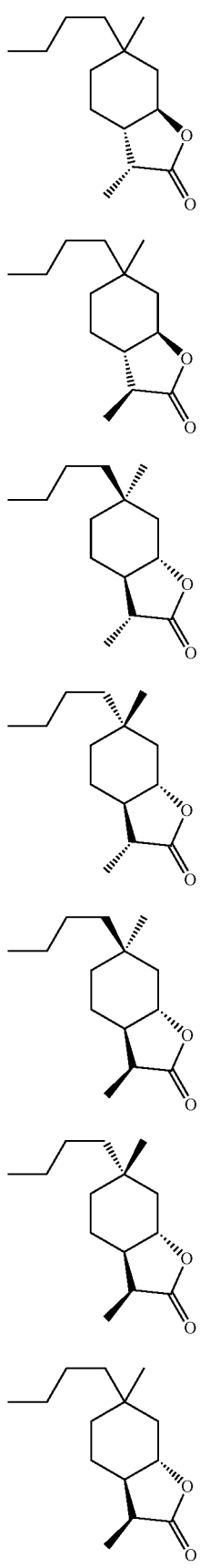
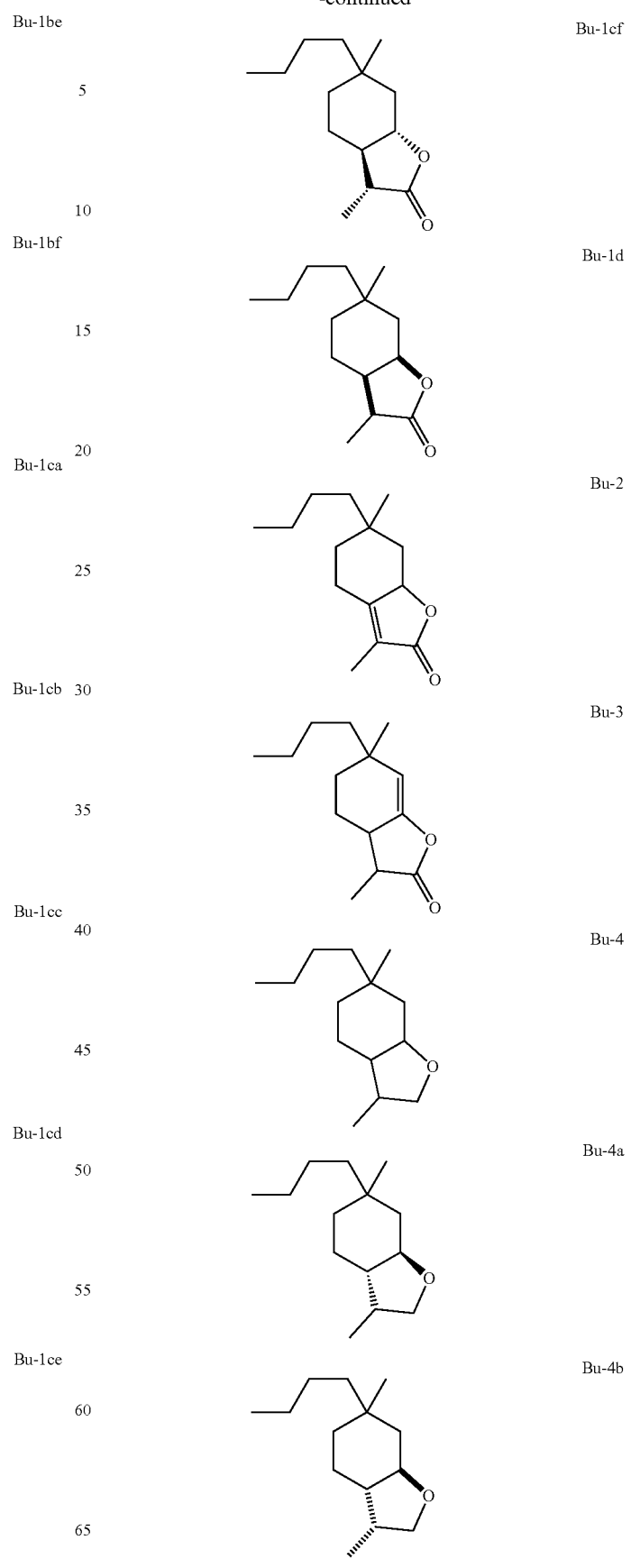

-continued
Bu-4c
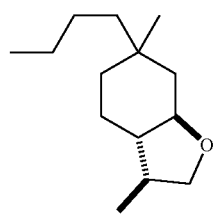
Bu-5
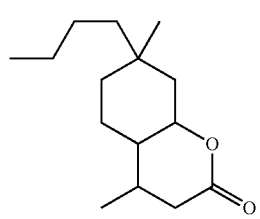
Bu-5a
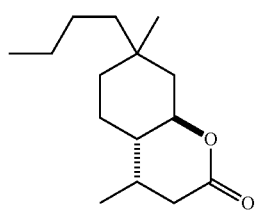
Bu-6
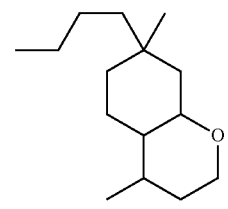
[Chem. 6]
iBu-1
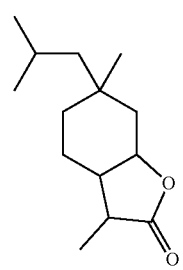
iBu-1a
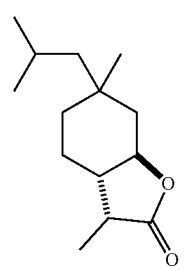
-continued
iBu-2
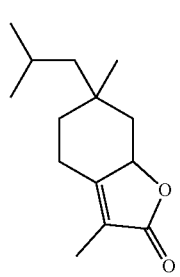
iBu-3
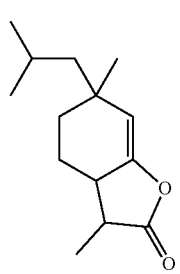
iBu-4
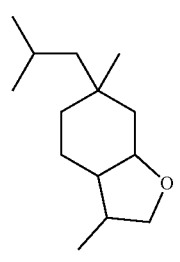
iBu-4a
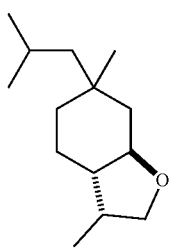
iBu-5
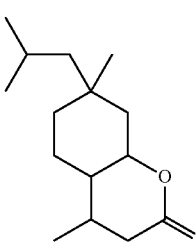
iBu-6
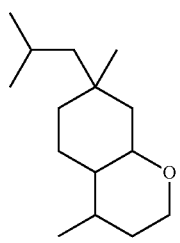

sBu-1
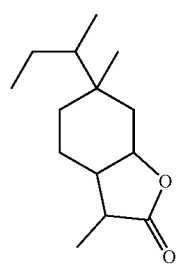
sBu-1a
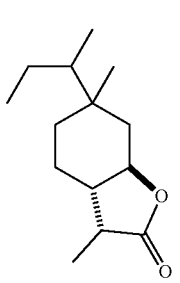
sBu-2
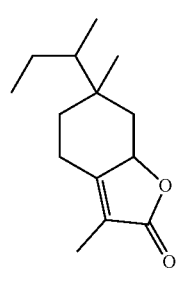
sBu-3
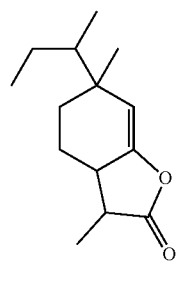
sBu-4
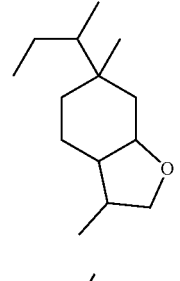
sBu-4a
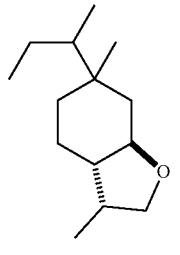
sBu-5
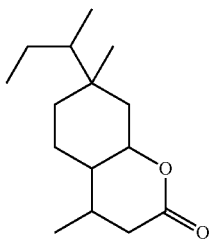
sBu-6
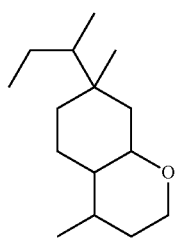
Pe-1
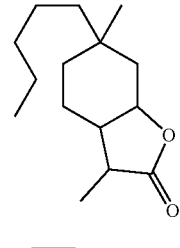
Pe-1a
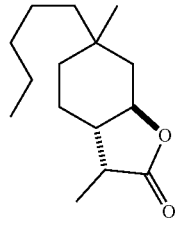
Pe-2
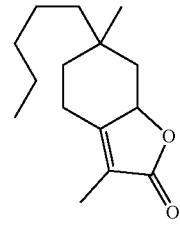
Pe-3
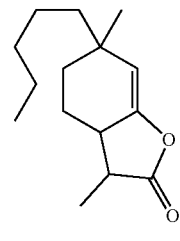
Pe-4
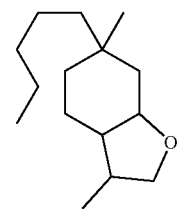

Pe-4a
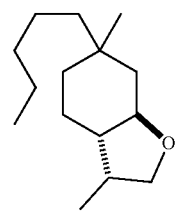
Pe-5
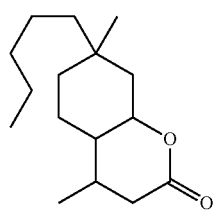
Pe-6
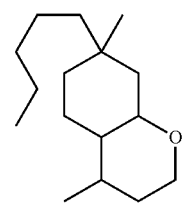
3Pe-1
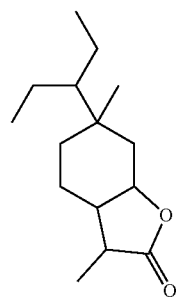
3Pe-1a
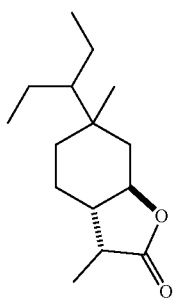
3Pe-2
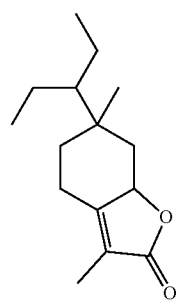
3Pe-3
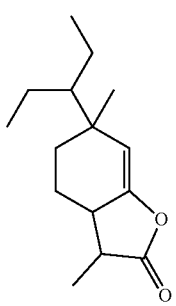
3Pe-4
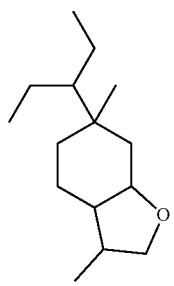
3Pe-4a
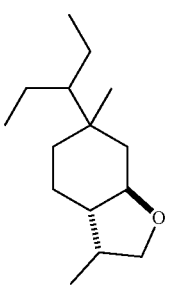
3Pe-5
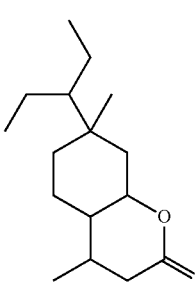
3Pe-6
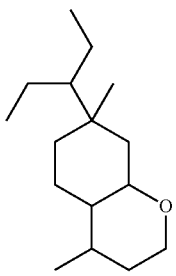

-continued
Hx-1
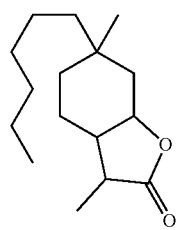
Hx-1a
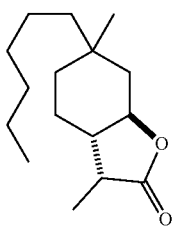
Hx-2
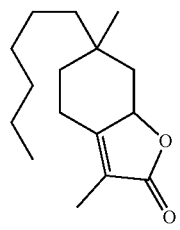
Hx-3
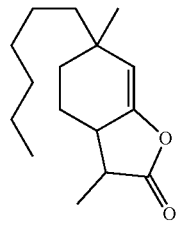
Hx-4
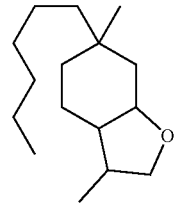
Hx-4a
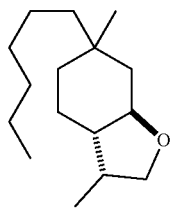
Hx-5
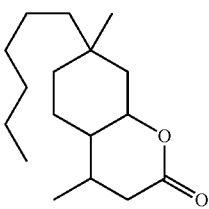
-continued
Hx-6
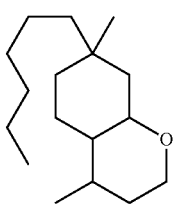
Hp-1
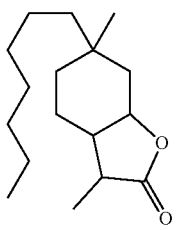
Hp-1a
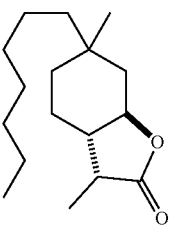
Hp-2
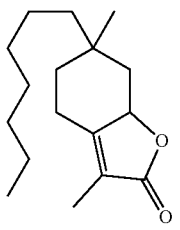
Hp-3
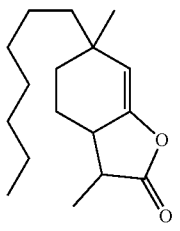
Hp-4
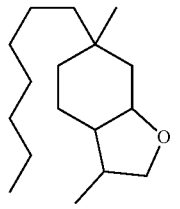
Hp-4a
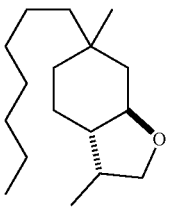

Hp-5
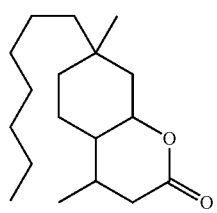
Hp-6
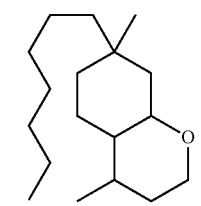
Oc-1
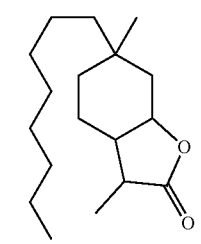
Oc-1a
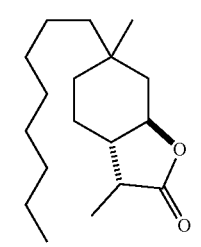
Oc-2
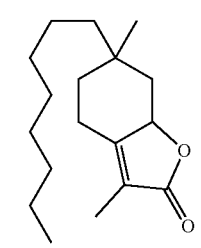
Oc-3
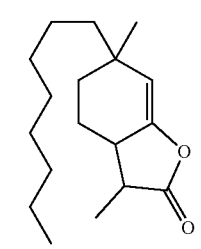
Oc-4
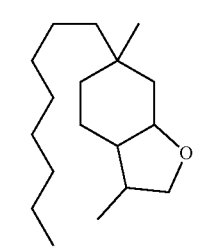
Oc-4a
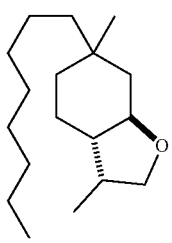
Oc-5
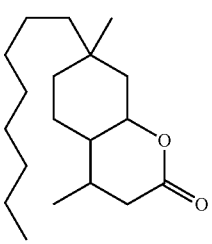
Oc-6
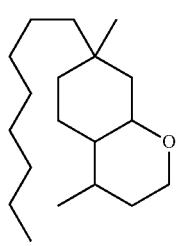
Ph-1
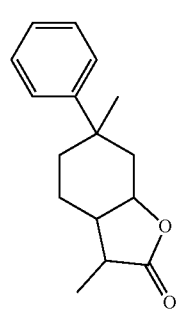
Ph-1a
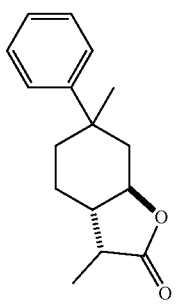
Ph-2
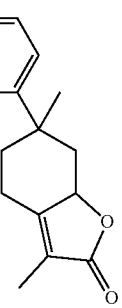

-continued
Ph-3
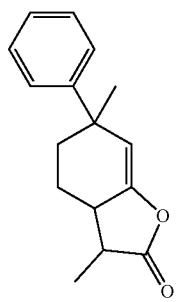
Ph-4
Ph-4a
Ph-5
Ph-6
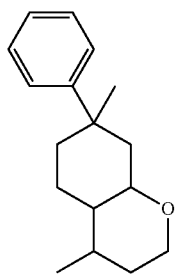
[Chem. 7]
-continued
Cy-1
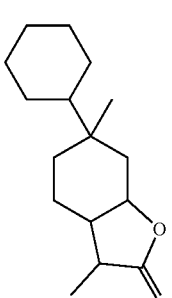
Cy-1a
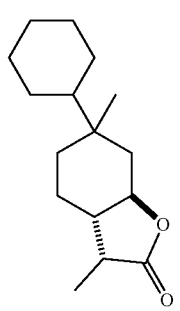
Cy-2
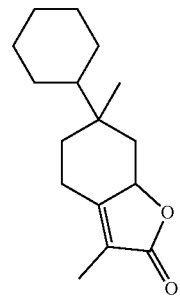
Cy-3
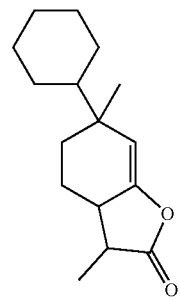
Cy-4
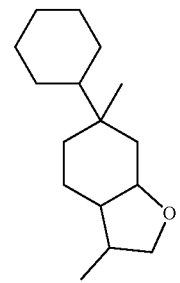

| | |
|---|---|
| Cy-4a | N-1-Ph |
| Cy-5 | Me-1-Me |
| Cy-6 | Me-1-Ay |
| N-1-Me | Me-1-Bu |
| N-1-Ay | Me-1-Ph |
| N-1-Bu | Bu-1-Me |

-continued
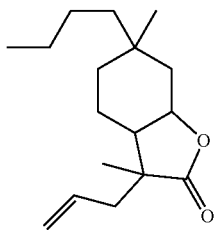 Bu-1-Ay
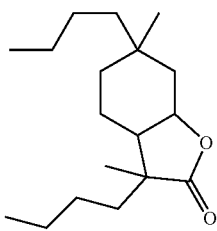 Bu-1-Bu
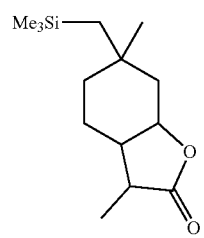 Me-6
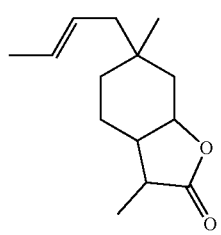 Bu-7
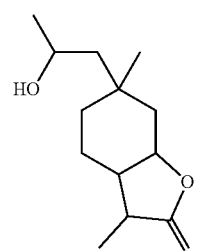 Pr-7
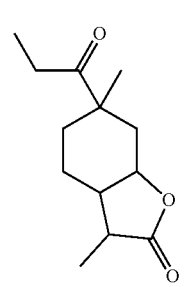 Pr-8
-continued
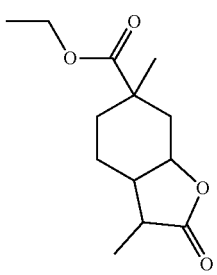 Me-9
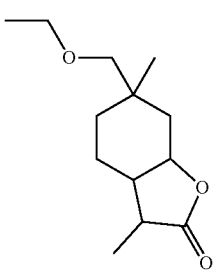 Me-10
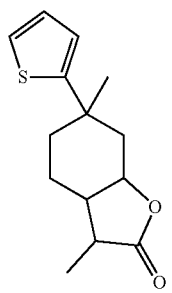 TP-1
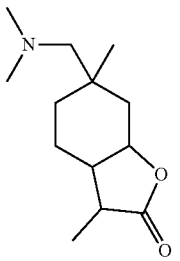 Me-11
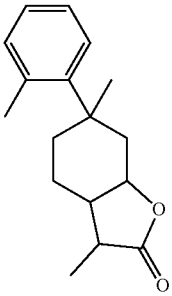 TL-1

Py-1
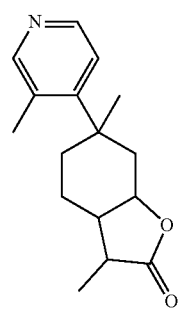
Et-7
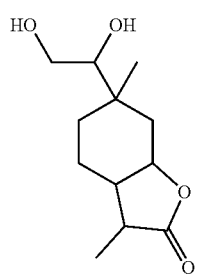
CyPr-1
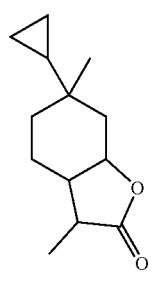
tBu-1
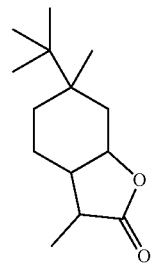
CyBu-1
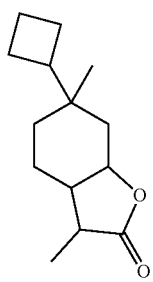
Me-12
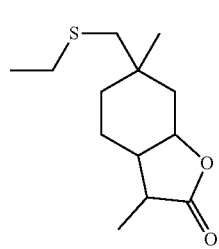
Me-13
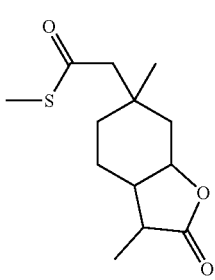
Me-14
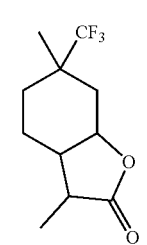
Me-15
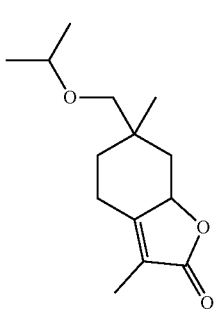
FL-1
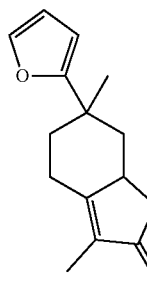
Me-16

-continued
PN-1
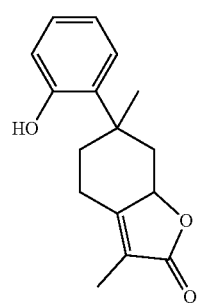
tBu-2
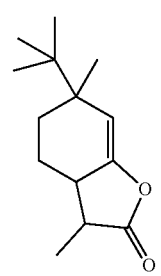
iBu-7-Me
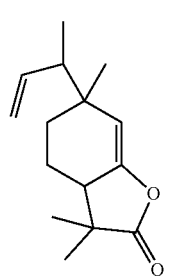
Pr-7
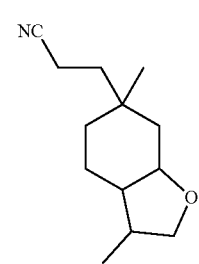
CyPr-2
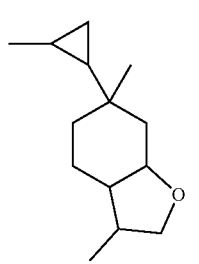
NP-1
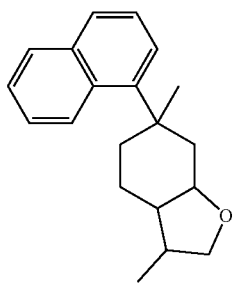
-continued
Bu-8
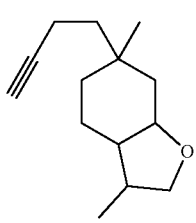
Pr-10
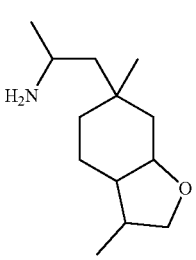
Pr-11
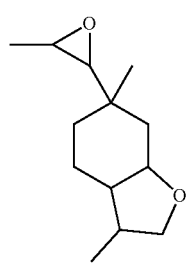
Pr-12
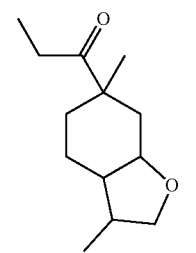
sBu-7-Me
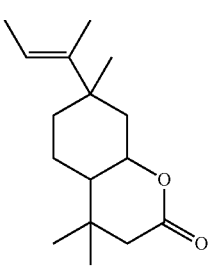
Et-8
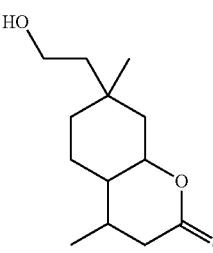

-continued
Et-9
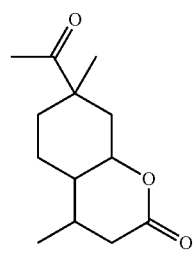
Me-17
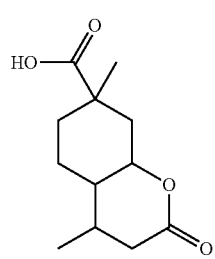
Me-18
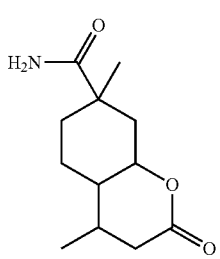
Me-19
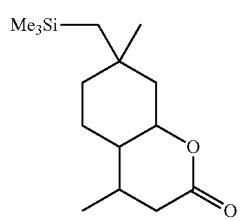
Et-10
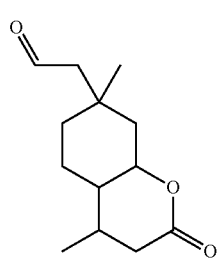
Bu-1
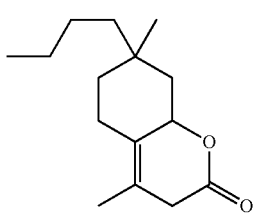
-continued
Me-20
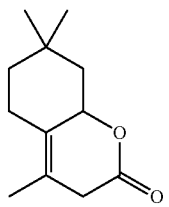
HF-1
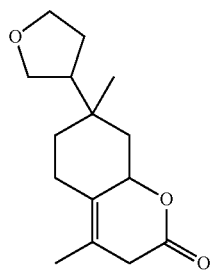
Et-11
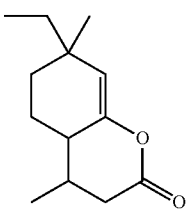
Et-12
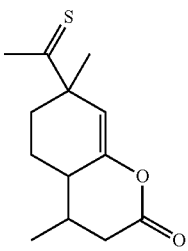
Et-13
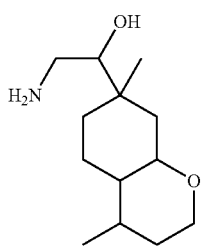
BC-1
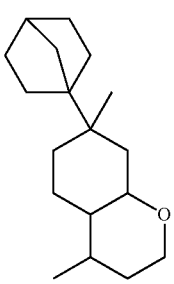

-continued

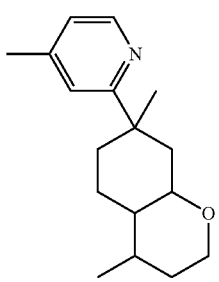
Py-2

<Production Method>

Synthesis methods (following scheme 1) for a lactone derivative and an ether derivative, which are respectively represented by the formula (A) and the formula (B) in which the carbon bond (1) is a single bond, the carbon bond (2) is a double bond, R and R" represent an n-butyl group, R' represents a hydrogen atom, and n is 0, are exemplified to describe a production method for the compounds in the present invention, but the production method is not limited to the following method.

In the reaction (II), an intermediate (b) that is an isopulegol derivative is obtained from the intermediate (a) by, for example, a ring-closure reaction described in JP-A-2012-131785, Synthesis, 1978, P. 147-148, or Org. Biomol. Chem, 2015, 13, P. 5817-5825.

In the reaction (III), an intermediate (c) that is a paramenthane derivative is obtained from the intermediate (b) by, for example, a brown hydroboration reaction or a method described in Chem. Commun. 2016, 52, P. 11897-11900.

In the reaction (IV), a lactone derivative (d) is obtained from the intermediate (c) by, for example, a method described in Tetrahedron 1993, 49, 29, P. 6429-6436.

In the reaction (V), an ether derivative (e) is obtained from the intermediate (c) by, for example, a dehydration cyclization reaction with an acid catalyst or a method described in ChemSusChem, 2012, 5, P. 1578-1586.

In the reaction (VI), a lactone derivative (f) is obtained from the lactone derivative (d) by, for example, a method described in Tetrahedron 1993, 49, 29, P. 6429-6436.

In the reaction (VII), the lactone derivative (f) is obtained from the intermediate (b) by performing ozone decomposition followed by cyclization according to a method described in CA 2997950 A1.

Scheme 1

[Chem. 8]

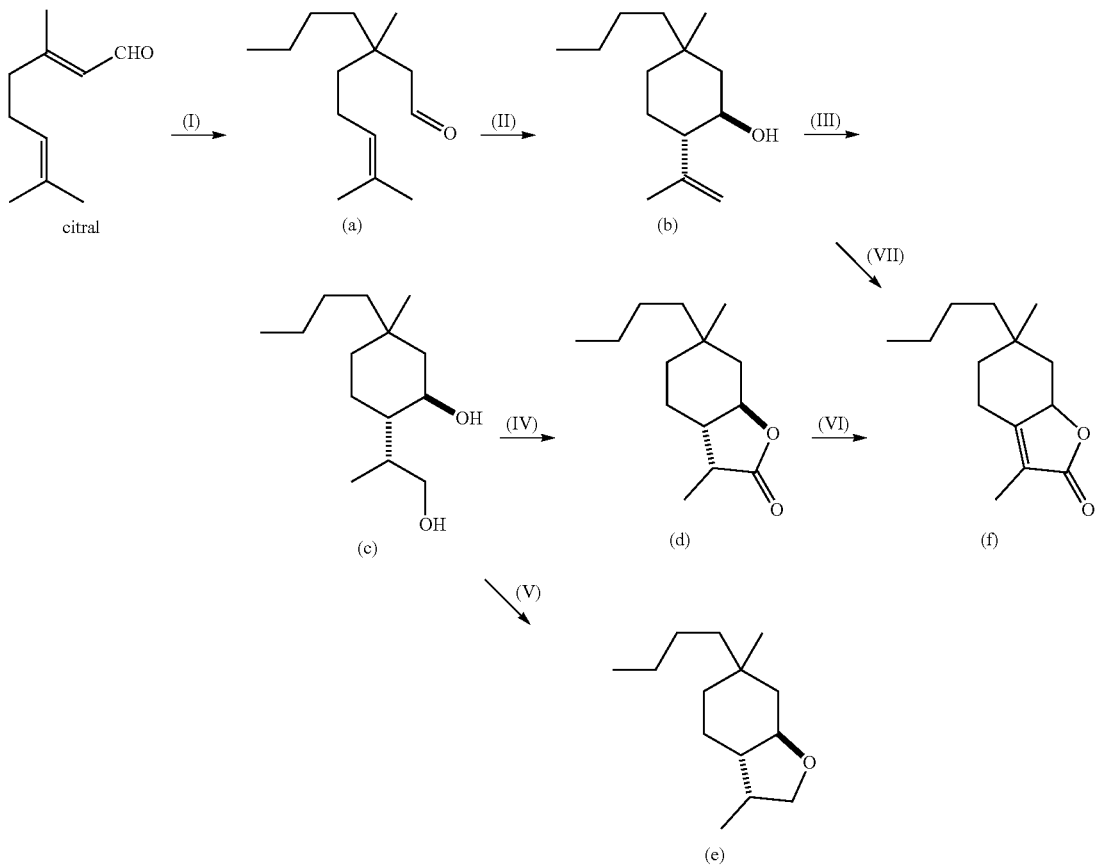

In the reaction (I), citral is allowed to react with, for example, butyl lithium or butyl magnesium halide in the presence of monovalent copper halide as a catalyst, thereby obtaining an intermediate (a) that is a citronellal derivative.

A lactone derivative, which is represented by the formula (A) in which the carbon bond (1) is a double bond, the carbon bond (2) is a single bond, R represents an n-butyl group, R' represents a hydrogen atom, and n is 0, is synthesized by, for example, the method (scheme 2) shown below, but the synthesis method is not limited to the following method.

Scheme 2

[Chem. 9]

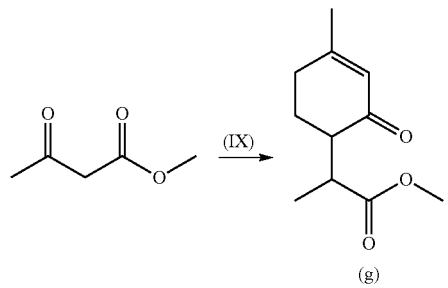

In the reaction (IX), an intermediate (g) can be obtained from methyl acetoacetate according to a method described in WO 2012/165164 A1.

In the reaction (X), a conjugation addition reaction is performed by allowing, for example, butyl lithium or butyl magnesium halide and monovalent copper halide to act on the intermediate (g), thereby obtaining a lactone derivative (h).

A lactone derivative and an ether derivative, which are respectively represented by the formula (A) and the formula (B) in which the carbon bond (1) is a single bond, the carbon bond (2) is a single bond, R and R" represent an n-butyl group, R' represents a hydrogen atom, and n is 1, are synthesized by, for example, the method (scheme 3) shown below, but the synthesis method is not limited to the following method.

Scheme 3

[Chem. 10]

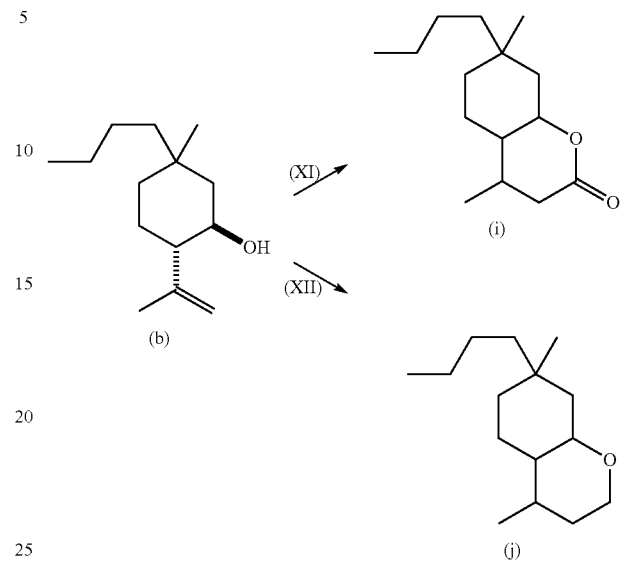

In the reaction of (XI), a lactone derivative (i) is obtained from the intermediate (b) obtained in the scheme 1 by, for example, a method described in Tetrahedron Asymmetry 1999, 10, P. 929-936, or performing ozone decomposition and a Homer Emmons reaction followed by a reduction reaction and a cyclization reaction.

In the reaction of (XII), an ether derivative (j) is obtained by performing cyclization of the intermediate (b), followed by dehydration and hydrogenation, according to a method described in Tetrahedron 1993, 49, 29, P. 6429-6436. The ether derivative (j) is also obtained by applying the method in (XI).

A lactone derivative, which is represented by the formula (A) in which the carbon bond (1) is a single bond, the carbon bond (2) is a single bond, R is a hydrogen atom, R' is an n-butyl group, and n is 0, is synthesized by, for example, the method (scheme 4) shown below, but the synthesis method is not limited to the following method.

Scheme 4

[Chem. 11]

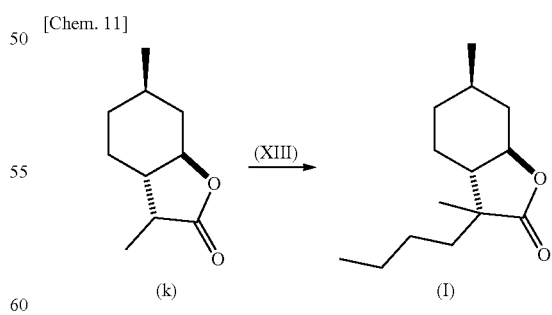

In the reaction (XIII), a lactone derivative (I) is obtained from a lactone compound (k) by, for example, allowing lithium diisopropylamide and alkyl halide to act thereon.

The compound in the present invention thus obtained can be isolated and purified as necessary. Examples of the isolation and purification methods include column chromatography, distillation under reduced pressure, and the like, and these methods can be used alone or in combination.

The compounds represented by the formulas (A) and (B) contained in the flavor or fragrance composition in the present invention respectively may be an optically active substance and a stereoisomer such as a diastereomer depending on steric configuration at 1-, 3-, 4-, and 8-positions of a paramenthane skeleton. All of these isomers have good aromas. In the case where the compounds represented by the formulas (A) and (B) are used for a flavor or fragrance composition, a racemate thereof may be used, or an optically active substance thereof may be used. In the case of using an optically active substance thereof, the optical purity is 20% e.e. to 99.9% e.e., preferably 50% e.e. to 99.9% e.e. In the case of using a stereoisomer thereof such as a diastereomer, the isomer purity is 20% d.e. to 99.9% d.e., preferably 50% d.e. to 99.9% d.e.

The optical purity and the isomer ratio can be measured by, for example, NMR and/or various chromatography using a column (or a chiral column).

The flavor or fragrance composition in the present invention contains at least one kind of compounds represented by the formulas (A) and (B). The blending amount of the compounds represented by the formulas (A) and (B) to the flavor or fragrance composition is not particularly limited, and is preferably 0.01 wt % to 60 wt %, particularly preferably 0.1 wt % to 40 wt %.

Compounded flavor or fragrances commonly used may be blended with the flavor or fragrance composition in the present invention. The flavor or fragrance composition obtained in this manner can provide an aroma imparted with high palatability.

Examples of products that can be perfumed using the flavor or fragrance composition containing the lactone compound or the ether compound respectively represented by the general formulas (A) and (B) in the present invention are not particularly limited, and examples of the products include beverages, foods, fragrances or cosmetics, toiletry products, air care products, daily necessities and household goods, oral compositions, hair care products, skin care products, body care products, detergents for clothes, soft finishing agents for clothes, quasi-drugs, pharmaceuticals, and the like.

Specific examples of the beverages or the foods are not limited in any way, and include beverages such as fruit juice drinks, fruit wines, milk drinks, carbonated drinks, soft drinks, and health drinks; ices such as ice creams, sherbets and ice candies; desserts such as jelly and pudding; western confectioneries such as cakes, cookies, chocolates and chewing gums; Japanese sweets such as bean-jam bun, sweet bean jelly, and uiro; jams; candies; breads; tea drinks or luxury drinks such as green tea, Oolong tea, black tea, persimmon leaf tea, chamomile tea, low striped bamboo tea, mulberry tea, dokudami tea, Pu-er tea, mate tea, rooibos tea, Gymnema tea, Guava tea, coffee, and cocoa; soups such as Japanese style soup, Western style soup and Chinese soup; flavor seasoning; various instant beverages or foods; various snack foods; oral compositions such as dentifrice, oral cleaner, mouth wash, troche, chewing gums; and the like.

Examples of the fragrances or cosmetics, the toiletry products, the air care products, the daily necessities and household goods, the oral compositions, the hair care products, the skin care products, the body care products, the detergents for clothes, the soft finishing agents for clothes, and the quasi-drugs include fragrance products, foundation cosmetics, finishing cosmetics, hair cosmetics, suntan cosmetics, medicated cosmetics, hair care products, soaps, body washers, bath agents, detergents, soft finishing agents, cleaners, kitchen cleaners, bleaching agents, aerosol agents, deodorants or aromatics, repellents, other household goods, and the like.

More specifically, as the fragrance products, examples thereof include perfume, eau de parfum, eau de toilette, eau de cologne, and the like;

as the foundation cosmetics, examples thereof include facial wash creams, vanishing creams, cleansing creams, cold creams, massage creams, milky lotions, skin lotions, beauty lotions, facial packs, makeup removers, and the like;

as the finishing cosmetics, examples thereof include foundations, face powders, solid face powders, talcum powders, rouges, lip balms, cheek rouges, eye liners, mascara, eye shadows, eyebrow pencils, eye packs, nail enamels, enamel removers, and the like; and as the hair cosmetics, examples thereof include pomade, brilliantine, hair set lotions, hair sticks, hair solids, hair oils, hair treatments, hair creams, hair tonics, hair liquids, hair sprays, bandolines, revitalizing hair tonics, hair dyes, and the like.

As the suntan cosmetics, examples thereof include suntan products, sun-screen products, and the like;

as the medicated cosmetics, examples thereof include antiperspirants, after-shaving lotions or gels, permanent wave agents, medicated soaps, medicated shampoos, medicated skin cosmetics, and the like;

as the hair care products, examples thereof include shampoos, rinses, rinse-in-shampoos, conditioners, treatments, hair packs and the like;

as the soap, examples thereof include toilet soaps, bath soaps, perfume soaps, transparent soaps, synthetic soaps, and the like;

as the body washers, examples thereof include body soaps, body shampoos, hand soaps, and the like;

as the bath agents, examples thereof include bathing agents (such as bath salts, bath tablets, and bath liquids), foam bath (such as bubble bath), bath oils (such as bath perfumes, and bath capsules), milk-baths, bath jelly, bath cubes, and the like; and as the detergents, examples thereof include heavy detergents for clothes, light detergents for clothes, liquid detergents, washing soaps, compact detergents, powder soaps, and the like.

As the soft finishing agent, examples thereof include softener, furniture care, and the like;

as the cleaners, examples thereof include cleansers, house cleaners, toilet cleaners, bath cleaners, glass cleaners, mildew removers, cleaners for drainpipe use, and the like;

as the kitchen cleaners, examples thereof include kitchen soaps, kitchen synthetic soaps, tableware cleaners, and the like;

as the bleaching agents, examples thereof include oxidation type bleaching agents (such as chlorine type bleaching agents, and oxygen type bleaching agents), reduction type bleaching agents (such as sulfur type bleaching agents), optical bleaching agents, and the like;

as the aerosol agents, examples thereof include spray type ones, powder sprays, and the like;

as the deodorants or aromatics, examples thereof include solid type ones, gel type ones, liquid type ones, and the like; and as the household goods, examples thereof include tissue papers, toilet papers, and the like.

Specific examples of the pharmaceuticals include, but are not limited to, external preparations for skin such as poultices and ointments, internal preparations, and the like.

The form of the products, which can be perfumed using the flavor or fragrance composition containing the lactone compound or the ether compound respectively represented by the general formulas (A) and (B), may be the form of a mixture itself, and as another form, examples thereof include: a liquid form obtained by dissolving in alcohols, polyhydric alcohols such as propylene glycol, glycerin, and dipropylene glycol, or esters such as triethyl citrate, benzyl benzoate, and diethyl phthalate; natural gums such as gum arabic, and tragant gum; an emulsified form obtained by emulsifying with an emulsifier such as a glycerin fatty acid ester or a sucrose fatty acid ester a powder form obtained by coating with an excipient such as natural gums like gum arabic, gelatin, dextrin, and the like; a solubilized form or dispersed form obtained by solubilizing or dispersing by using a surfactant such as a nonionic surfactant, an anionic surfactant, a cationic surfactant, or an amphoteric surfactant; and a microcapsule obtained by treating with an encapsulating agent; and any form may be selected and used depending on the purpose.

The above fragrance composition may be included in an inclusion agent such as cyclodextrin to stabilize the composition and also make it sustained-releasable, and then may be used. These compositions are used in a form suitable for the form of a final product, for example, a liquid form, a solid form, a powder form, a gel form, a mist form, an aerosol form, or the like.

A predetermined amount of a lactone compound or an ether compound is added to an existing flavor or fragrance, so that the palatability can be higher, and aroma can be improved to have a better fragrance note. The unpleasant fragrance note in the flavor or fragrance can also be reduced. Regarding the addition form, the compounds may be added directly, or the inclusion agent listed above may be used.

EXAMPLES

Hereinafter, the present invention is described in detail with reference to Examples, but the present invention is not limited to these Examples. The measurements for the products in Synthesis Examples and Examples were performed using the following apparatuses and devices.
NMR: DRX500 (manufactured by Bruker Corporation)
CC/MS: GCMS-QP2010 (manufactured by Shimadzu Corporation)
Column: RTX-1 (length 30 m×inner diameter 0.25 mm, liquid phase thickness 0.25 μm)
GC purity: GC-4000Plus (manufactured by GL Sciences Inc.)
Column: RTX-1 (length 30 m×inner diameter 0.25 mm, liquid phase thickness 0.25 μm)
Inert Cap-WAX (length 15 m×inner diameter 0.25 mm, liquid phase thickness 0.25 μm)
Optical purity: GC-2010 (manufactured by Shimadzu Corporation)
Column: beta-DEX225 (manufactured by RESTEK, length 30 m×inner diameter 0.25 mm, liquid phase thickness 0.25 μm)
beta-DEX325 (manufactured by RESTEK, length 30 m×inner diameter 0.25 mm, liquid phase thickness 0.25 μm)
HYDRODEX β-3p (manufactured by MACHEREY-NAGEL, length 20 m×inner diameter 0.25 mm)
Optical rotation: P-1020 (manufactured by JASCO Corporation)

Examples 1 to 16: 1,4 Addition Reaction

[Example 1] Synthesis of 3-methyl Citronellal

The reaction was performed under a nitrogen atmosphere. A 1 L four-neck flask equipped with a dropping funnel was prepared, and copper iodide (27.3 g, 1.05 eq) and diethyl ether (200 ml) were added to the flask. The temperature of the inside of the system was lowered to 0° C. to 5° C. while stirring the mixture. A methyl lithium/ether solution (1.13 mol/L, 260 ml, 2.05 eq. vs CuI) was added dropwise through the dropping funnel over one and a half hours. After the completion of the dropwise addition, stirring was performed for 30 minutes while maintaining the temperature, and the temperature of the inside of the system was lowered to −60° C. or lower. Citral (20.8 g, 137 mmol) and diethyl ether (100 ml) were slowly added dropwise through the dropping funnel over 1 hour. After the completion of the dropwise addition, stirring was performed for 1 hour while maintaining the temperature, and the temperature of the inside of the system was gradually raised to room temperature. As a post-treatment, the temperature of the inside of the system was lowered to 0° C. to 5° C., and a saturated aqueous ammonium chloride solution was slowly added dropwise. The oil layer was washed three times with the saturated aqueous ammonium chloride solution and was washed once with saturated saline solution, followed by drying with anhydrous magnesium sulfate and the concentration under reduced pressure was performed, and the resulting product was purified with column chromatography, thereby obtaining desired 3-methyl citronellal (17.2 g, 75% yield).

3-methyl Citronellal $^1$H-NMR (500 MHz, CDCl$_3$): δ 0.93 (s, 6H), 1.33-1.39 (m, 2H), 1.60 (s, 3H), 1.68 (3H, d, J=0.85 Hz), 1.94-2.01 (m, 2H), 2.27 (2H, d, J=3.2 Hz), 5.06-5.11 (1H, m), 9.85 (1H, t, J=3.1 Hz).
$^{13}$C-NMR (125 MHz, CDCl$_3$): 17.6 (CH3), 22.7 (CH2), 25.7 (CH3), 27.4 (2C, CH3), 33.5 (C), 42.7 (CH2), 54.7 (CH2), 124.3 (CH), 131.6 (C), 203.6 (C).

[Example 2] Synthesis of 3-ethyl Citronellal 3-ethyl citronellal (3.01 g, 16.7 mmol, 67% yield) was obtained from citral (3.70 g, 24.3 mmol) in the same manner as in Example 1 except that ethyl lithium was used instead of methyl lithium.

3-ethyl Citronellal $^1$H-NMR (500 MHz, CDCl$_3$): δ 0.86 (3H, t, J=7.5 Hz), 1.03 (s, 3H), 1.31-1.38 (2H, m), 1.41 (2H, q, J=7.6 Hz), 1.60 (s, 3H), 1.68 (3H, s), 1.90-1.98 (2H, m), 2.27 (2H, d, J=3.2 Hz), 5.00-5.15 (1H, m), 9.85 (1H, t, J=3.2 Hz).
$^{13}$C-NMR (125 MHz, CDCl$_3$): 8.0 (CH3), 17.6 (CH3), 22.6 (CH2), 24.8 (CH3), 25.7 (CH3), 32.3 (CH2), 36.2 (C), 39.6 (CH2), 52.4 (CH2), 124.3 (CH), 131.6 (C), 203.8 (C).

[Example 3] Synthesis of 3-butyl Citronellal

The reaction was performed under a nitrogen atmosphere. A 1 L four-neck flask equipped with a dropping funnel was prepared, and copper iodide (45.7 g, 1.05 eq) and diethyl ether (200 ml) were added to the flask. The temperature of the inside of the system was lowered to 0° C. to 5° C. while stirring the mixture. An n-butyl lithium/ether solution (1.6 mol/L, 300 ml, 2.10 eq vs Cu) was added dropwise through the dropping funnel over one and a half hours. After the completion of the dropwise addition, stirring was performed for 30 minutes while maintaining the temperature, and the temperature of the inside of the system was lowered to −60° C. or lower. Citral (34.8 g, 228 mmol) and diethyl ether (50 ml) were added dropwise through the dropping funnel over 2 hours. After the completion of the dropwise addition, stirring was performed for 1 hour while maintaining the temperature, and the temperature of the inside of the system was gradually raised to room temperature. As a post-treatment, the temperature of the inside of the system was lowered to 0° C. to 5° C., and a saturated aqueous ammonium chloride solution was slowly added dropwise. The oil layer was washed three times with a saturated aqueous ammonium chloride solution and was washed once with a saturated saline solution, followed by drying with anhydrous magnesium sulfate, and the concentration under reduced pressure was performed. The obtained crude product was distilled (bath temperature: 110° C., tower top temperature: 68° C. to 75° C., decompression degree: 0.25 torr), thereby obtaining desired 3-butyl citronellal (37.5 g, 78% yield).

3-butyl Citronellal $^1$H-NMR (500 MHz, CDCl$_3$): δ 0.91 (3H, t, J=6.9 Hz), 1.04 (3H, s), 1.20-1.38 (8H, m), 1.60 (3H, s), 1.68 (3H, s), 1.89-1.97 (2H, m), 2.27 (2H, d, J=3.2 Hz), 5.05-5.11 (1H, m), 9.85 (1H, t, J=3.2 Hz).
$^{13}$C-NMR (125 MHz, CDCl$_3$): 14.1 (CH3), 17.6 (CH3), 22.3 (CH2), 23.4 (CH2), 25.3 (CH3), 25.7 (CH3), 25.8 (CH2), 36.1 (C), 39.7 (CH2), 40.0 (CH2), 52.9 (CH2), 124.3 (CH), 131.5 (C), 203.8 (C).

[Example 4] Synthesis of 3-phenyl Citronellal 3-phenyl citronellal (18.2 g, 79.0 mmol, 81% yield) was obtained from citral (14.8 g, 97.1 mmol) in the same manner as in Example 3 except that phenyllithium was used instead of n-butyl lithium.

3-phenyl Citronellal $^1$H-NMR (500 MHz, CDCl$_3$): δ 1.45 (6H, d, J=13.6 Hz), 1.66 (3H, s), 1.67-1.81 (4H, m), 2.54 (1H, dd, J=15.1, 3.4 Hz), 2.82 (1H, dd, J=15.2, 2.5 Hz), 4.99-5.04 (1H, br), 7.22 (1H, qui, J=4.5 Hz), 7.34 (4H, d, J=4.5 Hz), 9.52 (1H, dd, J=3.3, 2.4 Hz).
$^{13}$C-NMR (125 MHz, CDCl$_3$): 17.5 (CH3), 22.6 (CH2), 24.7 (CH2), 25.6 (CH3), 39.9 (C), 43.6 (CH2), 55.5 (CH2), 123.9 (CH), 126.1 (2C, CH), 126.2 (CH), 128.5 (2C, CH), 131.8 (C), 145.6 (C), 203.1 (C).

[Example 5] Synthesis of 3-butyl Citronellal

The reaction was performed under a nitrogen atmosphere. To a 2 L four-neck flask equipped with a dropping funnel, a copper bromide/dimethyl sulfide complex (4.28 g, 5 mol %), DMI (90.5 mL, 2 eq.), and THF (200 mL) were added, and the temperature of the inside of the system was lowered to about −35° C. while stirring the mixture. Further, citral (63.5 g, 417 mmol) and chlorotrimethylsilane (84.6 mL, 1.6 eq.) were added to the inside of the system, and a butyl magnesium chloride/THF solution (1.0 mol/L, 500 mL, 1.2 eq.) was added dropwise through the dropping funnel over 3 hours. Analysis of the reaction was conducted by GC. It was confirmed that the citral disappeared completely, and then, the post-treatment was performed. The temperature of the inside of the system was raised to 0° C. or higher (the highest temperature being 11° C.), and an aqueous solution (500 mL) of citric acid (80 g, 1.0 eq.) was added dropwise. Further, 1N hydrochloric acid (100 mL) and heptane (250 mL) were added to perform washing. In the system, uniform two layers were formed. The aqueous layer was distilled off (pH=1), followed by performing the washing once with 1N hydrochloric acid and performing the washing twice with 10% saline solution, and a mixed liquid of an aqueous ammonia and 5% aqueous sodium bicarbonate solution was added to the inside of the system. It was conformed that the aqueous layer did not turn blue, followed by performing washing three times with a saturated saline solution, and the oil layer was dried with anhydrous magnesium sulfate. After filtration and concentration, the desired 3-butylcitronellal crude product (101 g) was obtained. The 3-butylcitronellal crude product was used for the next reaction as it is without subjecting to purification.

[Example 6] Synthesis of 3-ethyl Citronellal 3-ethyl citronellal (12.1 g) was obtained as a crude product from citral (10.0 g, 65.7 mmol) in the same manner as in Example 5 except that ethyl magnesium chloride was used instead of butyl magnesium chloride.

[Example 7] Synthesis of 3-isopropyl Citronellal 3-isopropyl citronellal (17.2 g) was obtained as a crude product from citral (10.0 g, 65.7 mmol) in the same manner as in Example 5 except that isopropyl magnesium chloride was used instead of butyl magnesium chloride.

[Example 8] Synthesis of 3-propyl Citronellal 3-propyl citronellal (6.58 g, 34% yield) was obtained from citral (15.0 g, 98.5 mmol) in the same manner as in Example 5 except that propyl magnesium chloride was used instead of butyl magnesium chloride.

3-propyl Citronellal $^1$H-NMR (500 MHz, CDCl$_3$): δ 0.91 (3H, t, J=6.9 Hz), 1.04 (3H, s), 1.25-1.39 (6H, m), 1.60 (3H, s), 1.68 (3H, s), 1.89-1.96 (2H, m), 2.27 (2H, d, J=3.3 Hz), 5.00-5.13 (1H, m), 9.85 (1H, t, J=3.2 Hz).
$^{13}$C-NMR (125 MHz, CDCl$_3$): 14.1 (CH3), 16.8 (CH2), 17.6 (CH2), 22.3 (CH2), 25.3 (CH3), 25.7 (CH3), 36.2 (C), 40.8 (CH2), 42.4 (CH2), 52.9 (CH2), 124.3 (CH), 131.6 (C), 203.8 (CH).

[Example 9] Synthesis of 3-iso-butyl Citronellal 3-iso-butyl citronellal (30.9 g) was obtained as a crude product from citral (21.8 g, 143 mmol) in the same manner as in Example 5 except that iso-butyl magnesium chloride was used instead of butyl magnesium chloride.

[Example 10] Synthesis of 3-sec-butyl Citronellal 3-sec-butyl citronellal (15.9 g) was obtained as a crude product from citral (10.0 g, 65.7 mmol) in the same manner as in Example 5 except that sec-butyl magnesium chloride was used instead of butyl magnesium chloride.

[Example 11] Synthesis of 3-n-pentyl Citronellal 3-n-pentyl citronellal (29.0 g) was obtained as a crude product from citral (15.0 g, 98.5 mmol) in the same manner as in Example 5 except that n-pentyl magnesium bromide was used instead of butyl magnesium chloride.

[Example 12] Synthesis of 3-(3-pentyl) Citronellal 3-(3-pentyl) citronellal (4.01 g, 17.9 mmol, 21% yield) was obtained as an isolated and purified product by column chromatography from citral (12.9 g, 84.6 mmol) in the same manner as in Example 5 except that 3-pentylmagnesium chloride was used instead of butyl magnesium chloride.

3-(3-pentyl) Citronellal $^1$H-NMR (500 MHz, CDCl$_3$) 0.83-0.99 (7H, m), 1.06 (3H, s), 1.12 (2H, qui, J=7.1 Hz), 1.38-1.58 (4H, m), 1.60 (3H, s), 1.68 (3H, s), 1.89-1.96 (2H, m), 2.32 (1H, ddd, J=24.0, 14.4, 3.4 Hz), 5.05-5.12 (1H, m), 9.87 (1H, t. J=3.2 Hz).
$^{13}$C-NMR (125 MHz, CDCl$_3$): 14.4 (CH3), 14.5 (CH3), 17.6 (CH3), 22.4 (CH2), 22.9 (CH3), 23.0 (CH2), 23.2 (CH2), 25.7 (CH3), 38.4 (CH2), 40.2 (C), 49.3 (CH), 51.1 (CH2), 124.4 (CH), 131.6 (C), 204.3 (CH).

[Example 13] Synthesis of 3-n-hexyl Citronellal 3-n-hexyl citronellal (24.0 g) was obtained as a crude product from citral (15.0 g, 98.5 mmol) in the same manner as in Example 5 except that n-hexyl magnesium chloride was used instead of butyl magnesium chloride.

[Example 14] Synthesis of 3-cyclohexyl Citronellal 3-cyclohexyl citronellal (18.0 g) was obtained as a crude product from citral (13.8 g, 90.9 mmol) in the same manner as in Example 5 except that n-cyclohexyl magnesium chloride was used instead of butyl magnesium chloride.

[Example 15] Synthesis of 3-n-heptyl Citronellal 3-n-heptyl citronellal (21.7 g) was obtained as a crude product from citral (13.8 g, 90.9 mmol) in the same manner as in Example 5 except that n-heptyl magnesium bromide was used instead of butyl magnesium chloride.

[Example 16] Synthesis of 3-n-octyl Citronellal 3-n-octyl citronellal (5.87 g, 28% yield) was obtained from citral (12.0 g, 78.8 mmol) in the same manner as in Example 5 except that n-octyl magnesium chloride was used instead of butyl magnesium chloride.

3-n-octyl Citronellal $^1$H-NMR (500 MHz, CDCl$_3$): δ 0.91 (3H, t, J=6.8 Hz), 1.04 (3H, s), 1.25-1.39 (16H, m), 1.60 (3H, s), 1.68 (3H, s), 1.88-1.97 (2H, m), 2.27 (2H, d, J=3.2 Hz), 5.00-5.13 (1H, m), 9.84 (1H, t, J=3.2 Hz).
$^{13}$C-NMR (125 MHz, CDCl$_3$): 14.1 (CH3), 17.6 (CH3), 22.3 (CH2), 22.7 (CH3), 23.6 (CH2), 25.3 (CH3), 25.7 (CH3), 29.3 (CH2), 29.6 (CH2), 30.3 (CH2), 31.9 (CH2), 36.2 (C), 40.0 (CH2×2), 52.9 (CH2), 124.3 (CH), 131.6 (C), 203.9 (CH).

Examples 17 to 35: Ring-Closure Reaction

[Example 17] Synthesis of Optically Active (−)-5-methylisopulegol

The reaction was performed in accordance with Org. Biomol. Chem, 2015, 13, P. 5817-5825. To a 100 ml four-neck flask equipped with a condenser, (R)-BINOL (1.23 mg, 1.6 eq. vs Al) and toluene (s/s=3, 27 ml) were added under a nitrogen atmosphere, and triethyl aluminum was added slowly while stirring the mixture. After stirring the mixture for one hour at room temperature, the temperature of the inside of the system was lowered to 0° C. to 5° C., and 3-methyl citronellal (9.00 g, 53.5 mmol) obtained in Example 1 was slowly added dropwise. After 3 hours, the completion of the reaction was confirmed by GC, and the reaction was terminated. As a post-treatment, after quenching with toluene/hydrochloric acid, the oil layer was washed once with tap water and once with a saturated saline solution. The washed oil layer was dried with anhydrous magnesium sulfate, followed by passing it through silica gel column chromatography, and the concentration under reduced pressure was performed, thereby obtaining desired optically active (−)-5-methylisopulegol (7.42 g, 83% yield).

Optically Active (−)-5-methylisopulegol $[a]^{20}_D$=−6.6 (c0.64, CHCl$_3$)
$^1$H-NMR (500 MHz, CDCl$_3$): δ 0.93 (3H, s), 0.96 (3H, s), 1.14 (1H, t, J=11.7 Hz), 1.22 (1H, td, J=13.0, 4.6 Hz), 1.26-1.41 (2H, m), 1.45-1.57 (2H, m), 1.74 (3H, dd, J=1.5, 0.9 Hz), 1.75-1.87 (2H, m), 3.61-3.66 (1H, m), 4.85-4.86 (1H, m), 4.89-4.91 (1K, m)
$^{13}$C-NMR (125 MHz, CDCl$_3$): δ 19.2 (CH3), 25.1 (CH3), 26.4 (CH2), 32.2 (C), 33.0 (CH3), 38.6 (CH2), 46.8 (CH2), 54.8 (CH), 67.6 (CH), 112.8 (CH2), 146.7 (C) 89% e.e.;

[Example 18] Synthesis of Optically Active (+)-5-methylisopulegol

Optically active (+)-5-methylisopulegol (896 mg, 90% yield) was obtained from 3-methyl citronellal (1.00 g, 5.94 mmol) obtained in Example 1 in the same manner as in Example 17 except that (S)-BINOL was used instead of (R)-BINOL.

Optically Active (+)-5-methylisopulegol $[a]^{20}_D$=−6.6 (c0.64, CHCl3)
$^1$H-NMR (500 MHz, CDCl$_3$): δ 0.93 (3H, s), 0.96 (3H, s), 1.14 (1H, t, J=11.7 Hz), 1.22 (1H, td, J=13.0, 4.6 Hz), 1.26-1.41 (2H, m), 1.45-1.57 (2H, m) 1.74 (3H, dd, J=1.5, 0.9 Hz), 1.75-1.87 (2H, m), 3.61-3.66 (1H, m), 4.85-4.86 (1H, m), 4.89-4.91 (1H, m)
$^{13}$C-NMR (125 MHz, CDCl$_3$): δ 19.2 (CH3), 25.1 (CH3), 26.4 (CH2), 32.2 (C), 33.0 (CH3), 38.6 (CH2), 46.8 (CH2), 54.8 (CH), 67.6 (CH), 112.8 (CH2), 146.7 (C) 89% e.e.;

[Example 19] Synthesis of Optically Active (−)-5-butylisopulegol

Optically active (−)-5-butylisopulegol (4.41 g, 90% yield) was obtained in the same manner as in Example 17 except that 3-butyl citronellal (5.00 g, 23.8 mmol) obtained in Example 3 was used instead of 3-methyl citronellal.

Optically Active (−)-5-butylisopulegol $^1$H-NMR (500 MHz, CDCl$_3$): δ 0.91-1.07 (6H, m), 1.10 (1H, tJ=11.7 Hz), 1.14-1.41 (7H, m), 1.43-1.62 (3H, m), 1.74 (1H, s), 1.77-1.91 (3H, m), 3.65 (1H, ddd, J=10.7, 10.7, 4.4 Hz), 4.88 (2H, d, J=20.4 Hz) (major);
$^1$H-NMR (500 MHz, CDCl$_3$): δ 0.88-0.91 (6H, m), 1.05 (1H, t, J11.7 Hz), 1.14-1.41 (7H, m), 1.43-1.62 (3H, m), 1.75

(3H, br), 1.77-1.91 (3H, m), 3.61 (1H, ddd, J=10.8, 10.5, 4.2 Hz), 4.88 (2H, d, J=20.4 Hz) (minor)

$^{13}$C-NMR (125 MHz, CDCl$_3$): 14.1 (CH3), 19.3 (CH3), 22.7 (CH3), 23.6 (CH2), 25.4 (CH2), 26.1 (CH2), 34.7 (C), 36.9 (CH2), 45.1 (CH2), 45.9 (CH2), 55.1 (CH), 67.6 (CH), 112.7 (CH2), 146.7 (C) (major)

$^{13}$C-NMR (125 MHz, CDCl$_3$): 14.1 (CH3), 19.3 (CH3), 23.5 (CH2), 25.4 (CH2), 25.8 (CH2), 29.4 (C1-3), 34.7 (C), 37.1 (CH2), 44.9 (CH2), 45.9 (CH2), 54.8 (CH), 67.1 (CH), 112.7 (CH2), 146.7 (C) (minor)

74% e.e. (major)
88% e.e. (minor)

[Example 20] Synthesis of Optically Active (+)-5-butylisopulegol

Optically active (+)-5-butylisopulegol (4.86 g, 97% yield) was obtained in the same manner as in Example 17 except that (S)-BINOL was used instead of (R)-BINOL, and 3-butyl citronellal (5.00 g, 23.8 mmol) obtained in Example 3 was used instead of 3-methyl citronellal.

Optically Active (+)-5-butylisopulegol $[a]^D{}_{20}$=+68.1 (c0.30, CHCl$_3$, mixture)

$^1$H-NMR (500 MHz, CDCl$_3$): δ 0.91-1.08 (6H, m), 1.10 (1H, t, J=11.7 Hz), 1.14-1.41 (7H, m), 1.43-1.62 (3H, m), 1.74 (3H, s), 1.76-1.91 (3H, m), 3.65 (1H, ddd, J=10.7, 10.7, 4.4 Hz), 4.88 (2H, d, J=20.4 Hz) (major);

$^1$H-NMR (500 MHz, CDCl$_3$): δ 0.88-0.91 (6H, m), 1.05 (1H, t, J11.7 Hz), 1.14-1.41 (7H, m), 1.43-1.62 (3H, m), 1.75 (3H, br), 1.76-1.91 (3H, m), 3.61 (1H, ddd, J=10.8, 10.5, 4.2 Hz), 4.88 (2H, d, =20.4 Hz) (minor)

$^{13}$C-NMR (125 MHz, CDCl$_3$): 14.1 (CH3), 19.3 (CH3), 22.7 (CH3), 23.6 (CH2), 25.4 (CH2), 26.1 (CH2), 34.7 (C), 36.9 (CH2), 45.1 (CH2), 45.9 (CH2), 55.1 (CH), 67.6 (CH), 112.7 (CH2), 146.7 (C) (major)

$^{13}$C-NMR (125 MHz, CDCl$_3$): 14.1 (CH3), 19.3 (CH3), 23.5 (CH2), 25.4 (CH2), 25.8 (CH2), 29.4 (CH3), 34.7 (C), 37.1 (CH2), 44.9 (CH2), 45.9 (CH2), 54.9 (CH), 67.1 (CH), 112.7 (CH2), 146.7 (C) (minor)

56% e.e. (major)
81% e.e. (minor)

[Example 21] Synthesis of 5-ethylisopulegol

The reaction was performed under a nitrogen atmosphere. To a 300 mL reactor equipped with a condenser, the crude 3-ethyl citronellal mixture (7.90 g) obtained in Example 6, toluene (40 mL), zinc chloride or zinc bromide (395 mg, 5 wt %), and decanoic acid (237 mg, 3 wt %) were added, and the resulting mixture was heated and stirred at 100° C. for 1 hour. The completion of the reaction was confirmed by GC, and the post-treatment was performed. The solution was cooled to reach room temperature, washing was performed twice with saturated saline solution, followed by drying with anhydrous magnesium sulfate, and the concentration under reduced pressure was performed. The obtained residue was isolated and purified by silica gel column chromatography, thereby obtaining 1.99 g of the desired 5-ethylisopulegol (2 steps, 33% yield).

5-ethylisopulegol $^1$H-NMR (500 MHz, CDCl$_3$): δ 0.82-0.87 (m, 3H), 0.90 (s, 3H, C—CH$_3$), 1.02-1.63 (m, 7H), 1.76 (s, 3H, C=C—CH$_3$), 1.80-1.96 (m, 3H), 3.62-3.69 (m, 1H, CH—OH), 4.88 (d, 2H, J=21.0 Hz, C=CH$_2$) (major).

$^1$H-NMR (500 MHz, CDCl$_3$): δ 0.82-0.85 (m, 3H), 0.88 (s, 3H, C—CH$_3$), 1.02-1.63 (m, 7H), 1.73 (s, 3H, C=C—CH$_3$), 1.80-1.96 (m, 3H), 3.56-3.62 (m, 1H, CH—OH), 4.88 (d, 2H, J=21.0 Hz, C=CH$_2$) (minor).

$^{13}$C-NMR (125 MHz, CDCl$_3$): 7.6 (CH$_3$), 19.3 (CH$_3$), 22.1 (CH$_3$), 26.1 (CH$_2$), 34.7 (C), 36.4 (CH$_2$), 38.2 (CH$_2$), 44.6 (CH$_2$), 55.1 (CH), 67.6 (CH), 112.7 (CH$_2$), 146.7 (C) (major).

$^{13}$C-NMR (125 MHz, CDCl$_3$): 7.9 (CH), 19.3 (CH$_3$), 22.1 (CH$_3$), 25.8 (CH$_2$), 34.6 (C), 36.6 (CH$_2$), 38.2 (CH$_2$), 44.6 (CH$_2$), 54.8 (CH), 67.1 (CH), 112.7 (CH$_2$), 146.7 (C) (minor).

HRMS calcd for $C_{12}H_{22}O$ (M+) 182.1622, found 182.1671.

[Example 22] Synthesis of 5-methylisopulegol 5-methylisopulegol (8.71 g, 87% yield) was obtained in the same manner as in Example 21 except that 3-methyl citronellal (10.0 g, 59.4 mmol) obtained in Example 1 was used instead of 3-ethyl citronellal.

5-methylisopulegol $^1$H-NMR (500 MHz, CDCl$_3$): δ 0.94 (3H, s), 0.97 (3H, s), 1.14 (1H, t, J=11.5 Hz), 1.17-1.31 (2H, m), 1.35-1.42 (1H, m), 1.45-1.58 (2H, m), 1.74 (3H, dd, J=1.5, 1.0 Hz), 1.78 (1H, dq, J=12.5, 2.01 Hz), 1.81-1.87 (1H, m), 3.61-3.67 (1H, m), 4.86-4.87 (1H, m), 4.89-4.91 (1H, m).

$^{13}$C-NMR (125 MHz, CDCl$_3$): 19.3 (CH3), 25.1 (CH3), 26.4 (CH2), 32.1 (C), 33.0 (CH3), 38.5 (CH2), 46.8 (CH2), 54.8 (CH), 67.6 (CH), 112.8 (CH2), 146.6 (C).

HRMS calcd for $C_{11}H_{20}O$ (M+) 168.1514, found 168.1516.

[Example 23] Synthesis of 5-propylisopulegol 5-propylisopulegol (5.04 g, 84% yield) was obtained in the same manner as in Example 21 except that 3-propyl citronellal (6.00 g) obtained in Example 8 was used instead of 3-ethyl citronellal.

5-propylisopulegol $^1$H-NMR (500 MHz, CDCl$_3$): δ 0.88-0.93 (6H, m), 1.03-1.22 (5H, m), 1.28-1.41 (3H, m), 1.45-1.59 (3H, m), 1.74 (3H, s), 1.76-1.86 (1H, m), 3.65 (1H, dt, J=10.5, 4.0 Hz), 4.88 (2H, d, J=20.0 Hz) (major);

$^1$H-NMR (500 MHz, CDCl$_3$): δ 0.88-0.93 (6H, m), 1.03-1.30 (7H, m), 1.35-1.41 (1H, m), 1.45-1.59 (3H, m), 1.74 (3H, s), 1.82-1.93 (1H, m), 3.61 (1H, dt, J=10.5, 4.0 Hz), 4.88 (2H, d, J=20.0 Hz) (minor)

$^{13}$C-NMR (125 MHz, CDCl$_3$): 15.0 (CH3), 16.4 (CH2), 19.3 (CH3), 22.7 (CH3), 26.1 (CH2), 34.8 (C), 36.9 (CH2), 45.1 (CH2), 48.7 (CH2), 55.1 (CH), 67.6 (CH), 112.7 (CH2), 146.7 (C) (major)

$^{13}$C-NMR (125 MHz, CDCl$_3$): 15.1 (CH3), 16.8 (CH2), 19.3 (CH3), 25.9 (CH2), 29.5 (CH3), 34.7 (C), 37.1 (CH2), 39.1 (CH2), 45.0 (CH2), 54.8 (CH), 67.1 (CH), 112.7 (CH2), 146.7 (C) (minor)

[Example 24] Synthesis of 5-isopropylisopulegol 5-isopropylisopulegol (3.17 g, 2 steps, 27% yield) was obtained from 3-isopropyl citronellal (17.2 g) in the same manner as in Example 21 except that the crude 3-isopropyl citronellal obtained in Example 7 was used instead of 3-ethyl citronellal.

5-isopropylisopulegol $^1$H-NMR (500 MHz, CDCl$_3$): δ 0.78-0.90 (9H, m), 1.03-1.67 (8H, m), 1.73 (3H, s), 1.88 (1H, ddd, J=12.5, 4.4, 2.3 Hz), 3.66 (1H, td, J=10.7, 4.2 Hz), 1.76-1.86 (1H, m), 3.65 (1H, dt, J=10.5, 4.0 Hz), 4.86 (1H, br), 4.89-4.92 (1H, m) (major);
$^{13}$C-NMR (125 MHz, CDCl$_3$): 16.8 (CH3), 16.9 (CH3), 18.1 (CH3), 19.3 (CH3), 26.1 (CH2), 34.8 (CH2), 37.0 (C), 39.5 (CH), 43.2 (CH2), 54.9 (CH), 67.9 (CH), 12.7 (CH2), 146.7 (C) (major)

[Example 25] Synthesis of 5-butylisopulegol 5-butylisopulegol (8.34 g, 2 steps, 28% yield) was obtained from 3-butyl citronellal (30.9 g) in the same manner as in Example 21 except that the crude 3-butyl citronellal mixture obtained in Example 5 was used instead of 3-ethyl citronellal.

5-butylisopulegol $^1$H-NMR (500 MHz, CDCl$_3$): δ 0.90-0.93 (m, 6H), 1.10 (t, 1H, J=11.5 Hz), 1.15-1.41 (m, 7H), 1.45-1.62 (m, 3H), 1.74 (br, 3H, C=C—CH3), 1.77-1.90 (m, 3H), 3.65 (tq, 1H, J=11.0, 1.5 Hz, CH—OH), 4.84-4.87 (br, 1H, C=CH2), 4.89-4.92 (br, 1H, C=CH2) (major).
$^1$H-NMR (500 MHz, CDCl$_3$): δ 0.88-0.91 (m, 6H), 1.02-1.40 (m, 8H), 1.45-1.62 (m, 3H), 1.75 (d, 3H, J=2.0 Hz, C=C—CH$_3$), 1.77-1.90 (m, 3H), 3.57-3.65 (m, 1H, CH—OH), 4.84-4.87 (br, 1H, C=CH2), 4.89-4.92 (br, 1H, C=CH2) (minor).
$^{13}$C-NMR (125 MHz, CDCl$_3$): 14.1 (CH3), 19.3 (CH3), 22.7 (CH3), 23.6 (CH2), 25.4 (CH2), 26.1 (CH2), 34.7 (C), 36.9 (CH2), 45.1 (CH2), 45.9 (CH2), 55.1 (CH), 67.6 (CH), 112.7 (CH2), 146.7 (C) (major).
$^{13}$C-NMR (125 MHz, CDCl$_3$): 14.1 (CH3), 19.3 (CH3), 23.6 (CH2), 25.4 (CH2), 25.9 (CH2), 29.4 (CH3), 34.7 (C), 37.1 (CH2), 44.9 (CH2), 45.9 (CH2), 54.8 (CH), 67.1 (CH), 112.7 (CH2), 146.7 (C) (minor)

[Example 26] Synthesis of 5-(1α, 2β, 5β)-butylisopulegol 5-butylisopulegol (22.1 g) obtained in Example 25 was further isolated and purified, thereby obtaining 5-(1α, 2β, 5β)-butylisopulegol (751 mg).

5-(1α, 2β, 5β)-butylisopulegol $^1$H-NMR (500 MHz, CDCl$_3$): δ 0.88-0.91 (6H, m), 1.05 (1H, t, J11.7 Hz), 1.14-1.41 (7H, m), 1.43-1.62 (3H, m), 1.75 (3H, br), 1.76-1.91 (3H, m), 3.61 (1H, ddd, J=10.8, 10.5, 4.2 Hz), 4.88 (2H, d, J=20.4 Hz)
$^{13}$C-NMR (125 MHz, CDCl$_3$): 14.1 (CH3), 19.3 (CH3), 23.5 (CH2), 25.4 (CH2), 25.8 (CH2), 29.4 (CH3), 34.7 (C), 37.1 (CH2), 44.9 (CH2), 45.9 (CH2), 54.9 (CH), 67.1 (CH), 112.7 (CH2), 146.7 (C)

[Example 27] Synthesis of 5-iso-butylisopulegol 5-iso-butylisopulegol (13.4 g, 2 steps, 50% yield) was obtained from 3-iso-butyl citronellal (30.9 g) in the same manner as in Example 21 except that the crude 3-iso-butyl citronellal obtained in Example 9 was used instead of 3-ethyl citronellal.

[Example 28] Synthesis of 5-sec-butylisopulegol 5-sec-butylisopulegol (2.03 g, 2 steps, 15% yield) was obtained from 3-sec-butyl citronellal (15.9 g) in the same manner as in Example 21 except that the 3-sec-butyl citronellal crude product obtained in Example 10 was used instead of 3-ethyl citronellal.

[Example 29] Synthesis of 5-n-pentyl Isopulegol 5-n-pentyl isopulegol (3.21 g, 2 steps, 23% yield) was obtained from 3-n-pentyl citronellal crude product (19.7 g) in the same manner as in Example 21 except that the 3-n-pentyl citronellal crude product obtained in Example 11 was used instead of 3-ethyl citronellal.

5-n-pentyl Isopulegol $^1$H-NMR (500 MHz, CDCl$_3$): δ 0.85-0.94 (6H, m), 1.02-1.40 (12H, m), 1.46-1.57 (3H, m), 1.73 (3H, s), 1.77-1.87 (1H, m), 3.65 (1H, dt, J=10.8, 4.3 Hz), 4.88 (2H, d, J=19.9 Hz) (major)
$^1$H-NMR (500 MHz, CDCl$_3$): δ 0.85-0.94 (6H, m), 1.02-1.40 (12H, m), 1.46-1.57 (3H, m), 1.73 (3H, s), 1.83-1.93 (1H, m), 3.61 (1H, dt, J=10.4, 4.2 Hz), 4.88 (2H, d, J=19.9 Hz) (minor)
$^{13}$C-NMR (125 MHz, CDCl$_3$): 14.1 (CH3), 19.2 (CH3), 22.6 (CH3), 22.8 (CH2), 23.1 (CH2), 26.1 (CH2), 32.7 (CH2), 34.7 (C), 36.8 (CH2), 45.0 (CH2), 46.1 (CH2), 55.1 (CH), 67.6 (CH), 112.7 (CH2), 146.7 (C) (major)
$^{13}$C-NMR (125 MHz, CDCl$_3$): 14.1 (CH3), 19.3 (CH3), 22.7 (CH2), 22.8 (CH2), 25.9 (CH2), 29.4 (CH3), 32.8 (CH2), 34.5 (C), 36.6 (CH2), 37.1 (CH2), 44.9 (CH2), 54.7 (CH), 67.1 (CH), 112.7 (CH2), 146.7 (C) (minor)

[Example 30] Synthesis of 5-(3-pentyl)isopulegol 5-(3-pentyl)isopulegol (2.27 g, 76% yield) was obtained in the same manner as in Example 21 except that 3-(3-pentyl) citronellal (2.70 g, 13.8 mmol) obtained in Example 12 was used instead of 3-ethyl citronellal.

5-(3-pentyl)isopulegol $^1$H-NMR (500 MHz, CDCl$_3$): δ 0.72 (hep, J=3.6 Hz), 0.83-0.95 (6H, m), 1.03-1.30 (18H, m), 1.42-1.61 (3H, m), 1.73 (3H, s), 1.79-1.87 (1H, m), 3.65 (1H, dt, J=10.6, 4.4 Hz), 4.88 (2H, d, J=20.2 Hz) (major)
$^1$H-NMR (500 MHz, CDCl$_3$): δ 0.72 (hep, J=3.6 Hz), 0.83-0.95 (6H, m), 1.03-1.30 (18H, m), 1.42-1.61 (3H, m), 1.73 (3H, s), 1.91 (ddd, J=12.6.4.4.2.2 Hz), 3.65 (1H, dt, J=10.6, 4.4 Hz), 4.88 (2H, d, J=20.2 Hz) (minor)
$^{13}$C-NMR (125 MHz, CDCl$_3$): 14.6 (CH3×2), 19.2 (CH3), 19.6 (CH3), 22.6 (CH2), 22.7 (CH2), 25.9 (CH2), 34.9 (CH2), 38.6 (C), 43.2 (CH2), 54.7 (CH), 54.9 (CH), 57.7 (CH), 112.7 (CH2), 146.7 (C) (major)
$^{13}$C-NMR (125 MHz, CDCl$_3$): 14.6 (CH3), 19.2 (CH3), 19.6 (CH3), 22.2 (CH2), 22.6 (CH2), 25.7 (CH2), 25.9 (CH3), 34.9 (CH2), 38.3 (C), 42.9 (CH), 43.2 (CH2), 54.7 (CH), 54.9 (CH), 112.7 (CH2), 146.7 (C) (minor)

[Example 31] Synthesis of 5-n-hexyl Isopulegol 5-n-hexyl isopulegol (6.02 g, 2 steps, 26% yield) was obtained from 3-n-hexyl citronellal (24.0 g) in the same manner as in Example 21 except that the 3-n-hexyl citronellal crude product obtained in Example 13 was used instead of 3-ethyl citronellal.

5-n-hexyl Isopulegol $^1$H-NMR (500 MHz, CDCl$_3$): δ 0.85-0.94 (6H, m), 1.03-1.41 (14H, m), 1.45-1.59 (3H, m), 1.74 (3H, s), 1.76-1.87 (1H, m), 3.65 (1H, dt, J=11.0, 4.5 Hz), 4.88 (2H, d, J=19.5 Hz) (major)
$^1$H-NMR (500 MHz, CDCl$_3$): δ 0.85-0.94 (6H, m), 1.07-1.41 (14H, m), 1.45-1.59 (3H, m), 1.74 (3H, s), 1.84-1.93 (1H, m), 3.61 (1H, dt, J=11.0, 4.0 Hz), 4.88 (2H, d, J=19.5 Hz) (minor)
$^{13}$C-NMR (125 MHz, CDCl$_3$): 14.1 (CH3), 19.3 (CH3), 22.6 (CH2), 22.7 (CH3), 23.1 (CH2), 26.1 (CH2), 30.2 (CH2), 31.9 (CH2), 34.7 (C), 36.9 (CH2), 45.1 (CH2), 46.1 (CH2), 55.1 (CH), 67.6 (CH), 112.7 (CH2), 146.7 (C) (major)
$^{13}$C-NMR (125 MHz, CDCl$_3$): 14.1 (CH3), 19.3 (CH3), 22.6 (CH2), 23.5 (CH2), 25.9 (CH2), 29.4 (CH3), 30.3 (CH2), 31.9 (CH2), 34.6 (C), 36.7 (CH2), 37.1 (CH2), 44.9 (CH2), 54.8 (CH), 67.1 (CH), 112.7 (CH2), 146.7 (C) (minor)

[Example 32] Synthesis of 5-cyclohexyl Isopulegol 5-cyclohexyl isopulegol (7.63 g, 2 steps, 39% yield) was obtained from 3-cyclohexyl citronellal (18.0 g) in the same manner as in Example 21 except that the 3-cyclohexyl citronellal crude product obtained in Example 14 was used instead of 3-ethyl citronellal.

[Example 33] Synthesis of 5-n-heptyl Isopulegol 5-n-heptyl isopulegol (6.89 g, 2 steps, 31% yield) was obtained from 3-n-heptyl citronellal (21.7 g) in the same manner as in Example 21 except that the 3-n-heptyl citronellal crude product obtained in Example 15 was used instead of 3-ethyl citronellal.

5-n-heptyl Isopulegol $^1$H-NMR (500 MHz, CDCl$_3$): δ 0.85-0.94 (6H, m), 1.03-1.41 (16H, m), 1.45-1.59 (3H, m), 1.73 (3H, s), 1.76-1.87 (1H, m), 3.65 (1H, dt, J=10.8, 4.4 Hz), 4.88 (2H, d, J=20.8 Hz) (major)
$^1$H-NMR (500 MHz, CDCl$_3$): δ 0.85-0.94 (6H, m), 1.03-1.41 (16H, m), 1.45-1.59 (3H, m), 1.73 (3H, s), 1.76-1.87 (1H, m), 3.61 (1H, dt, J=10.9, 4.2 Hz), 4.88 (2H, d, J=20.8 Hz) (minor)
$^{13}$C-NMR (125 MHz, CDCl$_3$): 14.1 (CH3), 19.3 (CH3), 22.6 (CH2), 22.7 (CH3), 23.2 (CH2), 26.1 (CH2), 29.4 (CH2), 30.5 (CH2), 31.9 (CH2), 34.7 (C), 36.9 (CH2), 45.0 (CH2), 46.2 (CH2), 55.1 (CH), 67.6 (CH), 112.7 (CH2), 146.7 (C) (major)
$^{13}$C-NMR (125 MHz, CDCl$_3$): 14.1 (CH3), 19.3 (CH3), 22.6 (CH2), 23.6 (CH2), 25.9 (CH2), 29.4 (CH2), 29.4 (CH3), 30.6 (CH2), 31.9 (CH2), 34.6 (C), 36.7 (CH2), 37.1 (CH2), 44.9 (CH2), 54.8 (CH), 67.1 (CH), 112.7 (CH2), 146.7 (C) (minor)

[Example 34] Synthesis of 5-n-octyl Isopulegol 5-n-octyl isopulegol (4.29 g, 78% yield) was obtained in the same manner as in Example 21 except that 3-n-octyl citronellal (5.50 g) obtained in Example 16 was used instead of 3-ethyl citronellal.

5-n-octyl Isopulegol $^1$H-NMR (500 MHz, CDCl$_3$): δ 0.85-0.93 (6H, m), 1.02-1.40 (18H, m), 1.44-1.57 (3H, m), 1.73 (3H, s), 1.78-1.88 (1H, m), 3.65 (1H, dt, J=10.7, 4.3 Hz), 4.88 (2H, d, J=19.1 Hz) (major)
$^1$H-NMR (500 MHz, CDCl$_3$): δ 0.85-0.93 (6H, m), 1.02-1.40 (18H, m), 1.44-1.57 (3H, m), 1.73 (3H, s), 1.83-1.92 (1H, m), 3.61 (1H, dt, J=10.5, 4.0 Hz), 4.88 (2H, d, J=19.1 Hz) (minor)
$^{13}$C-NMR (125 MHz, CDCl$_3$): 14.1 (CH3), 19.3 (CH3), 22.6 (CH2), 22.6 (CH3), 23.1 (CH2), 26.1 (CH2), 29.3 (CH2), 29.7 (CH2), 30.5 (CH2), 31.9 (CH2), 34.7 (C), 36.9 (CH2), 45.0 (CH2), 46.2 (CH2), 55.1 (CH), 67.6 (CH), 112.7 (CH2), 146.7 (C) (major)
$^{13}$C-NMR (125 MHz, CDCl$_3$): 14.1 (CH3), 19.3 (CH3), 22.6 (CH2), 23.6 (CH2), 25.9 (CH2), 29.3 (CH2), 29.4 (CH3), 29.7 (CH2), 30.6 (CH2), 31.9 (CH2), 34.6 (C), 36.9 (CH2), 37.1 (CH2), 45.0 (CH2), 54.7 (CH), 67.1 (CH), 112.7 (CH2), 146.7 (C) (minor)

[Example 35] Synthesis of 5-phenylisopulegol 5-phenylisopulegol (1.58 g, 85% yield) was obtained in the same manner as in Example 21 except that 3-phenyl citronellal (2.00 g, 8.68 mmol) obtained in Example 4 was used instead of 3-ethyl citronellal.

5-phenylisopulegol $^1$H-NMR (500 MHz, CDCl$_3$): δ 1.32 (3H, s), 1.32-1.50 (2H, m), 1.52 (3H, s), 1.53-1.75 (2H, m), 1.88-2.04 (2H, m), 2.38 (1H, dq, J=13.8, 3.0 Hz), 2.71 (1H, dt, J=13.3, 2.9 Hz), 3.45 (1H, td, J=11.0, 3.9 Hz), 4.77-4.85 (2H, m), 7.10-7.45 (5H, m) (major).
$^1$H-NMR (500 MHz, CDCl$_3$): δ 1.20 (3H, s), 1.35-1.73 (5H, m), 1.79 (3H, s), 1.86-2.04 (2H, m), 2.30 (1H, dq, J=12.5, 2.0 Hz), 3.84 (1H, td, J=10.7, 4.2 Hz), 4.90-4.96 (2H, m), 7.10-7.45 (5H, m) (minor).
$^{13}$C-NMR (125 MHz, CDCl$_3$): 19.3 (CH3), 25.5 (CH3), 26.3 (CH2), 37.1 (CH2), 38.8 (C), 44.8 (CH2), 54.6 (CH), 67.8 (CH), 112.9 (CH2), 124.9 (CH), 125.8 (CH), 125.9 (CH), 128.2 (CH), 128.5 (CH), 146.4 (C), 151.3 (C) (major).
$^{13}$C-NMR (125 MHz, CDCl$_3$): 19.1 (CH3), 26.5 (CH2), 35.3 (CH3), 37.0 (CH2), 40.0 (C), 44.9 (CH2), 54.9 (CH), 67.3 (CH), 112.7 (CH2), 124.9 (CH), 125.6 (CH), 125.9 (CH), 128.2 (CH), 128.5 (CH), 146.3 (C), 146.6 (C) (minor).

Examples 36 to 55

[Example 36] Synthesis of 1-butyl paramenthane-3,9-diol

The reaction was performed under a nitrogen atmosphere. To a 100 mL reactor equipped with a dropping funnel, 5-butylisopulegol (3.40 g, 16.2 mmol) obtained in Example 25 and THF (5 mL) were added, and a borane/THF/THF solution (1.0 mol/L, 24.2 mL, 1.5 eq.) was added through the dropping funnel. The temperature of the inside of the system was lowered to 0° C. to 5° C. while stirring the mixture, and a borane solution was added dropwise over about 45 minutes. Ater the completion of dropwise addition, stirring was performed for 1 hour at room temperature, an aqueous sodium hydroxide solution (25 wt %, 9.9 mL, 3 eq.) was added through the dropping funnel. First, a few drops of tap water was added to the inside of the system, and after the confirmation of settlement of the foam, an aqueous sodium hydroxide solution was added dropwise over 15 minutes (max 25° C.). The temperature of the inside of the system returned to room temperature again by water bath, and a hydrogen peroxide solution (30% aqueous solution, 24.8 mL, 12 eq.) was added through the dropping funnel. The hydrogen peroxide solution was added dropwise over about 15 minutes, and after the completion of the dropwise addition, the mixture was stirred under reflux for 1 hour. The completion of the reaction was confirmed by GC, and the post-treatment was performed. The reaction solution was added to heptane 1N hydrochloric acid, and the oil layer was separated. The aqueous layer was extracted with heptane and the obtained oil layers were combined therewith, followed by washing three times with a saturated saline solution. The oil layers were dried with anhydrous magnesium sulfate, and filtration and concentration were performed to obtain a crude product. Isolation and purification was performed with column chromatography, thereby obtaining the desired 1-buty paramenthane-3,9-diol (2.21 g, 9.69 mmol, 60% yield) as colorless oil.

1-butyl paramenthane-3,9-diol $^1$H-NMR (500 MHz, CDCl$_3$): δ 0.85-0.93 (6H, m), 0.98 (3H, d, J=7.4 Hz), 1.04-1.48 (12H, m), 1.71 (1H, ddd, J=12.3, 4.3, 2.4 Hz), 1.84-1.91 (1H, m), 2.49-3.27 (2H, br), 3.58-3.70 (3H, m) (major)

$^1$H-NMR (500 MHz, CDCl$_3$): δ 0.86-0.93 (6H, m), 0.98 (3H, d, J=7.3 Hz), 1.05-1.48 (12H, m), 1.78-1.91 (2H, m), 2.49-3.27 (2H, br), 3.58-3.70 (3H, m) (minor)

$^{13}$C-NMR (125 MHz, CDCl$_3$): 12.0 (CH3), 14.1 (CH3), 22.4 (CH3), 23.6 (CH2), 25.5 (CH2), 25.8 (CH2), 34.6 (C), 37.1 (CH2), 38.6 (CH), 45.7 (CH2), 47.1 (CH2), 49.4 (CH), 67.3 (CH2), 67.4 (CH) (major)

$^{13}$C-NMR (125 MHz, CDCl$_3$): 12.0 (CH3), 14.1 (CH3), 23.6 (CH2), 25.5 (CH2), 25.7 (CH2), 29.2 (CH3), 34.4 (C), 36.2 (CH2), 37.2 (CH2), 38.6 (CH), 45.7 (CH2), 48.9 (CH), 66.9 (CH2), 67.2 (CH) (minor)

[Example 37] Synthesis of 1-methyl paramenthane-3,9-diol 1-methyl paramenthane-3,9-diol (3.85 g, 65% yield) was obtained as colorless oil in the same manner as in Example 36 except that 5-methylisopulegol (5.38 g, 32.0 mmol) obtained in Example 22 was used instead of 5-butylisopulegol.

1-methyl paramenthane-3,9-diol $^1$H-NMR (500 MHz, CDCl$_3$): δ 0.88 (3H, s), 0.94 (3H, s), 0.98 (3H, d, J=7.3 Hz), 1.11-1.47 (5H, m), 1.64-1.68 (1H, m), 1.70 (1H, dq, J=12.3, 4.3, 2.6 Hz), 1.83-1.91 (1H, m), 2.93 (2H, br), 3.59-3.70 (3H, m)

$^{13}$C-NMR (125 MHz, CDCl$_3$): 12.0 (CH3), 24.9 (CH3), 26.1 (CH2), 32.1 (C), 32.8 (CH3), 38.6 (CH), 38.8 (CH2), 48.8 (CH2), 49.1 (CH), 67.2 (CH2), 67.4 (CH)

[Example 38] Synthesis of (3R,4S)-1-methylparamenthane-3,9-diol

Optically active (3R,4S)-1-methylparamenthane-3,9-diol (3.03 g, 91% yield) was obtained as colorless oil in the same manner as in Example 36 except that optically active (−)-5-methylisopulegol ((−)-1R,2S-5-methylisopulegol) (3.00 g, 17.8 mmol) obtained in Example 17 was used instead of 5-butylisopulegol.

(3R,4S)-5-methylparamenthane-3,9-diol $^1$H-NMR (500 MHz, CDCl$_3$): δ 0.88 (3H, s), 0.94 (3H, s), 0.98 (3H, d, J=7.3 Hz), 1.10-1.47 (5H, m), 1.64-1.68 (1H, m), 1.70 (1H, dq, J=12.3, 4.3, 2.6 Hz), 1.83-1.91 (1H, m), 2.93 (2H, br), 3.59-3.70 (3H, m)

$^{13}$C-NMR (125 MHz, CDCl$_3$): 12.0 (CH3), 24.9 (CH3), 26.0 (CH2), 32.1 (C), 32.8 (CH3), 38.6 (CH), 38.8 (CH2), 48.8 (CH2), 49.1 (CH), 67.2 (CH2), 67.4 (CH)

[Example 39] Synthesis of (3S,4R)-1-methylparamenthane-3,9-diol

Optically active (3S,4R)-1-methylparamenthane-3,9-diol (2.47 g, 81% yield) was obtained as colorless oil in the same manner as in Example 36 except that optically active (+)-5-methylisopulegol ((+)-1S,2R-5-methylisopulegol) (2.70 g, 16.0 mmol) obtained in Example 18 was used instead of 5-butylisopulegol.

(3S,4R)-5-methylparamenthane-3,9-diol $^1$H-NMR (500 MHz, CDCl$_3$): 0.88 (3H, s), 0.94 (3H, s), 0.98 (3H, d, J=7.3 Hz), 1.11-1.47 (5H, m), 1.64-1.68 (1H, m), 1.70 (1H, dq, J=12.3, 4.3, 2.6 Hz), 1.83-1.93 (1H, m), 2.93 (2H, br), 3.59-3.69 (3H, m)

$^{13}$C-NMR (125 MHz, CDCl$_3$): 12.0 (CH3), 24.9 (CH3), 26.1 (CH2), 32.1 (C), 32.8 (CH3), 38.6 (CH), 38.8 (CH2), 48.8 (CH2), 49.1 (CH), 67.2 (CH2), 67.4 (CH)

[Example 40] Synthesis of 1-ethylparamenthane-3,9-diol 1-ethylparamenthane-3,9-diol (3.10 g, 15.5 mmol, 81% yield) was obtained in the same manner as in Example 36 except that 5-ethylisopulegol (3.50 g, 19.2 mmol) obtained in Example 21 was used instead of 5-butylisopulegol.

1-ethylparamenthane-3,9-diol $^1$H-NMR (500 MHz, CDCl$_3$): δ 0.77-0.90 (6H, m), 0.97 (3H, d, J=7.7 Hz), 1.01-1.60 (8H, m), 1.70 (1H, ddd, J=12.4, 4.1, 2.5 Hz), 1.76-1.85 (1H, m), 3.52-3.66 (3H, m), 4.14 (2H, br) (major)

$^1$H-NMR (500 MHz, CDCl$_3$): δ 0.77-0.90 (6H, m), 0.97 (3H, d, J=7.7 Hz), 1.01-1.60 (8H, m), 1.76-1.85 (2H, m), 3.52-3.66 (3H, m), 4.14 (2H, br) (minor)

$^{13}$C-NMR (125 MHz, CDCl$_3$): 7.59 (CH3), 11.9 (CH3), 21.8 (CH3), 26.0 (CH2), 28.5 (CH2), 34.5 (C), 36.6 (CH2), 38.0 (CH2), 38.9 (CH), 49.4 (CH), 66.9 (CH2), 67.0 (CH), (major)

$^{13}$C-NMR (125 MHz, CDCl$_3$): 7.89 (CH3), 1.9 (CH3), 25.8 (CH2), 28.5 (CH3), 34.4 (C), 36.7 (CH2), 38.9 (CH), 46.4 (CH2), 46.4 (CH2), 49.0 (CH), 66.4 (CH), 67.0 (CH2), (minor)

[Example 41] Synthesis of 1-isopropyl paramenthane-3,9-diol 1-isopropyl paramenthane-3,9-diol (2.81 g, 10.8 mmol, 92% yield) was obtained as a crude product in the same manner as in Example 36 except that 5-isopropylisopulegol (2.80 g, 14.3 mmol) obtained in Example 24 was used instead of 5-butylisopulegol. The compound was used for the next reaction as it is without subjecting to purification.

[Example 42] Synthesis of 1-propyl paramenthane-3,9-diol 1-propyl paramenthane-3,9-diol (3.68 g, 88% yield) was obtained in the same manner as in Example 36 except that 5-propylisopulegol (3.82 g, 19.5 mmol) obtained in Example 23 was used instead of 5-butylisopulegol.

[Example 43] Synthesis of 1-iso-butyl paramenthane-3,9-diol 1-iso-butyl paramenthane-3,9-diol (6.02 g, 26.4 mmol, 93% yield) was obtained as a crude product in the same manner as in Example 36 except that 5-iso-butylisopulegol (6.00 g, 28.5 mmol) obtained in Example 27 was used instead of 5-butylisopulegol. The compound was used for the next reaction as it is without subjecting to purification.

[Example 44] Synthesis of 1-sec-butyl paramenthane-3,9-diol 1-sec-butyl paramenthane-3,9-diol (1.69 g, 7.41 mmol, 86% yield) was obtained as a crude product in the same manner as in Example 36 except that 5-sec-butylisopulegol (1.81 g, 8.60 mmol) obtained in Example 28 was used instead of 5-butylisopulegol. The compound was used for the next reaction as it is without subjecting to purification.

[Example 45] Synthesis of Optically Active 1-butyl paramenthane-3,9-diol

Optically active 1-butyl paramenthane-3,9-diol (1.48 g, 91% yield) was obtained as colorless oil in the same manner as in Example 36 except that (−)-5-butylisopulegol (1.50 g, 7.13 mmol) obtained in Example 19 was used instead of 5-butylisopulegol.

Optically Active 1-butyl paramenthane-3,9-diol $^1$H-NMR (500 MHz, CDCl$_3$): δ 0.86-0.93 (6H, m), 0.98 (3H, d, J=7.3 Hz), 1.05-1.48 (14H, m), 1.71 (1H, ddd, J=12.3, 4.3, 2.4 Hz), 1.84-1.91 (1H, m), 3.58-3.70 (3H, m) (major)
$^1$H-NMR (500 MHz, CDCl$_3$): δ 0.86-0.93 (6H, m), 0.98 (3H, d, J=7.3 Hz), 1.05-1.48 (14H, m), 1.78-1.91 (2H, m), 3.58-3.70 (3H, m) (minor)
$^{13}$C-NMR (125 MHz, CDCl$_3$): 12.0 (CH3), 14.1 (CH3), 22.4 (CH3), 23.6 (CH2), 25.5 (CH2), 25.8 (CH2), 34.6 (C), 37.0 (CH2), 38.6 (CH), 45.7 (CH2), 47.1 (CH2), 49.4 (CH), 67.3 (CH2), 67.4 (CH) (major)
$^{13}$C-NMR (125 MHz, CDCl$_3$): 12.0 (CH3), 14.1 (CH3), 23.6 (CH2), 25.5 (CH2), 25.7 (CH2), 29.2 (CH3), 34.4 (C), 36.2 (CH2), 37.2 (CH2), 38.6 (CH), 45.7 (CH2), 48.9 (CH), 66.9 (CH2), 67.3 (CH) (minor)

[Example 46] Synthesis of Optically Active 1-butyl paramenthane-3,9-diol

Optically active 1-butyl paramenthane-3,9-diol (1.48 g, 91% yield) was obtained as colorless oil in the same manner as in Example 36 except that (+)-5-butylisopulegol (1.50 g, 7.13 mmol) obtained in Example 20 was used instead of 5-butylisopulegol.

Optically Active 1-butyl paramenthane-3,9-diol $^1$H-NMR (500 MHz, CDCl$_3$): δ 0.86-0.93 (6H, m), 0.98 (3H, d, J=7.3 Hz), 1.05-1.48 (12H, m), 1.71 (1H, ddd, J=12.3, 4.3, 2.4 Hz), 1.84-1.91 (1H, m), 2.52-3.25 (2H, br), 3.58-3.70 (3H, m) (major)
$^1$H-NMR (500 MHz, CDCl$_3$): δ 0.86-0.93 (6H, m), 0.98 (3H, d, J=7.3 Hz), 1.05-1.48 (12H, m), 1.78-1.91 (2H, m), 2.52-3.25 (2H, br), 3.58-3.70 (3H, m) (minor)
$^{13}$C-NMR (125 MHz, CDCl$_3$): 12.0 (CH3), 14.1 (CH3), 22.4 (CH3), 23.6 (CH2), 25.5 (CH2), 25.8 (CH2), 34.6 (C), 37.0 (CH2), 38.6 (CH), 45.7 (CH2), 47.1 (CH2), 49.4 (CH), 67.3 (CH2), 67.4 (CH) (major)
$^{13}$C-NMR (125 MHz, CDCl$_3$): 12.0 (CH3), 14.1 (CH3), 23.6 (CH2), 25.5 (CH2), 25.7 (CH2), 29.2 (CH3), 34.4 (C), 36.2 (CH2), 37.2 (CH2), 38.6 (CH), 45.7 (CH2), 48.9 (CH), 66.9 (CH2), 67.3 (CH) (minor)

[Example 47] Synthesis of single Isomer of 1-butyl paramenthane-3,9-diol

A single isomer of 1-butyl paramenthane-3,9-diol (511 mg, 94% yield) was obtained as colorless oil in the same manner as in Example 36 except that 5-butylisopulegol (1α, 2β, 5β) form (500 mg, 2.38 mmol) obtained in Example 26 was used instead of 5-butylisopulegol.

1-butyl paramenthane-3,9-diol $^1$H-NMR (500 MHz, CDCl$_3$): 0.86-0.93 (6H, m), 0.98 (3H, d, J=7.3 Hz), 1.05-1.48 (12H, m), 1.78-1.91 (2H, m), 2.50-3.25 (2H, br), 3.58-3.70 (3H, m)
$^{13}$C-NMR (125 MHz, CDCl$_3$): 12.0 (CH3), 14.1 (CH3), 23.6 (CH2), 25.5 (CH2), 25.7 (CH2), 29.2 (CH3), 34.4 (C), 36.2 (CH2), 37.2 (CH2), 38.6 (CH), 45.7 (CH2), 48.9 (CH), 66.9 (CH2), 67.3 (CH)

[Example 48] Synthesis of 1-n-pentyl paramenthane-3,9-diol 1-n-pentyl paramenthane-3,9-diol (2.49 g) was obtained in the same manner as in Example 36 except that 5-n-pentyl isopulegol (2.35 g) obtained in Example 29 was used instead of 5-butylisopulegol. The compound was used for the next reaction as it is without subjecting to purification.

[Example 49] Synthesis of 1-(3-pentyl)paramenthane-3,9-diol 1-(3-pentyl)paramenthane-3,9-diol (2.29 g, quant.) was obtained in the same manner as in Example 36 except that 5-(3-pentyl)isopulegol (2.10 g, 9.36 mmol) obtained in Example 30 was used instead of 5-butylisopulegol.

5-(3-pentyl)paramenthane-3,9-diol $^1$H-NMR (500 MHz, CDCl$_3$): δ 0.67-0.74 (1H, m), 0.80 (3H, s), 0.94 (6H, t, J=7.4 Hz), 0.98 (1H, d, J=7.3 Hz), 1.02-1.20 (4H, m), 1.28-1.59 (6H, m), 1.80-1.88 (2H, m), 3.12 (2H, br), 3.57-3.70 (3H, m) (major)
$^1$H-NMR (500 MHz, CDCl$_3$): δ 0.76 (3H, s), 0.94 (6H, t, J=7.4 Hz), 0.99 (1H, d, J=7.3 Hz), 1.02-1.20 (5H, m), 1.28-1.59 (6H, m), 1.80-1.88 (1H, m), 2.05-2.10 (1H, m), 3.12 (2H, br), 3.57-3.70 (3H, m) (minor)
$^{13}$C-NMR (125 MHz, CDCl$_3$): 11.9 (CH3), 14.57 (CH3), 14.62 (CH3), 19.3 (CH3), 22.6 (CH2), 22.7 (CH2), 25.8 (CH2), 35.2 (CH2), 38.5 (C), 38.8 (CH), 45.5 (CH2), 49.2 (CH), 54.6 (CH), 67.2 (CH2), 67.4 (CH) (major)
$^{13}$C-NMR (125 MHz, CDCl$_3$): 11.8 (CH3), 14.2 (CH3), 14.4 (CH3), 22.3 (CH2), 22.5 (CH2), 24.7 (CH3), 25.7 (CH2), 36.4 (CH2), 38.2 (C), 38.8 (CH), 42.7 (CH), 46.4 (CH2), 49.1 (CH), 66.3 (CH), 67.3 (CH2) (minor)

[Example 50] Synthesis of 1-n-hexyl paramenthane-3,9-diol 1-n-hexyl paramenthane-3,9-diol (3.21 g) was obtained in the same manner as in Example 36 except that 5-n-hexyl isopulegol (3.01 g) obtained in Example 31 was used instead of 5-butylisopulegol. The compound was used for the next reaction as it is without subjecting to purification.

[Example 51] Synthesis of 1-cyclohexyl paramenthane-3,9-diol 1-cyclohexyl paramenthane-3,9-diol (6.30 g) was obtained in the same manner as in Example 36 except that 5-cyclohexyl isopulegol (6.00 g) obtained in Example 32 was used instead of 5-butylisopulegol. The compound was used for the next reaction as it is without subjecting to purification.

[Example 52] Synthesis of 1-heptyl paramenthane-3,9-diol 1-n-heptyl paramenthane-3,9-diol (3.44 g) was obtained in the same manner as in Example 36 except that 5-n-heptyl isopulegol (3.08 g) obtained in Example 33 was used instead of 5-butylisopulegol. The compound was used for the next reaction as it is without subjecting to purification.

[Example 53] Synthesis of 1-n-octyl paramenthane-3,9-diol 1-n-octyl paramenthane-3,9-diol (2.04 g) was obtained in the same manner as in Example 36 except that 5-n-octyl isopulegol (2.20 g) obtained in Example 34 was used instead of 5-butylisopulegol. The compound was used for the next reaction as it is without subjecting to purification.

[Example 54] Synthesis of 1-phenyl paramenthane-3,9-diol 1-phenyl paramenthane-3,9-diol (0.83 g, 77% yield) was obtained in the same manner as in Example 36 except that 5-phenylisopulegol (1.00 g, 4.31 mmol) obtained in Example 35 was used instead of 5-butylisopulegol. The compound was used for the next reaction as it is without subjecting to purification.

[Example 55] Synthesis of paramenthane-3,9-diol

Paramenthane-3,9-diol (12.6 g, 72.9 mmol, 75% yield) was obtained in the same manner as in Example 36 except that L-isopulegol (15.0 g, 97.2 mmol) was used instead of 5-butylisopulegol.

Paramenthane-3,9-diol $^1$H-NMR (500 MHz, CDCl$_3$): δ 0.89-1.05 (7H, m), 1.23 (1H, qd, J=12.9, 3.5 Hz), 1.31-1.47 (2H, m), 1.57 (1H, dq, J=13.2, 3.3 Hz), 1.60-1.71 (2H, m), 1.83-1.90 (1H, m), 1.93-1.97 (1H, m), 2.86 (1H, br), 3.14 (1H, br), 3.43-3.68 (3H, m) (major)

$^1$H-NMR (500 MHz, CDCl$_3$): δ 0.84-1.05 (7H, m), 1.23 (1H, qd, J=12.9, 3.5 Hz), 1.31-1.47 (2H, m), 1.57 (1H, dq, J=13.2, 3.3 Hz), 1.60-1.71 (2H, m), 1.83-1.90 (1H, m), 1.95-2.06 (1H, m), 2.86 (1H, br), 3.14 (1H, br), 3.43-3.68 (3H, m) (minor)

$^{13}$C-NMR (125 MHz, CDCl$_3$): 12.0 (CH3), 22.1 (CH3), 29.4 (CH2), 31.5 (CH), 34.6 (CH2), 38.5 (CH), 44.7 (CH2), 48.5 (CH), 67.2 (CH2), 70.3 (CH) (major)

$^{13}$C-NMR (125 MHz, CDCl$_3$): 12.7 (CH3), 22.1 (CH3), 25.5 (CH2), 31.5 (CH), 34.3 (CH2), 36.0 (CH), 45.2 (CH2), 45.9 (CH), 66.8 (CH2), 71.8 (CH) (minor)

Examples 56 to 82: 2H-mint Lactonization

[Example 56] Synthesis of 1-butyl-2H-mintlactone (Exemplary Compound Bu-1aa)

The reaction was performed in accordance with Tetrahedron 1993, 49, 29, P. 6429-6436. To a 100 mL flask equipped with a dean-stark condenser, 1-butyl paramenthane 3,9-diol (200 mg, 0.876 mmol) obtained in Example 36, supported silver carbonate celite (1.06 g, 50 wt % loading, 2.2 eq), and toluene (30 mL) were added, and the mixture was stirred under reflux for 3 hours. The precipitated water was removed by a condenser. The completion of the reaction was confirmed by GC, and the temperature of the inside of the system was lowered to room temperature. The reaction solution was concentrated under reduced pressure after filtration, and the obtained residue was isolated and purified by column chromatography, thereby obtaining 1-butyl-2H-mintlactone (Exemplary Compound Bu-1aa) (114 mg, 0.509 mmol, 58% yield) as the desired colorless oil.

Exemplary Compound Bu-1aa: 1-butyl-2H-mintlactone $^1$H-NMR (500 MHz, CDCl$_3$): δ 0.86-0.94 (3H, m), 0.96 (3H, s), 1.19 (3H, d, J=7.7 Hz), 1.27-1.53 (10H, m), 1.58-1.68 (1H, m), 1.85-1.93 (1H, m), 2.00 (1H, ddd, J=11.7, 3.9, 1.5 Hz), 2.63 (1H, qui, J=7.6 Hz), 4.19 (1H, td, J=11.5, 4.0 Hz) (major)

$^1$H-NMR (500 MHz, CDCl$_3$): 0.86-0.94 (3H, m), 0.96 (3H, s), 1.18 (3H, d, J=7.7 Hz), 1.27-1.53 (10H, m), 1.58-1.68 (1H, m), 1.85-1.93 (1H, m), 2.11-2.16 (1H, m), 2.63 (1H, qui, J=7.6 Hz), 4.12 (1H, td, J=11.5, 4.0 Hz) (minor)

$^{13}$C-NMR (125 MHz, CDCl$_3$): 9.6 (CH$_3$), 14.1 (CH$_3$), 20.8 (CH$_2$) 23.4 (CH$_2$), 23.6 (CH$_3$), 25.4 (CH$_2$), 35.4 (C), 37.3 (CH$_2$), 38.9 (CH), 41.2 (CH$_2$), 45.9 (CH$_2$), 48.2 (CH), 79.3 (CH), 180.4 (C) (major)

$^{13}$C-NMR (125 MHz, CDCl$_3$): 9.6 (CH$_3$), 14.1 (CH$_3$), 20.6 (CH$_2$), 23.5 (CH$_2$), 25.7 (CH$_2$), 29.6 (CH$_3$), 35.3 (C), 37.0 (CH$_2$), 37.8 (CH$_2$), 38.9 (CH), 40.5 (CH$_2$), 48.0 (CH), 78.7 (CH), 180.4 (C) (minor)

Fragrance note: Green, Fruity, Tuberose, Lactone, Tropical, Powerful, Peach

[Example 57] Synthesis of 1-butyl-2H-mintlactone (Exemplary Compound Bu-1ab)

The Exemplary Compound Bu-1aa (100 mg, 0.446 mmol) obtained in Example 56 was stirred under reflux with sodium t-butoxide (100 mg) in toluene, and the post-treatment was performed in accordance with a common method, thereby obtaining 1-butyl-2H-mintlactone isomer (Exemplary Compound Bu-1ab) (58 mg, 58% yield).

Exemplary Compound Bu-1ab: 5-butyl-2H-mintlactone Isomer $^1$H-NMR (500 MHz, CDCl$_3$): δ 0.86-0.94 (3H, m), 0.97 (3H, s), 1.21 (3H, d, J=6.9 Hz), 1.24-1.48 (10H, m), 1.48-

1.53 (1H, m), 1.75-1.87 (1H, m), 1.96 (1H, ddd, J=11.8, 3.9, 1.5 Hz), 2.23-2.31 (1H, m), 3.91-3.98 (1H, m) (major)

$^1$H-NMR (500 MHz, CDCl$_3$): δ 0.86-0.94 (3H, m), 0.97 (3H, s), 1.21-1.53 (13H, m), 1.58-1.65 (1H, m), 1.75-1.87 (1H, m), 2.10 (1H, ddd, J=12.0, 3.6, 1.8 Hz), 2.23-2.31 (1H, m), 3.85-3.93 (1H, m) (minor)

$^{13}$C-NMR (125 MHz, CDCl$_3$): 12.6 (CH$_3$), 14.1 (CH$_3$), 23.4 (CH$_2$), 23.6 (CH$_3$), 25.4 (CH$_2$), 25.7 (CH$_2$), 35.5 (C), 37.3 (CH$_2$), 40.7 (CH$_2$), 41.4 (CH), 45.9 (CH$_2$), 52.5 (CH), 80.4 (CH), 179.6 (C) (major)

$^{13}$C-NMR (125 MHz, CDCl$_3$): 12.6 (CH$_3$), 14.1 (CH$_3$), 23.4 (CH$_2$), 23.5 (CH$_2$), 25.7 (CH$_2$), 29.5 (CH$_3$), 35.4 (C), 37.0 (CH$_2$), 37.3 (CH$_2$), 37.9 (CH$_2$), 40.1 (CH$_2$), 52.3 (CH), 79.8 (CH), 179.6 (C) (minor)

Fragrance note: Green, Fruity, Tuberose, Lactone, Tropical, Powerful, Peach

[Example 58] Synthesis of Optically Active 1-butyl-2H-mintlactone (Exemplary Compound Bu1-be)

Optically active 1-butyl-2H-mintlactone (0.361 g, 74% yield) was obtained as Exemplary Compound Bu1-be in the same manner as in Example 56 except that optically active 5-butyl paramenthane-3,9-diol (0.500 g, 2.19 mmol) obtained in Example 45 was used instead of 1-butyl paramenthane 3,9-diol.

Exemplary Compound Bu1-be: Optically Active 1-butyl-2H-mintlactone $^1$H-NMR (500 MHz, CDCl$_3$): δ 0.85-0.95 (3H, m), 0.96 (3H, s), 1.18 (3H, d, J=7.5 Hz), 1.27-1.53 (10H, m), 1.58-1.68 (1H, m), 1.85-1.93 (1H, m), 1.97-2.04 (1H, m), 2.63 (1H, qui, J=7.5 Hz), 4.19 (1H, td, J=11.5, 4.0 Hz) (major)

$^1$H-NMR (500 MHz, CDCl$_3$): δ 0.86-0.95 (3H, m), 0.96 (3H, s), 1.17 (3H, d, J 7.8 Hz), 1.27-1.53 (10H, m), 1.58-1.68 (1H, m), 1.85-1.93 (1H, m), 2.11-2.16 (1H, m), 2.63 (1H, qui, J=7.6 Hz), 4.12 (1H, td, J=11.5, 3.8 Hz) (minor)

$^{13}$C-NMR (125 MHz, CDCl$_3$): 9.6 (CH$_3$), 14.1 (CH$_3$), 20.8 (CH$_2$), 23.4 (CH$_2$), 23.6 (CH$_3$), 25.4 (CH$_2$), 35.4 (C), 37.3 (CH$_2$), 38.9 (CH), 41.2 (CH$_2$), 46.0 (CH$_2$), 48.2 (CH), 79.3 (CH), 180.4 (C) (major)

$^{13}$C-NMR (125 MHz, CDCl$_3$): 9.6 (CH$_3$), 14.1 (CH$_3$), 20.6 (CH$_2$), 23.5 (CH$_2$), 25.7 (CH$_2$), 29.6 (CH$_3$), 35.3 (C), 37.0 (CH$_2$), 37.8 (CH$_2$), 38.9 (CH), 40.5 (CH$_2$), 48.0 (CH), 78.7 (CH), 180.4 (C) (minor)

Major isomer: 56.1% e.e.
Minor isomer: 79.7% e.e.
Fragrance note: Balsamic, Creamy, Lactonic

[Example 59] Synthesis of Optically Active 1-butyl-2H-mintlactone (Exemplary Compound Bu-1ce)

Optically active 1-butyl-2H-mintlactone (1.59 g, 90% yield) was obtained as Exemplary Compound Bu-1ce in the same manner as in Example 56 except that optically active 1-butyl paramenthane 3,9-diol (1.80 g, 7.88 mmol) obtained in Example 46 was used instead of 1-butyl paramenthane 3,9-diol.

Exemplary Compound Bu-1ce: Optically Active 1-butyl-2H-mintlactone $^1$H-NMR (500 MHz, CDCl$_3$): 0.86-0.95 (3H, m), 0.96 (3H, s), 1.18 (3H, d, J=7.7 Hz), 1.27-1.53 (10H, m), 1.58-1.68 (1H, m), 1.85-1.93 (1H, m), 1.97-2.04 (1H, m), 2.63 (1H, qui, J=7.6 Hz) 4.19 (1H, td, J=11.5, 4.0 Hz) (major)

$^1$H-NMR (500 MHz, CDCl$_3$): δ 0.86-0.95 (3H, m), 0.96 (3H, s), 1.17 (3H, d, J 7.8 Hz), 1.27-1.53 (10H, m), 1.58-1.68 (1H, m), 1.85-1.93 (1H, m), 2.11-2.16 (1H, m), 2.63 (1H, qui, J=7.6 Hz), 4.12 (1H, td, J=11.6, 3.8 Hz) (minor)

$^{13}$C-NMR (125 MHz, CDCl$_3$): 9.6 (CH$_3$), 14.1 (CH$_3$), 20.8 (CH$_2$), 23.4 (CH$_2$), 23.6 (CH$_3$), 25.4 (CH$_2$), 35.4 (C), 37.3 (CH$_2$), 38.9 (CH), 41.2 (CH$_2$), 46.0 (CH$_2$), 48.2 (CH), 79.3 (CH), 180.4 (C) (major)

$^{13}$C-NMR (125 MHz, CDCl$_3$): 9.6 (CH$_3$), 14.1 (CH$_3$), 20.6 (CH$_2$), 23.5 (CH$_2$), 25.7 (CH$_2$), 29.6 (CH$_3$), 35.3 (C), 37.0 (CH$_2$), 37.8 (CH$_2$), 38.9 (CH), 40.5 (CH$_2$) 48.0 (CH), 78.7 (CH), 180.4 (C) (minor)

Major isomer: 54.3% e.e.
Minor isomer: 79.0% e.e.
Fragrance note: Floral, Tuberose, Sweet, Tonka

[Example 60] Synthesis of 1-butyl-2H-mintlactone Isomer (Exemplary Compound Bu-1af)

1-butyl-2H-mintlactone isomer (140 mg, 51% yield) was obtained as Exemplary Compound Bu-1af in the same manner as in Example 56 except that 1-butyl paramenthane 3,9-diol (280 mg, 1.23 mmol) obtained in Example 47 was used instead of 1-butyl paramenthane 3,9-diol.

Exemplary Compound Bu-1af: 1-butyl-2H-mintlactone Isomer $^1$H-NMR (500 MHz, CDCl$_3$): δ 0.92 (3H, t, J=7.1 Hz), 0.96 (3H, s), 1.17 (3H, d, J=7.7 Hz), 1.19-1.35 (8H, m), 1.36-1.49 (2H, m), 1.58-1.68 (2H, m), 1.85-1.93 (1H, m), 2.10-2.16 (1H, m), 2.63 (1H, qui, J=7.6 Hz), 4.12 (1H, td, J=11.5, 3.8 Hz)

$^{13}$C-NMR (125 MHz, CDCl$_3$): 9.6 (CH3), 14.1 (CH3), 20.6 (CH2), 23.5 (CH2), 25.7 (CH2), 29.6 (CH3), 35.3 (C), 37.0 (CH2), 37.8 (CH), 38.8 (CH), 40.5 (CH2), 48.0 (CH), 78.7 (CH), 180.4 (C)

Fragrance note: Tonka, Balsamic, Coumarin, Sweet

[Example 61] Synthesis of 1-butyl-2H-mintlactone Isomer (Exemplary Compound Bu-1ae)

Exemplary Compound Bu-1aa (312 mg, 1.56 mmol) obtained in Example 56 was isolated and purified with column chromatography, thereby obtaining 1-butyl-2H-mintlactone isomer (21 mg, 7% yield) as Exemplary Compound Bu-1ae.

Exemplary Compound Bu-1ae: 1-butyl-2H-mintlactone Isomer $^1$H-NMR (500 MHz, CDCl$_3$): δ 0.92 (3H, t, J=7.0 Hz), 0.96 (3H, s), 1.17 (3H, d, J=7.9 Hz), 1.25-1.53 (10H, m), 1.60-1.69 (1H, m), 1.85-1.93 (1H, m), 1.97-2.10 (1H, m), 2.63 (1H, qui, J=7.5 Hz), 4.19 (1H, td, J=11.1, 3.8 Hz)

$^{13}$C-NMR (125 MHz, CDCl$_3$): 9.6 (CH3), 14.1 (CH3), 20.8 (CH2), 23.5 (CH2), 23.6 (CH3), 25.5 (CH2), 35.4 (C), 37.3 (CH2), 38.9 (CH), 41.2 (CH2), 45.9 (CH2), 48.2 (CH), 79.3 (CH), 180.4 (C)

Fragrance note: Floral, Lactone, Sweet

[Example 62] Synthesis of 1-butyl-2H-mintlactone Isomer (Exemplary Compound Bu-1ad)

Potassium t-butoxide (100 mg, 1.0 eq.) was added to the 1-butyl-2H-mintlactone isomer (Exemplary Compound Bu-1af) (200 mg, 0.892 mmol) obtained in Example 60, and the mixture was heated and stirred at 150° C. for 8 hours. The reaction solution was dissolved in toluene and washed with tap water, and then the oil layer was dried with anhydrous magnesium sulfate, followed by concentration and filtration, thereby obtaining 1-butyl-2H-mintlactone isomer (145 mg, 73% yield) as Exemplary Compound Bu-1ad.

Exemplary Compound Bu-1ad:
1-butyl-2H-mintlactone Isomer $^1$H-NMR (500 MHz, CDCl$_3$): δ 0.92 (3H, t, J=7.1 Hz), 0.96 (3H, s), 1.19-1.35 (10H, m), 1.35-1.50 (3H, m), 1.55-1.67 (1H, m), 1.74-1.81 (1H, m), 2.10 (1H, ddd, J=12.1, 3.7, 1.7 Hz), 2.23-2.31 (1H, m), 3.88 (1H, ddd, J=12.2, 10.3, 3.9 Hz)
$^{13}$C-NMR (125 MHz, CDCl$_3$): 12.6 (CH3), 14.1 (CH3), 23.4 (CH2), 23.5 (CH2), 25.7 (CH2), 29.6 (CH3), 35.5 (C), 37.0 (CH2), 37.9 (CH2), 40.5 (CH2), 41.4 (CH), 52.3 (CH), 79.8 (CH), 179.6 (C)
Fragrance note: Fluor, Fruity, Orris.

[Example 63] Synthesis of 1-butyl-2H-mintlactone Isomer (Exemplary Compound Bu-1ac)

1-butyl-2H-mintlactone isomer (32 mg, 64% yield) was obtained as Exemplary Compound Bu-1ac in the same manner as in Example 62 except that the 1-butyl-2H-mintlactone isomer (Exemplary Compound Bu-1ae) (50 mg, 0.223 mmol) obtained in Example 61 was used instead of 1-butyl-2H-mintlactone isomer (Exemplary Compound Bu-1af).

Exemplary Compound Bu-1ac:
1-butyl-2H-mintlactone Isomer $^1$H-NMR (500 MHz, CDCl$_3$): δ 0.91 (3H, t, J=7.0 Hz), 0.97 (3H, s), 1.21 (3H, d, J=7.0 Hz), 1.24-1.46 (10H, m), 1.48-1.53 (1H, m), 1.79-1.83 (1H, m), 1.97 (1H, ddd, J=12.0, 4.0, 1.5 Hz), 2.22-2.31 (1H, m), 3.91-3.98 (1H, m)
$^{13}$C-NMR (125 MHz, CDCl$_3$): 12.6 (CH3), 14.1 (CH3), 23.5 (CH2), 23.6 (CH2), 23.6 (CH3), 25.5 (CH2), 35.6 (C), 37.4 (CH2), 40.7 (CH2), 41.4 (CH), 45.9 (CH2), 52.5 (CH), 80.4 (CH), 179.7 (C)
Fragrance note: Floral, Sweet, Jasmin, Tuberose.

Example 64

When Exemplary Compounds Bu-1ac, Bu-1ad, Bu-1ae, and Bu-1 af were mixed, and the fragrance note of the mixture was confirmed, the same fragrance note as that of the compound Bu-1aa obtained in Example 56 was obtained.

[Example 65] Synthesis of Optically Active 1-butyl-2H-mintlactone (Exemplary Compound Bu-1bf)

Optically active 1-butyl-2H-mintlactone isomer (102 mg, 68% yield) was obtained as Exemplary Compound Bu-1bf in the same manner as in Example 62 except that the optically active 1-butyl-2H-mintlactone (Exemplary Compound Bu1-be) (150 mg, 0.669 mmol) obtained in Example 58 was used instead of 1-butyl-2H-mintlactone isomer (Exemplary Compound Bu-1af).

Exemplary Compound Bu-1bf: Optically Active 1-butyl-2H-mintlactone $^1$H-NMR (500 MHz, CDCl$_3$): 0.91 (3H, t, J=7.0 Hz), 0.97 (3H, s), 1.21 (3H, d, J=7.0 Hz), 1.24-1.46 (10H, m), 1.48-1.53 (1H, m), 1.79-1.83 (1H, m), 1.97 (1H, ddd, J=12.0, 4.0, 1.5 Hz), 2.22-2.31 (1H m), 3.91-3.98 (1H, m) (major)
$^1$H-NMR (500 MHz, CDCl$_3$): δ 0.92 (3H, t, J=7.1 Hz), 0.96 (3H, s), 1.19-1.35 (10H, m), 1.35-1.50 (3H, m), 1.55-1.67 (1H, m), 1.74-1.81 (1H, m), 2.07-2.14 (1H, m), 2.23-2.31 (1H, m), 3.85-3.92 (1H, m) (minor)
$^{13}$C-NMR (125 MHz, CDCl$_3$): 12.6 (CH3), 14.1 (CH3), 23.5 (CH2), 23.6 (CH2), 23.6 (CH3), 25.5 (CH2), 35.6 (C), 37.4 (CH2), 40.7 (CH2), 41.4 (CH), 45.9 (CH2), 52.5 (CH), 80.4 (CH), 179.7 (C) (major)
$^{13}$C-NMR (125 MHz, CDCl$_3$): 12.6 (CH3), 14.1 (CH3), 23.5 (CH2), 23.6 (CH2), 23.6 (CH3), 25.5 (CH2), 35.6 (C), 37.4 (CH2), 40.7 (CH2), 41.4 (CH), 45.9 (CH2), 52.5 (CH), 80.4 (CH), 179.7 (C) (minor)
Major isomer: 60.5% e.e.
Minor isomer: 80.8% e.e.
Fragrance note: Nutty, Lactone.

[Example 66] Synthesis of Optically Active 1-butyl-2H-mintlactone (Exemplary Compound Bu-1cf)

Optically active 1-butyl-2H-mintlactone isomer (281 mg, 94% yield) was obtained as Exemplary Compound Bu-1cf in the same manner as in Example 62 except that optically active 1-butyl-2H-mintlactone (Exemplary Compound Bu-1ce) (300 mg, 1.34 mmol) obtained in Example 59 was used instead of 1-butyl-2H-mintlactone isomer (Exemplary Compound Bu-1af).

Exemplary Compound Bu-1cf: Optically Active 1-butyl-2H-mintlactone $^1$H-NMR (500 MHz, CDCl$_3$): δ 0.92 (3H, t, J=7.0 Hz), 0.97 (3H, s), 1.21 (3H, d, J=7.0 Hz), 1.24-1.46 (10H, m), 1.48-1.53 (1H, m), 1.79-1.83 (1H, m), 1.97 (1H, ddd, J=12.0, 4.0, 1.5 Hz), 2.22-2.31 (1H, m), 3.91-3.98 (1H, m) (major)
$^1$H-NMR (500 MHz, CDCl$_3$): δ 0.92 (3H, t, J=7.1 Hz), 0.96 (3H, s), 1.19-1.35 (10H, m), 1.35-1.50 (3H, m), 1.55-1.67 (1H, m), 1.74-1.81 (1H, m), 2.07-2.14 (1H, m), 2.22-2.31 (1H, m), 3.85-3.92 (1H, m) (minor)
$^{13}$C-NMR (125 MHz, CDCl$_3$): 12.6 (CH3), 14.1 (CH3), 23.5 (CH2), 23.6 (CH2), 23.6 (CH3), 25.5 (CH2), 35.6 (C), 37.4 (CH2), 40.7 (CH2), 41.4 (CH), 45.9 (CH2), 52.5 (CH), 80.4 (CH) 179.7 (C) (major)
$^{13}$C-NMR (125 MHz, CDCl$_3$): 12.6 (CH3), 14.1 (CH3), 23.5 (CH2), 23.6 (CH2), 23.6 (CH3), 25.5 (CH2), 35.6 (C), 37.4 (CH2), 40.7 (CH2), 41.4 (CH), 45.9 (CH2), 52.5 (CH), 80.4 (CH), 179.7 (C) (minor)
Major isomer: 57.5% e.e.
Minor isomer: 79.8% e.e.
Fragrance note: Floral, Sweet.

[Example 67] Synthesis of 1-methyl-2H-mintlactone (Exemplary Compound Me-1a)

1-methyl-2H-mintlactone (694 mg, 3.81 mmol, 71% yield) was obtained as Exemplary Compound Me-1a in the same manner as in Example 56 except that 1-methylparamenthane 3,9-diol (1.00 g, 5.37 mmol) obtained in Example 37 was used instead of 1-butyl paramenthane 3,9-diol.

Exemplary Compound Me-1a:
1-methyl-2H-mintlactone $^1$H-NMR (500 MHz, CDCl$_3$): 0.99 (3H, s), 1.04 (3H, s), 1.17 (3H, d, J=7.7 Hz), 1.27-1.55 (4H, m), 1.62-1.67 (1H, m), 1.84-1.92 (1H, m), 1.99 (1H, ddd, J=11.8, 3.9, 1.7 Hz), 2.63 (1H, qui, J=7.6 Hz), 4.17 (1H, td, J=11.4, 3.9 Hz) (major)

$^1$H-NMR (500 MHz, CDCl$_3$): δ 1.00 (3H, s), 1.04 (3H, s), 1.21 (3H, d, J=6.9 Hz), 1.27-1.55 (4H, m), 1.62-1.67 (1H, m), 1.81-1.90 (1H, m), 1.94-1.98 (1H, m), 2.24-2.31 (1H, m), 3.91-3.97 (1H, m) (minor)

$^{13}$C-NMR (125 MHz, CDCl$_3$): 9.6 (CH$_3$), 21.0 (CH$_2$) 26.0 (CH$_3$), 32.8 (C), 33.1 (CH$_3$), 38.80 (CH$_2$), 38.80 (CH), 43.0 (CH$_2$), 48.0 (CH), 79.2 (CH), 180.3 (C) (major)

$^{13}$C-NMR (125 MHz, CDCl$_3$): 12.5 (CH$_3$), 23.8 (CH$_2$), 26.0 (CH$_3$), 32.9 (C), 33.1 (CH$_3$), 38.8 (CH$_2$), 41.3 (CH), 42.5 (CH$_2$), 52.3 (CH), 80.2 (CH), 179.6 (C) (major)

Fragrance note: Coumarine, Balsamic, White Floral, Lactone, Tuberose, Tonka

[Example 68] Synthesis of (1R,2S)-5-methyl-2H-mintlactone (Exemplary Compound Me-1b)

(1R,2S)-1-methyl-2H-mintlactone (1.327 g, 7.28 mmol, 90% yield) was obtained as Exemplary Compound Me-1b in the same manner as in Example 56 except that (1R,2S)-1-methylparamenthane 3,9-diol (1.50 g, 8.05 mmol) obtained in Example 38 was used instead of 1-butyl paramenthane 3,9-diol.

Exemplary Compound Me-1b:
(1R,2S)-1-methyl-2H-mintlactone $^1$H-NMR (500 MHz, CDCl$_3$): δ 0.99 (3H, s), 1.04 (3H, s), 1.17 (3H, d, J=7.7 Hz), 1.27-1.55 (4H, m), 1.62-1.67 (1H, m), 1.84-1.92 (1H, m), 1.99 (1H, ddd, J=11.7, 3.9, 1.7 Hz), 2.63 (1H, qui, J=7.6 Hz), 4.17 (1H, td, J=11.4, 3.9 Hz) (major)

$^1$H-NMR (500 MHz, CDCl$_3$): δ 1.00 (3H, s), 1.04 (3H, s), 1.21 (3H, d, J=6.9 Hz), 1.27-1.55 (4H, m), 1.62-1.67 (1H, m), 1.81-1.90 (1H, m), 1.94-1.98 (1H, m), 2.24-2.31 (1H, m), 3.91-3.97 (1H, m) (minor)

$^{13}$C-NMR (125 MHz, CDCl$_3$): 9.6 (CH$_3$), 21.0 (CH$_2$) 26.0 (CH$_3$), 32.8 (C), 33.1 (CH$_3$), 38.78 (CH$_2$), 38.81 (CH), 43.0 (CH$_2$), 48.0 (CH), 79.1 (CH), 180.3 (C) (major)

$^{13}$C-NMR (125 MHz, CDCl$_3$): 12.5 (CH$_3$), 23.8 (CH$_2$), 26.0 (CH$_3$), 32.9 (C), 33.1 (CH$_3$), 38.8 (CH$_2$), 41.3 (CH), 42.5 (CH$_2$), 52.3 (CH), 80.2 (CH), 179.6 (C) (major)

Fragrance note: Coumarine, Balsamic, White Floral, Lactone, Tuberose, Tonka

[Example 69] Synthesis of (1S,2R)-1-methyl-2H-mintlactone (Exemplary Compound Me-1c)

(1S,2R)-1-methyl-2H-mintlactone (1.192 g, 6.54 mmol, 81% yield) was obtained as Exemplary Compound Me-1c in the same manner as in Example 56 except that (1S,2R)-1-methylparamenthane 3,9-diol (1.50 g, 8.05 mmol) obtained in Examples 39 was used instead of 1-butyl paramenthane 3,9-diol.

Exemplary Compound Me-1c:
(1S,2R)-1-methyl-2H-mintlactone $^1$H-NMR (500 MHz, CDCl$_3$): δ 0.99 (3H, s), 1.04 (3H, s), 1.17 (3H, d, J=7.7 Hz), 1.27-1.55 (4H, m), 1.62-1.67 (1H, m), 1.84-1.92 (1H, m), 1.99 (1H, ddd, J=11.7, 3.9, 1.7 Hz), 2.63 (1H, qui, J=7.7 Hz), 4.17 (1H, td, J=11.4, 3.9 Hz) (major)

$^1$H-NMR (500 MHz, CDCl$_3$): δ 1.00 (3H, s), 1.04 (3H, s), 1.20 (3H, d, J=7.0 Hz), 1.27-1.55 (4H, m), 1.62-1.67 (1H, m), 1.81-1.90 (1H, m), 1.94-1.98 (1H, m), 2.28 (1H, qui, J=7.7 Hz), 3.91-3.96 (1H, m) (minor)

$^{13}$C-NMR (125 MHz, CDCl$_3$): 9.6 (CH$_3$), 21.0 (CH$_2$), 26.0 (CH$_3$), 32.8 (C), 33.1 (CH$_3$), 38.79 (CH$_2$), 38.81 (CH), 43.0 (CH$_2$), 48.0 (CH), 79.2 ((CH), 180.3 (C) (major)

$^{13}$C-NMR (125 MHz, CDCl$_3$): 12.5 (CH$_3$), 23.8 (CH$_2$), 26.0 (CH$_3$), 32.9 (C), 33.1 (CH$_3$), 38.8 (CH$_2$), 41.5 (CH), 42.5 (CH$_2$), 52.3 (CH), 80.3 (CH), 179.6 (C) (major)

Fragrance note: Coumarine, Balsamic, White Floral, Lactone, Tuberose, Tonka

[Example 70] Synthesis of 1-ethyl-2H-mintlactone (Exemplary Compound Et-1a)

1-ethyl-2H-mintlactone (1.17 g, 6.09 mmol, 61% yield) was obtained as Exemplary Compound Et-1a in the same manner as in Example 56 except that 1-ethylparamenthane 3,9-diol (2.00 g, 9.98 mmol) obtained in Example 40 was used instead of 1-butyl paramenthane 3,9-diol.

Exemplary Compound Et-1a:
t-ethyl-2H-mintlactone $^1$H-NMR (500 MHz, CDCl$_3$): δ 0.86 (3H, t, J=7.7 Hz), 0.95 (3H, s), 1.16 (3H, d, J=7.7 Hz), 1.20-2.34 (9H, m), 2.59-2.67 (1H, m), 4.19 (1H, td, J=11.3, 4.0 Hz) (major)

$^1$H-NMR (500 MHz, CDCl$_3$): 0.85 (3H, t, J=7.7 Hz), 0.95 (3H, s), 1.16 (3H, d, J=7.7 Hz), 1.20-2.34 (9H, m), 2.59-2.67 (1H, m), 4.11 (1H, td, J=11.5, 3.9 Hz) (minor)

$^{13}$C-NMR (125 MHz, CDCl$_3$): 7.6 (CH$_3$), 9.6 (CH$_3$), 20.7 (CH$_2$), 23.0 (CH$_3$), 35.5 (C), 36.7 (CH$_2$), 38.2 (CH$_2$), 38.8 (CH), 40.7 (CH$_2$), 48.2 (CH), 79.7 (CH), 180.3 (C) (major)

$^{13}$C-NMR (125 MHz, CDCl$_3$): 7.8 (CH$_3$), 12.5 (CH$_3$), 20.5 (CH$_2$), 28.8 (CH$_3$), 29.3 (CH$_2$), 35.3 (C), 37.3 (CH$_2$), 40.0 (CH$_2$), 41.3 (CH), 48.0 (CH), 78.6 (CH), 180.3 (C) (minor)

Fragrance note: Floral, Sweet, Nutty, Coumarin

[Example 71] Synthesis of 1-isopropyl-2H-mintlactone (Exemplary Compound iPr-1a)

Desired 1-isopropyl-2H-mintlactone (890 mg, 57% yield) was obtained as Exemplary Compound iPr-1a in the same manner as in Example 56 except that 1-isopropyl paramenthane 3,9-diol (1.60 g, 7.46 mmol) obtained in Example 41 was used instead of 1-butyl paramenthane 3,9-diol.

Exemplary Compound iPr-1a:
1-isopropyl-2H-mintlactone $^1$H-NMR (500 MHz, CDCl$_3$): δ 0.79-0.91 (9H, m), 1.03-1.15 (3H, m), 1.18-1.96 (7H, m), 2.04-2.09 (1H, m), 2.63 (1H, qui, J=7.6 Hz), 4.19 (1H, td, J=11.6, 4.0 Hz) (major)

$^1$H-NMR (500 MHz, CDCl$_3$): δ 0.79-0.91 (9H, m), 1.03-1.15 (3H, m), 1.18-1.96 (8H, m), 2.63 (1H, qui, J=7.6 Hz), 4.15 (1H, td, J=11.5, 3.7 Hz) (minor)

$^{13}$C-NMR (125 MHz, CDCl$_3$): 9.6 (CH$_3$), 16.8 (CH$_3$), 17.0 (CH$_3$), 19.2 (CH$_3$), 20.8 (CH$_2$), 35.2 (CH$_2$), 37.9 (C), 38.8 (CH), 39.3 (CH$_2$), 39.6 (CH), 47.9 (CH), 79.6 (CH), 180.4 (C) (major)

$^{13}$C-NMR (125 MHz, CDCl$_3$): 9.5 (CH$_3$), 16.7 (CH$_3$), 16.9 (CH$_3$), 20.2 (CH$_2$), 23.0 (CH$_3$), 28.6 (CH), 35.9 (CH$_2$), 37.9 (C), 38.9 (CH), 39.8 (CH$_2$), 48.3 (CH), 78.0 (CH), 180.4 (C) (minor)

Fragrance note: White floral, Jasmin, Leathery, Animaric, Fruity

[Example 72] Synthesis of 1-propyl-2H-mintlactone (Exemplary Compound Pr-1a)

1-propyl-2H-mintlactone (1.44 g, 67% yield) was obtained as Exemplary Compound Pr-1a in the same manner as in Example 56 except that 1-propyl paramenthane 3,9-diol (2.22 g, 10.3 mmol) obtained in Example 42 was used instead of 1-butyl paramenthane 3,9-diol.

Exemplary Compound Pr-1a:
1-propyl-2H-mintlactone $^1$H-NMR (500 MHz, CDCl$_3$): 0.85-0.95 (3H, m), 0.96 (3H, s), 1.15 (3H, d, J=9.0 Hz), 1.20-1.54 (8H, m), 1.60-1.69 (1H, m), 1.81-1.93 (1H, m), 2.01 (1H, ddd, J=12.1, 3.7, 1.7 Hz), 2.63 (1H, qui, J=7.5 Hz), 4.18 (1H, td, J=11.5, 4.0 Hz) (major)

$^1$H-NMR (500 MHz, CDCl$_3$): δ 0.85-0.95 (3H, m), 0.97 (3H, s), 1.15 (3H, d, J 9.0 Hz), 1.20-1.54 (8H, m), 1.60-1.69 (1H, m), 1.81-1.93 (1H, m), 2.10-2.07 (1H, m), 2.63 (1H, qui, J=7.5 Hz), 4.15 (1H, td, J=11.5, 3.5 Hz) (minor)

$^{13}$C-NMR (125 MHz, CDCl$_3$): 9.6 (CH3), 14.8 (CH3), 16.4 (CH2), 20.8 (CH2), 23.6 (CH3), 35.5 (C), 37.3 (CH2), 38.9 (CH), 41.2 (CH2), 482 (CH), 48.6 (CH2), 79.3 (CH), 180.4 (C) (major)

$^{13}$C-NMR (125 MHz, CDCl$_3$): 9.6 (CH3), 14.9 (CH3), 16.7 (CH2), 20.6 (CH2), 29.6 (CH3), 35.5 (C), 37.8 (CH2), 38.9 (CH), 39.8 (CH2), 40.6 (CH2), 48.0 (CH), 78.7 (CH), 180.4 (C) (minor)

Fragrance note: Floral, Fruity, Peach, Nutty, Peanuts

[Example 73] Synthesis of 1-iso-butyl-2H-mintlactone (Exemplary Compound iBu-1a)

Desired 1-iso-butyl-2H-mintlactone (1.91 g, 71% yield) was obtained as Exemplary Compound iBu-1a in the same manner as in Example 56 except that 1-iso-butyl paramenthane 3,9-diol (2.73 g, 12.0 mmol) obtained in Example 43 was used instead of 1-butyl paramenthane 3,9-diol.

Exemplary Compound iBu-1a:
1-iso-butyl-2H-mintlactone $^1$H-NMR (500 MHz, CDCl$_3$): δ 0.80-1.04 (9H, m), 1.10-1.24 (3H, m), 1.25-1.93 (9H, m), 2.04 (1H, ddd, J=11.6, 3.9, 1.6 Hz), 2.63 (1H, qui, J=7.7 Hz), 4.18 (1H, td, J=11.5, 4.0 Hz) (diastereomer 1)

$^1$H-NMR (500 MHz, CDCl$_3$): δ 0.80-1.04 (9H, m), 1.10-1.24 (3H, m), 1.25-1.93 (9H, m), 2.16 (1H, ddd, J=12.0, 3.6, 1.9 Hz), 2.63 (1H, qui, J=7.7 Hz), 4.14 (1H, td, J=11.4, 3.6 Hz) (diastereomer 2)

$^1$H-NMR (500 MHz, CDCl$_3$): δ 0.80-1.04 (9H, m), 1.10-1.24 (3H, m), 1.25-1.93 (9H, m), 1.97-2.03 (1H, m), 2.63 (1H, qui, J=7.7 Hz), 4.18 (1H, td, J=11.5, 4.0 Hz) (diastereomer 3)

$^1$H-NMR (500 MHz, CDCl$_3$): δ 0.80-1.04 (9H, m), 1.10-1.24 (3H, m), 1.25-1.93 (9H, m), 2.11-2.17 (1H, m), 2.63 (1H, qui, J=7.7 Hz), 4.14 (1H, td, J=11.4, 3.6 Hz) (diastereomer 4)

Fragrance note: Floral, Fruity, Peach

[Example 74] Synthesis of 1-sec-butyl-2H-mintlactone (Exemplary Compound sBu-1a)

1-sec-butyl-2H-mintlactone (0.258 g, 75% yield) was obtained as Exemplary Compound sBu-1a in the same manner as in Example 56 except that 1-sec-butyl paramenthane 3,9-diol (0.350 g, 1.53 mmol) obtained in Example 44 was used instead of 1-butyl paramenthane 3,9-diol.

Exemplary Compound sBu-1a:
1-sec-butyl-2H-mintlactone $^1$H-NMR (500 MHz, CDCl$_3$): δ 0.80-0.95 (6H, m), 1.05-1.15 (1H, m), 1.15-1.18 (3H, m), 1.25-1.70 (9H, m), 1.81-2.07 (2H, m), 2.01 (1H, ddd, J=11.5, 4.0, 1.5 Hz), 2.63 (1H, qui, J=7.5 Hz), 4.18 (1H, td, J=11.5, 4.0 Hz) (diastereomer 1)

$^1$H-NMR (500 MHz, CDCl$_3$): δ 0.80-0.95 (6H, m), 1.05-1.15 (1H, m), 1.15-1.18 (3H, m), 1.25-1.70 (9H, m), 1.81-2.07 (2H, m), 2.13 (1H, ddd, J=11.5, 4.0, 1.5 Hz), 2.63 (1H, qui, J=7.5 Hz), 4.18 (1H, td, J=11.5, 4.0 Hz) (diastereomer 2)

$^1$H-NMR (500 MHz, CDCl$_3$): δ 0.80-0.95 (6H, m), 1.05-1.15 (1H, m), 1.15-1.18 (3H, m), 1.25-1.70 (9H, m), 1.81-2.07 (2H, m), 2.39 (1H, dt, J=12.5, 2.5 Hz), 2.63 (1H, qui, J=7.5 Hz), 4.07-4.18 (1H, m) (diastereomer 3)

$^1$H-NMR (500 MHz, CDCl$_3$): δ 0.80-0.95 (6H, m), 1.05-1.15 (1H, m), 1.15-1.18 (3H, m), 1.25-1.70 (9H, m), 1.81-2.07 (2H, m), 2.44 (1H, dt, J=12.5, 2.5 Hz), 2.63 (1H, qui, J=7.5 Hz), 4.07-4.18 (1H, m) (diastereomer 4)

Fragrance note: Fruity, Floral, Prune, Dry-fruits

[Example 75] Synthesis of 1-n-pentyl-2H-mintlactone (Exemplary Compound Pe-1a)

1-pentyl-2H-mintlactone (0.367 g, 30% yield) was obtained as Exemplary Compound Pe-1a in the same manner as in Example 56 except that 5-n-pentyl paramenthane-3,9-diol (1.23 g, 5.07 mmol) obtained in Example 48 was used instead of 1-butyl paramenthane 3,9-diol.

Exemplary Compound Pe-1a:
1-pentyl-2H-mintlactone $^1$H-NMR (500 MHz, CDCl$_3$): δ 0.90 (3H, t, J=7.0 Hz), 0.97 (3H, s), 1.21 (3H, d, J=7.0 Hz), 1.22-1.48 (12H, m), 1.58-1.67 (1H, m), 1.75-1.81 (1H, m), 2.10 (1H, ddd, J=12.0, 4.0, 2.0 Hz), 2.22-2.31 (1H, m), 3.88 (1H, ddd, J=12.5, 10.5, 4.0 Hz) (major)

$^{13}$C-NMR (125 MHz, CDCl$_3$): 12.6 (CH3), 14.1 (CH3), 22.7 (CH2), 23.2 (CH2), 23.4 (CH2), 29.6 (CH3), 32.7 (CH2), 35.5 (C), 37.3 (CH2), 37.9 (CH2), 40.1 (CH2), 41.4 (CH), 52.3 (CH), 79.8 (CH), 179.6 (C) (major)

Fragrance note: Fruity, Plastic, Coconuts

[Example 76] Synthesis of 1-(3-pentyl)-2H-mintlactone (Exemplary Compound 3Pe-1a)

Desired 1-(3-pentyl)-2H-mintlactone (212 mg, 0.791 mmol, 58% yield) was obtained as Exemplary Compound 3Pe-1a in the same manner as in Example 56 except that 1-(3-pentyl)paramenthane-3,9-diol (330 mg, 1.36 mmol) obtained in Example 49 was used instead of 1-butyl paramenthane 3,9-diol.

Exemplary Compound 3Pe-1a:
1-(3-pentyl)-2H-mintlactone $^1$H-NMR (500 MHz, CDCl$_3$): δ 0.76-0.84 (1H, m), 0.89-0.97 (9H, m), 1.06-1.15 (3H, m), 1.17 (3H, d, J=7.7 Hz), 1.30-1.70 (6H, m), 1.82-1.89 (1H, m), 2.07 (1H, ddd, J=11.6, 4.0, 1.6 Hz), 2.59-2.67 (1H, m), 4.18 (1H, td, J=11.3, 4.0 Hz) (major)

$^1$H-NMR (500 MHz, CDCl$_3$): δ 0.76-0.84 (1H, m), 0.89-0.97 (9H, m), 1.06-1.15 (3H, m), 1.17 (31, d, J=7.7 Hz), 1.30-1.70 (6H, m), 1.91-2.02 (1H, m), 2.42 (1H, dt, J=12.3, 3.0 Hz), 2.59-2.67 (1H, m), 4.15 (1H, td, J=11.3, 3.6 Hz) (major)

$^{13}$C-NMR (125 MHz, CDCl$_3$): 9.61 (CH3), 14.5 (CH3), 14.6 (CH3), 20.7 (CH2), 21.7 (CH3), 22.8 (CH2), 22.9 (CH2), 35.1 (CH2), 38.9 (C), 39.3 (CH2), 39.4 (C), 48.0 (CH), 54.6 (CH), 79.5 (CH), 180.4 (C) (major)

$^{13}$C-NMR (125 MHz, CDCl$_3$): 13.9 (CH3), 14.5 (CH3), 14.6 (CH3), 20.6 (CH2), 22.3 (CH2), 22.4 (CH2), 25.0 (CH3), 36.6 (CH2), 38.8 (CH), 39.3 (C), 40.2 (CH2), 43.1 (CH), 48.3 (CH), 78.2 (CH), 180.4 (C) (minor)

Fragrance note: Fruity, Peach, Coconuts

[Example 77] Synthesis of 1-n-hexyl-2H-mintlactone (Exemplary Compound Hx-1a)

1-n-hexy-2H-mintlactone (0.400 g, 76% yield) was obtained as Exemplary Compound Hx-1a in the same manner as in Example 56 except that 1-n-hexyl paramenthane-3,9-diol (0.530 g, 2.09 mmol) obtained in Example 50 was used instead of 1-butyl paramenthane 3,9-diol.

Exemplary Compound Hx-1a:
5-hexyl-2H-mintlactone $^1$H-NMR (500 MHz, CDCl$_3$): δ 0.86-0.92 (3H, m), 0.96 (3H, s), 1.16 (3H, d, J 8.0 Hz), 1.20-1.68 (15H, m), 1.84-1.94 (1H, m), 2.00 (1H, ddd, J=12.0, 4.0, 1.5 Hz), 2.63 (1H, qui, J=8.0 Hz), 4.18 (1H, td, J=11.5, 4.0 Hz) (major)

$^1$H-NMR (500 MHz, CDCl$_3$): δ 0.86-0.92 (3H, m), 0.96 (3H, s), 1.16 (3H, d, J 8.0 Hz), 1.20-1.68 (15H, m), 1.84-1.94 (1H, m), 2.11-2.15 (1H, m), 2.10-2.07 (1H, m), 2.63 (1H, qui, J=8.0 Hz), 4.12 (1H, td, J=12.0, 4.0 Hz) (minor)

$^{13}$C-NMR (125 MHz, CDCl$_3$): 9.7 (CH3), 14.1 (CH3), 20.8 (CH2), 22.7 (CH2), 23.2 (CH2), 23.6 (CH3), 30.1 (CH2), 31.9 (CH2), 35.5 (C), 37.3 (CH2), 38.9 (CH), 41.2 (CH2), 46.2 (CH2), 48.2 (CH), 79.3 (CH), 180.4 (C) (major)

$^{13}$C-NMR (125 MHz, CDCl$_4$): 9.7 (CH3), 14.1 (CH3), 20.7 (CH2), 22.7 (CH2), 23.5 (CH2), 29.6 (CH3), 30.1 (CH2), 31.9 (CH2), 35.4 (C), 37.8 (CH2), 38.9 (CH), 40.5 (CH2), 46.2 (CH2), 48.0 (CH), 78.7 (CH), 180.4 (C) (minor)

Fragrance note: Sweet, Coumarin

[Example 78] Synthesis of 1-cyclohexyl-2H-mintlactone (Exemplary Compound Cy-1a)

1-cyclohexyl-2H-mintlactone (0.400 g, 76% yield) was obtained as Exemplary Compound Cy-1a in the same manner as in Example 56 except that 1-cyclohexyl paramenthane-3,9-diol (3.00 g, 2.09 mmol) obtained in Example 51 was used instead of 1-butyl paramenthane 3,9-diol.

Exemplary Compound Cy-1a:
1-cyclohexyl-2H-mintlactone (047-012CyL)

$^1$H-NMR (500 MHz, CDCl$_3$): δ 0.90 (3H, s), 0.95-1.38 (12H, m), 1.44 (1H, qd, J=12.6, 3.5 Hz), 1.55-1.61 (1H, br), 1.62-1.90 (6H, m), 2.08 (i H, dd, J=11.6, 2.5 Hz), 2.63 (1H, qui, J=7.7 Hz), 4.19 (1H, td, J=11.5, 4.0 Hz) (major)

$^1$H-NMR (500 MHz, CDCl$_3$): δ 0.84 (3H, s), 0.95-1.38 (12H, m), 1.44 (1H, qd, J=12.6, 3.5 Hz), 1.55-1.61 (1H, br), 1.62-1.90 (6H, m), 2.37-2.43 (1H, br), 2.63 (1H, qui, J=7.7 Hz), 4.12 (1H, td, J=11.6, 3.5 Hz) (minor)

$^{13}$C-NMR (125 MHz, CDCl$_3$): 9.6 (CH3), 20.2 (CH3), 20.8 (CH2), 26.68 (CH2), 26.71 (CH2), 26.8 (CH2), 27.1 (CH2×2), 35.3 (CH2), 37.9 (C), 38.9 (CH), 39.6 (CH2), 48.0 (CH), 50.6 (CH), 79.7 (CH), 180.4 (C) (major)

$^{13}$C-NMR (125 MHz, CDCl$_3$): 9.6 (CH3), 20.3 (CH2), 24.9 (CH3), 26.4 (CH2), 26.5 (CH2), 27.1 (CH2), 27.17 (CH2), 27.20 (CH2), 35.6 (CH2), 38.0 (C), 38.9 (CH), 39.4 (CH2), 39.5 (CH), 48.4 (CH), 78.0 (CH), 180.4 (C) (minor)

Fragrance note: Floral, Fruity, Lactone, sweet

[Example 79] Synthesis of 1-n-heptyl-2H-mintlactone (Exemplary Compound Hp-1a)

1-n-heptyl-2H-mintlactone (0.367 g, 30% yield) was obtained as Exemplary Compound Hp-1a in the same manner as in Example 56 except that 1-n-heptyl paramenthane-3,9-diol (1.23 g, 5.07 mmol) obtained in Example 52 was used instead of 1-butyl paramenthane 3,9-diol.

Exemplary Compound Hp-1a:
1-n-heptyl-2H-mintlactone $^1$H-NMR (500 MHz, CDCl$_3$): δ 0.87-0.92 (3H, m), 0.96 (3H, s), 1.17 (3H, d, J 7.7 Hz), 1.20-1.70 (17H, m), 1.83-1.94 (1H, m), 2.00 (1H, ddd, J=11.7, 3.8, 1.3 Hz), 2.63 (1H, qui, J=7.7 Hz), 4.18 (1H, td, J=11.5, 3.9 Hz) (major)

$^1$H-NMR (500 MHz, CDCl$_3$): δ 0.87-0.92 (3H, m), 0.96 (3H, s), 1.16 (3H, d, J=7.7 Hz), 1.20-1.70 (17H, m), 1.83-1.94 (1H, m), 2.10-2.15 (1H, m), 2.63 (1H, qui, J=7.7 Hz), 4.12 (1H, td, J=11.6, 3.9 Hz) (minor)

$^{13}$C-NMR (125 MHz, CDCl$_3$): 9.7 (CH3), 14.1 (CH3), 20.8 (CH2), 22.7 (CH2), 23.2 (CH2), 23.6 (CH3), 29.3 (CH2), 30.4 (CH2), 31.9 (CH2), 35.5 (C), 37.3 (CH2), 38.9 (CH), 41.2 (CH2), 46.2 (CH2), 48.2 (CH), 79.3 (CH), 180.4 (C) (major)

$^{13}$C-NMR (125 MHz, CDCl$_3$): 9.7 (CH3), 14.1 (CH3), 20.6 (CH2), 22.7 (CH2), 23.5 (CH2), 29.3 (CH2), 29.6 (CH3), 30.4 (CH2), 31.9 (CH2), 35.4 (C), 37.3 (CH2), 37.8 (CH2), 38.9 (CH), 40.5 (CH2), 48.0 (CH), 78.7 (CH), 180.4 (C) (minor)

Fragrance note: Fruity, Honey, Rose

[Example 80] Synthesis of 1-n-octyl-2H-mintlactone (Exemplary Compound Oc-1a)

1-n-octyl-2H-mintlactone (0.530 g, 39% yield) was obtained as Exemplary Compound Oc-1a in the same manner as in Example 56 except that 1-n-octyl paramenthane-3,9-diol (1.37 g, 4.816 mmol) obtained in Example 53 was used instead of 1-butyl paramenthane 3,9-diol.

Exemplary Compound Oc-1a:
1-n-octyl-2H-mintlactone $^1$H-NMR (500 MHz, CDCl$_3$): δ 0.85-0.92 (6H, m), 0.96 (3H, s), 1.17 (3H, d, J=7.7 Hz), 1.20-1.95 (17H, m), 1.97-2.03 (1H, m), 2.63 (1H, qui, J=7.6 Hz), 4.18 (1H, td, J=11.5, 4.0 Hz) (major)

$^1$H-NMR (500 MHz, CDCl$_3$): δ 0.85-0.92 (6H, m), 0.96 (3H, s), 1.17 (3H, d, J 7.7 Hz), 1.20-1.95 (17H, m), 2.10-2.16 (1H, m), 2.63 (1H, qui, J=7.6 Hz), 4.12 (1H, td, J=11.6, 3.8 Hz) (minor)

$^{13}$C-NMR (125 MHz, CDCl$_3$): 9.6 (CH3), 14.1 (CH3), 20.8 (CH2), 22.7 (CH2), 23.2 (CH2), 23.6 (CH3), 29.3 (CH2), 29.6 (CH2), 30.5 (CH2), 31.9 (CH2), 35.5 (C), 37.3 (CH2), 38.9 (CH), 41.2 (CH2), 46.2 (CH2), 48.2 (CH), 79.3 (CH), 180.4 (C) (major)

$^{13}$C-NMR (125 MHz, CDCl$_3$): 9.7 (CH3), 14.1 (CH3), 20.6 (CH2), 22.7 (CH2), 23.5 (CH2), 29.3 (CH2), 29.6 (CH2), 29.6 (CH3), 30.4 (CH2), 31.9 (CH2), 35.4 (C), 37.3 (CH2), 37.8 (CH2), 38.9 (CH), 40.5 (CH2), 48.0 (CH), 78.7 (CH), 180.4 (C) (minor)

Fragrance note: Cinnamon, Honey, Apple

[Example 81] Synthesis of 1-phenyl-2H-mintlactone (Exemplary Compound Ph-1a)

1-phenyl-2H-mintlactone (531 mg, 2.177 mmol, 68% yield) was obtained as Exemplary Compound Ph-1a in the same manner as in Example 56 except that 1-phenyl paramenthane-3,9-diol (800 mg, 3.223 mmol) obtained in Example 54 was used instead of 1-butyl paramenthane 3,9-diol.

Exemplary Compound Ph-1a: 1-phenyl-2H-mintlactone $^1$H-NMR (500 MHz, CDCl$_3$): δ 0.96 (3H, d, J=7.7 Hz), 1.26 (3H, s), 1.40-2.14 (5H, m), 2.51-2.57 (1H, m), 2.61 (1H, qui, J=7.6 Hz), 2.93 (1H, dt, J=12.4, 3.0 Hz), 3.86 (1H, td, J=11.8, 3.3 Hz), 7.19-7.25 (1H, m), 7.32-7.40 (4H, m) (major)

$^1$H-NMR (500 MHz, CDCl$_3$): δ 1.23 (3H, d, J=7.7 Hz), 1.37 (3H, s), 1.40-2.14 (6H, m), 2.45-2.49 (1H, m), 2.70 (1H, qui, J=7.6 Hz), 4.38 (1H, td, J=11.6, 3.9 Hz), 7.19-7.25 (1H, m), 7.32-7.40 (4H, m) (minor)

$^{13}$C-NMR (125 MHz, CDCl$_3$): 9.5 (CH$_3$), 21.5 (CH$_2$), 35.2 (CH$_3$), 36.9 (CH$_2$), 38.8 (CH), 40.6 (C), 41.8 (CH$_2$), 48.1 (CH), 78.6 (CH), 125.6 (2C, CH), 126.1 (CH), 128.8 (2C, CH), 145.9 (C), 180.1 (C) (major)

$^{13}$C-NMR (125 MHz, CDCl$_3$): 9.7 (CH$_3$), 21.1 (CH$_2$), 26.2 (CH$_3$), 37.5 (CH$_2$), 38.8 (CH), 39.4 (C), 41.5 (CH$_2$), 47.9 (CH), 79.2 (CH), 124.8 (2C, CH), 126.2 (CH), 128.4 (2C, CH), 150.3 (C), 180.1 (C) (minor)

Fragrance note: Floral, Fruity

[Example 82] Synthesis of 2H-mintlactone 2H-mintlactone (4.62 g, 27.5 mmol, 95% yield) was obtained in the same manner as in Example 56 except that paramenthane-3,9-diol (5.00 g, 29.0 mmol) obtained in Example 55 was used instead of 1-butyl paramenthane 3,9-diol.

Examples 83 and 84: 2H-Mintlactone (Double Bond)

[Example 83] Synthesis of methyl-2-(4-methyl-2-oxocyclohex-3-en-1-yl)propanate

To a 500 ml four-neck flask equipped with a condenser, 32 mL of methanol was added under a nitrogen atmosphere, and sodium methoxide (16.3 g, 1.0 eq.) was gradually added thereto while lowering the temperature in the flask to 0° C. to 10° C. Further, methyl acetoacetate (32.3 mL, 300 mmol) was added dropwise, stirring was performed for 1 hour, and then, methyl 2-bromopropionate (50.0 g, 1.0 eq.) was added. After the completion of the addition, stirring was performed at 70° C. for 3 hours, and after the completion of the reaction, 35 mL of 0.5 N hydrochloric acid was added dropwise while maintaining the temperature. After recovering methanol, the aqueous layer was extracted with toluene, and drying was performed with anhydrous magnesium sulfate. Then, filtration and concentration were performed, thereby obtaining 58.14 g of crude ester intermediate (96% yield, 90.5% GCP.).

Subsequently, in a 500 mL reactor equipped with a dropping funnel and a condenser, 40.0 g of crude ester (as 90.5% p., 179 mmol) was dissolved in DMSO (80 mL), and potassium hydroxide (166 mg, 0.015 eq.) was gradually added to the reactor. The inside of the system was set to be weakly basic, and stirring was performed at 35° C. for 30 minutes. At the same temperature, methyl vinyl ketone (17.3 mL, 1.05 eq.) was added dropwise, and stirring was performed at 40° C. for 3 hours. The reaction liquid was cooled under ice-cooling, methanol (80 mL) was added, and sodium methoxide (3.20 g, 0.3 eq.) was slowly added at the same temperature. After performing stirring for 30 minutes, the completion of the reaction was confirmed by GC, and the solution in the system was neutralized with dilute hydrochloric acid until pH reached 6 to 7. After the methanol/water was recovered, the residue was added to a 200 mL reactor equipped with a condenser, and anhydrous magnesium chloride (14.1 g, 0.75 eq.) was added. After heating and stirring was performed at 130° C. for three and a half hours, the temperature of the reaction liquid was lowered to room temperature, and extraction was performed with ethyl acetate/water. An organic layer was concentrated, thereby obtaining 34.5 g of crude methyl ester. Vigreux distillation (bath temperature: 152° C. to 175° C., tower top temperature: 80° C. to 95° C., decompression degree: 44 Pa to 47 Pa) was performed, thereby obtaining 12.7 g of methyl ester intermediate (64.5 mmol, 36% yield in 2 steps).

Methyl Ester Intermediate (methyl 2-(4-methyl-2-oxocyclohex-3-en-1-yl)propanate)

$^1$H-NMR (500 MHz, CDCl$_3$): δ 1.10 (3H, d, J=7.1 Hz), 1.72-1.82 (1H, m), 1.94 (3H, s), 1.95-2.06 (1H, m), 2.27-2.49 (2H, m), 2.74 (1H, dt, J=13.8, 5.1 Hz), 3.04-3.11 (1H, m), 3.70 (3H, s), 5.87 (1H, s) (major)

$^1$H-NMR (500 MHz, CDCl$_3$): 1.20 (3H, dd, J=7.2, 0.8 Hz), 1.72-1.82 (1H, m), 1.94 (3H, s), 1.95-2.06 (1H, m), 2.27-2.49 (2H, m), 2.57 (1H, dt, J=12.0, 4.9 Hz), 2.94-3.03 (1H, m), 3.67 (3H, s), 5.87 (1H, s) (minor)

$^{13}$C-NMR (125 MHz, CDCl$_3$): 13.0 (CH3), 24.1 (CH3), 24.5 (CH2), 30.8 (CH2), 38.1 (CH), 48.0 (CH), 51.7 (CH3), 126.5 (CH), 161.9 (C), 176.7 (C), 198.9 (C) (major)

$^{13}$C-NMR (125 MHz, CDCl$_3$): 13.7 (CH3), 24.2 (CH3), 25.2 (CH2), 31.2 (CH2), 38.5 (CH), 48.5 (CH), 51.8 (CH3), 126.5 (CH), 161.5 (C), 175.3 (C), 198.8 (C) (minor)

[Example 84] Synthesis of 6-isopropyl-3,6-dimethyl-3a,4,5,6-tetrahydrobenzofuran-2 (3H)-one (Exemplary Compound iPr-3)

The reaction was performed under a nitrogen atmosphere. To a 200 mL four-neck flask equipped with a dropping funnel, a copper bromide/dimethyl sulfide complex (78.6 mg, 5 mol %), DMI (1.7 mL, 2 eq.), and THF (20 mL) were added, and the temperature of the inside of the system was lowered to about −10° C. while stirring the mixture. Further, an isopropyl magnesium chloride/THF solution (1.0 mol/L, 11 mL, 1.4 eq.) was added to the inside of the system, and a THF solution (30 mL) of the methyl ester intermediate (1.50 g, 7.64 mmol) obtained in Example 83 was added dropwise through the dropping funnel. After the completion of the addition, stirring was performed for 1 hour at a temperature of the inside of the system being 0° C. to 5° C. After the completion of the reaction was confirmed, the post-treatment was performed. The temperature of the inside of the system was lowered, quenching was performed with 1N hydrochloric acid, and extraction was performed with toluene. The oil layer was washed with an aqueous ammonia solution and a saturated saline solution. The oil layer was dried with anhydrous magnesium sulfate, and filtration and concentration were performed, thereby obtaining a crude product. Isolation and purification were performed with column chromatography, thereby obtaining the desired Exemplary Compound iPr-3 (1.07 g, 5.12 mmol, 67% yield).

Exemplary Compound iPr-3

6-isopropyl-3,6-dimethyl-3a,4,5,6-tetrahydrobenzofuran-2(3H)-one $^1$H-NMR (500 MHz, CDCl$_3$): 0.79-0.93 (6H, m), 0.95 (3H, s), 1.10-1.28 (1H, m), 1.29 (1H, d, J=7.0 Hz), 1.40-1.65 (2H, m), 1.91-2.00 (2H, m), 2.27-2.34 (1H, m), 2.38-2.47 (1H, m), 5.18 (1H, d, J=1.1 Hz) (major)

$^1$H-NMR (500 MHz, CDCl$_3$): δ 0.79-0.93 (6H, m), 0.95 (3H, s), 1.07-1.27 (4H, m), 1.40-1.65 (2H, m), 2.38-2.47 (1H, m), 2.48-2.58 (1H, m), 2.72-2.77 (1H, m), 2.81 (1H, qui, J=7.1 Hz), 5.18 (1H, d, J=1.1 Hz) (minor)

$^{13}$C-NMR (125 MHz, CDCl$_3$): 13.4 (CH3), 17.7 (CH3), 18.5 (CH3), 25.2 (CH3), 25.6 (CH2), 32.7 (CH2), 36.6 (CH), 37.1 (C), 41.7 (CH), 43.5 (CH), 109.7 (CH), 149.8 (C), 177.3 (C) (major)

$^{13}$C-NMR (125 MHz, CDCl$_3$): 14.9 (CH3), 16.7 (CH3), 18.5 (CH3), 21.4 (CH3), 25.4 (CH2), 31.0 (CH), 34.6 (C), 38.9 (CH), 52.0 (CH2), 52.4 (CH), 110.7 (CH), 149.9 (C), 176.3 (C) (minor)

Fragrance note: Fruity, Floral

Examples 85 to 88: Bromination/Mint Lactonization

[Example 85] Synthesis of 8-bromo-1-methyl-2H-mintlactone

The reaction was performed in accordance with a method of Tetrahedron 1993, 49, 29, P. 6429-6436. The reaction was performed under a nitrogen atmosphere. Exemplary Compound Me-1a (0.14 g, 5.10 mmol) obtained in Example 67 and THF (15 mL) were added to a 100 mL flask, and the temperature was lowered to −70° C. or lower while stirring the mixture. A THF solution of lithium diisopropylamide (1.04 mol/L, 5.9 mL, 6.12 mmol, 1.2 eq.) was added dropwise through a dropping funnel over 30 minutes, and after the completion of the addition, stirring was performed for 30 minutes while maintaining the temperature. Subsequently, a THF solution (5 mL) of trimethylsilyl chloride (0.84 mL, 6.63 mmol, 1.3 eq.) was added dropwise through the dropping funnel over 10 minutes, and stirring was performed for 15 minutes. N-bromosuccinimide (1.18 g, 6.63 mmol, 1.3 eq.) was added to the flask, and stirring was performed for 1 hour while maintaining the temperature. Stirring was performed for 3 hours while the temperature returned to room temperature gradually. The obtained solution was washed and extracted with toluene and tap water, and the residue obtained by drying and concentration was purified with column chromatography, thereby obtaining desired 8-bromo-1-methyl-2H-mintlactone (820 mg, 2.704 mmol, 53% yield). The compound was used for the next reaction as it is without subjecting to purification.

[Example 86] Synthesis of 8-bromo-1-butyl-2H-mintlactone 8-bromo-1-butyl-2H-mintlactone (820 mg, 53% yield) was obtained as a crude product in the same manner as in Example 85 except that Exemplary Compound Bu-1aa (1.14 g, 5.10 mmol) obtained in Example 56 was used instead of Exemplary Compound Me-1a. The compound was used for the next reaction as it is without subjecting to purification.

[Example 87] Synthesis of 1-methyl mintlactone (Exemplary Compound Me-2)

The reaction was performed in accordance with a method of Tetrahedron 1993, 49, 29, P. 6429-6436. To a 100 mL flask, 8-bromo-1-methyl-2H-mintlactone (820 mg, 2.704 mmol) obtained in Example 85, 1,8-diazabicyclo[5.4.0]-7-undecene (0.40 mL, 2.704 mmol, 1.0 eq.), and toluene (10 mL) were added, and the mixture was stirred under reflux for 3 hours. The reaction solution was cooled, followed by washing and extracting the obtained solution with toluene and tap water, and the residue obtained by drying and concentration was purified with column chromatography, thereby obtaining desired 1-methyl mintlactone (285 mg, 1.28 mmol, 47% yield) as Exemplary Compound Me-2.

Exemplary Compound Me-2: 1-methyl Mintlactone $^1$H-NMR (500 MHz, CDCl$_3$): δ 1.00 (3H, s), 1.08-1.12 (4H, m), 1.20-1.31 (1H, m), 1.64-1.70 (1H, m), 1.81 (1H, t, J=1.7 Hz), 2.19 (1H, ddd, J=12.2, 6.1, 2.4 Hz), 2.30-2.38 (1H, m), 2.70 (1H, ddd, J=14.5, 4.9, 2.0 Hz), 4.74-4.80 (1H, m)

$^{13}$C-NMR (125 MHz, CDCl$_3$): 8.2 (CH$_3$), 22.8 (CH$_2$), 24.1 (CH$_3$), 31.8 (CH$_3$), 31.9 (C), 39.0 (CH$_2$), 46.2 (CH$_2$), 78.4 (CH), 119.7 (C), 162.6 (C), 174.8 (C)

Fragrance note: Balsamic, Sweat, Coumarin, Fruity, Plum

[Example 88] Synthesis of 1-butyl Mintlactone (Exemplary Compound Bu-2)

1-butyl mintlactone (285 mg, 1.28 mmol, 47% yield) was obtained as Exemplary Compound Bu-2 in the same manner as in Example 87 except that 8-bromo-1-butyl-2H-mintlactone (820 mg, 2.70 mmol) obtained in Example 86 was used instead of 8-bromo-1-methyl-2H-mintlactone.

Exemplary Compound Bu-2: 1-butyl Mintlactone $^1$H-NMR (500 MHz, CDCl$_3$): δ 0.92-0.96 (3H, m), 0.97-1.19 (4H, m), 1.16-1.38 (7H, m), 1.63-1.68 (1H, m), 1.81 (3H, s), 2.22 (1H, ddd, J=12.1, 6.1, 2.4 Hz), 2.31-2.40 (1H, m), 2.66-2.74 (1H, m), 4.71-4.82 (1H, m) (major)

$^1$H-NMR (500 MHz, CDCl$_3$): δ 0.87-0.92 (3H, m), 0.97-1.19 (4H, m), 1.16-1.38 (6H, m), 1.42-1.48 (1H, m), 1.74-1.82 (4H, m), 2.27-2.40 (2H, m), 2.63-2.70 (1H, m), 4.71-4.82 (1H, m) (minor)

$^{13}$C-NMR (125 MHz, CDCl$_3$): 14.0 (CH$_3$), 21.8 (CH$_3$), 22.6 (CH$_2$), 23.4 (CH$_2$), 25.5 (CH$_2$), 28.1 (CH$_3$), 34.4 (C), 37.3 (CH$_2$), 44.4 (CH$_2$), 44.5 (CH$_2$), 78.5 (CH), 119.5 (C), 162.9 (C), 174.8 (C) (major)

$^{13}$C-NMR (125 MHz, CDCl$_3$): 14.1 (CH$_3$), 21.8 (CH$_3$), 22.5 (CH$_2$), 23.5 (CH$_2$), 25.9 (CH$_2$), 28.1 (CH$_3$), 34.4 (C), 35.5 (CH$_2$), 37.6 (CH$_2$), 44.2 (CH$_2$), 78.1 (CH), 119.6 (C), 162.9 (C), 174.8 (C) (minor)

Fragrance note: Fruity, woody, Lactone, Peach, Coconuts

Examples 89 and 90: α-alkylation

[Example 89] Synthesis of 8-allyl-2H-mintlactone (Exemplary Compound N-1-Ay)

The reaction was performed under a nitrogen atmosphere. To a 100 mL reactor equipped with a dropping funnel, 2H-mintlactone (1.26 g, 7.488 mmol) obtained in Example 82 and THF (10 mL) were added, and the mixture was stirred while lowering the temperature to −50° C. or lower. A lithium/diisopropylamide/THF solution (1.04 mol/L, 2.5 eq., 18 mL) was added dropwise through the dropping funnel over 30 minutes, and further, a THF solution (10 mL) of allyl bromide (1.62 mL, 2.5 eq.) was added dropwise over 30 minutes. After the completion of the dropwise addition, the temperature of the inside of the system was raised to room temperature, and the mixture was stirred for 2 hours. The completion of the reaction was confirmed by GC, and the post-treatment was performed. Toluene and a saturated saline solution were added to the solution, and the oil layer was washed twice with 1N hydrochloric acid and washed once with 5% aqueous sodium bicarbonate solution, followed by drying with anhydrous magnesium sulfate, and then, filtration and concentration were performed. The obtained residue was isolated and purified with column chromatography, thereby obtaining 8-ally-2H-mintlactone (1.09 g, 70% yield) as Exemplary Compound N-1-Ay.

Exemplary Compound N-1-Ay:
8-allyl-2H-mintlactone $^1$H-NMR (500 MHz, CDCl$_3$): δ 0.96-1.08 (4H, m), 1.12-1.21 (4H, m), 1.36 (1H, qd, J=12.5, 3.8 Hz), 1.54-1.69 (2H, m), 1.74 (1H, dq, J=12.6, 3.1 Hz), 1.80-1.86 (1H, m), 2.12 (1H, dd, J=14.2, 7.7 Hz), 2.22-2.28 (1H, m), 2.32 (1H, dd, J=14.1, 7.8 Hz), 4.02 (1H, td, J=11.1, 3.8 Hz), 5.06-5.14 (2H, m), 5.74-5.86 (1H, m)
$^{13}$C-NMR (125 MHz, CDCl$_3$): 21.5 (CH$_3$), 22.0 (CH$_3$), 23.1 (CH$_2$), 31.3 (CH), 34.4 (CH$_2$), 35.8 (CH$_2$), 39.0 (CH$_2$), 45.4 (C), 54.8 (CH), 79.7 (CH), 118.6 (CH$_2$), 133.0 (CH), 180.8 (C)
Fragrance note: Fruity, Sweet, Cookie, Pineapple, Dry-fruit, Galbanum

[Example 90] Synthesis of 8-butyl-2H-mintlactone (Exemplary Compound N-1-Bu)

8-butyl-2H-mintlactone (650 mg, 2.90 mmol, 49% yield) was obtained as Exemplary Compound N-1-Bu from 1.00 g (5.942 mmol) of 2H-mintlactone in the same manner as in Example 89 except that butyl iodide was used instead of allyl bromide.

Exemplary Compound N-1-Bu:
8-butyl-2H-mintlactone $^1$H-NMR (500 MHz, CDCl$_3$): δ 0.89 (3H, t, J=7.1 Hz), 0.95-1.08 (4H, m), 1.12-1.23 (4H, m), 1.24-1.40 (6H, m), 1.49-1.65 (3H, m), 1.71 (1H, ddd, J=12.6, 6.7, 1.0 Hz), 1.79-1.85 (1H, m), 2.21-2.28 (1H, m), 3.99 (1H, td, J=11.9, 3.8 Hz)
$^{13}$C-NMR (125 MHz, CDCl$_3$): 13.9 (CH$_3$), 21.2 (CH$_3$), 22.0 (CH$_2$), 23.0 (CH$_2$), 23.3 (CH$_2$), 26.2 (CH$_2$), 30.7 (CH$_2$), 31.3 (CH), 34.4 (CH$_2$), 39.2 (CH$_2$), 45.3 (C), 55.3 (CH), 79.6 (CH), 181.3 (C)
Fragrance note: Fruity, Creamy, Spicy.

Examples 91 to 103: Etherification

[Example 91] Synthesis of 1-isopropyltetrahydromenthofuran (Exemplary Compound iPr-4)

The reaction was performed in accordance with a method of Chem Sus Chem, 2012, 5, P. 1578-1586. To a 100 mL reactor equipped with a condenser, 1-isopropyl paramenthane-3,9-diol (500 mg, 2.333 mmol) obtained in Example 41, potassium t-butoxide (393 mg, 1.5 eq., 3.50 mmol), and dimethyl carbonate (7.8 mL) were added, and the mixture was stirred under reflux for 2 hours. The completion of the reaction was confirmed by GC and TLC, and the post-treatment was performed. The temperature of the solution was lowered to room temperature, and toluene and tap water were added to perform washing. The oil layer was washed once with 1N hydrochloric acid and washed once with 5% aqueous sodium bicarbonate solution, followed by drying with anhydrous magnesium sulfate, and filtration and concentration were performed. The obtained residue was isolated and purified with column chromatography, thereby obtaining desired 1-isopropyltetrahydromenthofuran (403 mg, 2.14 mmol, 92% yield) as Exemplary Compound iPr-4.

Exemplary Compound iPr-4:
1-isopropyltetrahydromenthofuran $^1$H-NMR (500 MHz, CDCl$_3$): δ 0.82 (3H, s), 0.86 (6H, dd, J=6.5, 1.0 Hz), 0.93 (3H, d, J=7.5 Hz), 1.01-1.45 (4H, m), 1.47-1.53 (1H, m), 1.60-1.67 (1H, m), 1.77-1.90 (1H, m), 1.95 (1H, ddd, J=11.5, 4.5, 2.0 Hz), 2.24-2.37 (1H, m), 3.36-3.46 (2H, m), 4.12-4.17 (1H, m) (major)
$^1$H-NMR (500 MHz, CDCl$_3$): δ 0.78 (3H, s), 0.86 (6H, dd, J=6.5, 1.0 Hz), 0.92 (3H, d, J=7.01 Hz), 1.01-1.45 (4H, m), 1.54-1.57 (1H, m), 1.60-1.67 (1H, m), 1.77-1.90 (1H, m), 2.21-2.24 (1H, m), 2.24-2.37 (1H, m), 3.36-3.46 (2H, m), 4.12-4.17 (1H, m) (minor)
$^{13}$C-NMR (125 MHz, CDCl$_3$): 15.5 (CH3), 17.0 (CH3), 17.2 (CH3), 19.3 (CH3), 21.1 (CH2), 34.0 (CH2), 35.7 (CH2), 37.6 (C), 39.7 (CH), 40.6 (CH), 49.1 (CH), 75.7 (CH2), 77.0 (CH) (major)
$^{13}$C-NMR (125 MHz, CDCl$_3$): 15.6 (CH3), 16.8 (CH3), 17.0 (CH3), 20.4 (CH2), 23.0 (CH3), 28.6 (CH), 33.9 (CH), 36.5 (CH2), 37.5 (C), 41.2 (CH2), 49.4 (CH), 75.5 (CH), 75.6 (CH2) (minor)
Fragrance note: Floral, Fruity

[Example 92] Synthesis of 1-methyltetrahydromenthofuran (Exemplary Compound Me-4)

1-methyltetrahydromenthofuran (320 mg, 1.90 mmol, 56% yield) was obtained as Exemplary Compound Me-4 in the same manner as in Example 91 except that 1-methyl paramenthane-3,9-diol (631 mg, 3.39 mmol) obtained in Example 37 was used instead of 1-isopropyl paramenthane-3,9-diol.

Exemplary Compound Me-4:
5-methyltetrahydromenthofuran $^1$H-NMR (500 MHz, CDCl$_3$): δ 0.91-0.94 (6H, m), 0.99 (3H, s), 1.14-1.24 (2H, m), 1.28-1.35 (2H, m), 1.43-1.48 (1H, m), 1.58-1.63 (1H, m), 1.86 (1H, ddd, J=11.7, 4.0, 1.9 Hz), 2.31 (1H, ddd, J=13.4, 7.1, 3.0 Hz), 3.37-3.44 (2H, m), 4.16 (1H, dd, J=8.7, 7.2 Hz)
$^{13}$C-NMR (125 MHz, CDCl$_3$): 15.5 (CH$_3$), 21.3 (CH$_2$), 26.0 (CH$_3$), 32.5 (C), 33.2 (CH$_3$), 33.9 (CH), 39.3 (CH$_2$), 44.4 (CH$_2$), 49.2 (CH), 74.7 (CH$_2$), 77.0 (CH)
Fragrance note: Coumarine, Minty, Herbal

[Example 93] Synthesis of 1-ethyltetrahydromenthofuran (Exemplary Compound Et-4)

1-ethyltetrahydromenthofuran (398 mg, 2.18 mmol, 88% yield) was obtained as Exemplary Compound Et-4 in the same manner as in Example 91 except that 1-ethylparamenthane-3,9-diol (500 mg, 2.50 mmol) obtained in Example 40 was used instead of 1-isopropyl paramenthane-3,9-diol.

Exemplary Compound Et-4:
1-ethyltetrahydromenthofuran $^1$H-NMR (500 MHz, CDCl$_3$): δ 0.80-0.95 (9H, m), 1.01-1.45 (7H, m), 1.53-1.65 (1H, m), 1.87 (1H, ddd, J=11.5, 4.0, 1.5 Hz), 2.24-2.37 (1H, m), 3.36-3.47 (2H, m), 4.16 (1H, dd, J=8.5, 7.5 Hz) (major)
$^1$H-NMR (500 MHz, CDCl$_3$): δ 0.80-0.95 (9H, m), 1.01-1.45 (7H, m), 1.53-1.65 (1H, m), 2.00 (1H, ddd, J=12.0, 4.0, 1.5 Hz), 2.24-2.37 (1H, m), 3.36-3.47 (2H, m), 4.16 (1H, dd, J=8.5, 7.5 Hz) (minor)
$^{13}$C-NMR (125 MHz, CDCl$_3$): 7.8 (C3), 15.6 (CH3), 21.2 (CH2), 23.1 (CH3), 34.0 (CH), 35.2 (C), 37.4 (CH2), 38.3 (CH2), 42.0 (CH2), 49.4 (CH), 75.8 (CH2), 76.7 (CH) (major)
$^{13}$C-NMR (125 MHz, CDCl$_3$): 7.9 (CH3), 15.6 (CH3), 20.9 (CH2), 28.9 (CH3), 29.4 (CH2), 34.0 (CH), 35.0 (C), 38.0 (CH2), 41.4 (CH2), 49.2 (CH), 75.7 (CH2), 76.2 (CH) (minor)
Fragrance note: Floral, Fruity, Green, Woody

[Example 94] Synthesis of
1-propyltetrahydromenthofuran (Exemplary Compound Pr-4)

Desired 1-propyltetrahydromenthofuran (868 mg, 50% yield) was obtained as Exemplary Compound Pr-4 in the same manner as in Example 91 except that 1-propyl paramenthane-3,9-diol (1.90 g, 8.86 mmol) obtained in Example 42 was used instead of 1-isopropyl paramenthane-3,9-diol.

Exemplary Compound Pr-4:
1-propyltetrahydromenthofuran $^1$H-NMR (500 MHz, CDCl$_3$): δ 0.85-0.95 (9H, m), 1.01-1.45 (9H, m), 1.53-1.65 (1H, m), 1.87 (1H, ddd, J=11.7, 3.8, 1.5 Hz), 2.24-2.37 (1H, m), 3.36-3.47 (2H, m), 4.15 (1H, dd, J=8.3, 7.6 Hz) (major)
$^1$H-NMR (500 MHz, CDCl$_3$): δ 0.80-0.95 (9H, m), 1.01-1.35 (8H, m), 1.53-1.65 (2H, m), 2.00 (1H, ddd, J=12.0, 3.6, 1.6 Hz), 2.24-2.37 (1H, m), 3.36-3.47 (2H, m), 4.16 (1H dd, J=8.5, 7.5 Hz) (minor)
$^{13}$C-NMR (125 MHz, CDCl$_3$): 15.0 (CH3), 15.5 (CH3), 16.6 (CH2), 21.1 (CH2), 23.6 (CH3), 33.9 (CH), 35.2 (C), 37.8 (CH2), 42.5 (CH2), 48.8 (CH2), 49.4 (CH), 75.6 (CH2), 76.2 (CH) (major)
$^{13}$C-NMR (125 MHz, CDCl$_3$): 15.0 (CH3), 15.6 (CH3), 16.7 (CH2), 20.9 (CH2), 29.6 (CH3), 33.9 (CH), 35.0 (C), 38.5 (CH2), 39.9 (CH2), 41.9 (CH2), 49.2 (CH), 76.7 (CH2), 77.0 (CH) (minor)
Fragrance note: Floral, Fruity, Apricot, Jasmin, metallic

[Example 95] Synthesis of
1-butyltetrahydromenthofuran (Exemplary Compound Bu-4a)

Desired 1-butyltetrahydromenthofuran (0.512 g, 52% yield) was obtained as Exemplary Compound Bu-4a in the same manner as in Example 91 except that 1-butyl paramenthane-3,9-diol (1.08 g, 4.73 mmol) obtained in Example 36 was used instead of 1-isopropyl paramenthane-3,9-diol.

Exemplary Compound Bu-4a:
1-butyltetrahydromenthofuran $^1$H-NMR (500 MHz, CDCl$_3$): δ 0.88-0.94 (9H, m), 1.00-1.67 (12H, m), 1.88 (1H, ddd, J=11.6, 3.9, 1.3 Hz), 2.24-2.35 (1H, m), 3.35-3.46 (2H, m), 4.16 (1H, t, J=8.5 Hz) (major)
$^1$H-NMR (500 MHz, CDCl$_3$): δ 0.88-0.94 (9H, m), 1.00-1.6.7 (12H, m), 2.00 (1H, ddd, J=12.0, 3.6, 1.5 Hz), 2.24-2.35 (1H, m), 3.35-3.46 (2H, m), 4.16 (1H, t, J=8.5 Hz) (minor)
$^{13}$C-NMR (125 MHz, CDCl$_3$): 14.2 (CH3), 15.5 (CH3), 21.1 (CH2), 23.5 (CH2), 23.6 (CH3), 25.6 (CH2), 34.0 (CH), 35.1 (C), 37.8 (CH2), 42.5 (CH2), 46.0 (CH2), 49.4 (CH2), 75.7 (CH2), 77.0 (CH) (major)
$^{13}$C-NMR (125 MHz, CDCl$_3$): 14.2 (CH3), 15.6 (CH3), 20.9 (CH2), 23.6 (CH2), 25.8 (CH2), 29.6 (CH3), 33.9 (CH), 34.9 (C), 37.1 (CH2), 38.5 (CH2), 41.8 (CH2), 49.2 (CH2), 75.7 (CH2), 76.2 (CH) (minor)
Fragrance note: Tuberose, Lactone, Aquatic, Fruity, white, Creamy

[Example 96] Synthesis of
1-butyltetrahydromenthofuran Isomer (Exemplary Compound Bu-4c)

1-butyltetrahydromenthofuran isomer (0.221 g, 8% yield) was obtained as Exemplary Compound Bu-4c by isolation and purification, and performing the reaction in the same manner as in Example 91 except that 1-butyl paramenthane-3,9-diol (3.00 g, 13.1 mmol), which was obtained by adding a borane solution dropwise at 25° C. and allowing it to react in Example 36, was used instead of 1-isopropyl paramenthane-3,9-diol.

Exemplary Compound Bu-4c:
1-butyltetrahydromenthofuran $^1$H-NMR (500 MHz, CDCl$_3$): δ 0.88-0.94 (9H, m), 1.00-1.67 (12H, m), 1.78-1.84 (1H, m), 2.24-2.35 (1H, m), 3.33-3.39 (2H, m), 4.05 (1H, td, J=7.5, 3.1 Hz) (major)
$^1$H-NMR (500 MHz, CDCl$_3$): δ 0.88-0.94 (9H, m), 1.00-1.67 (12H, m), 1.91-1.97 (1H, m), 2.24-2.35 (1H, m), 3.28-3.35 (2H, m), 4.05 (1H, td, J=7.5, 3.1 Hz) (minor)
$^{13}$C-NMR (125 MHz, CDCl$_3$): 14.2 (CH3), 15.6 (CH3), 21.1 (CH2), 23.6 (CH2), 23.7 (CH3), 25.6 (CH2), 35.1 (C), 37.8 (CH2), 38.2 (CH), 42.3 (CH2), 46.0 (CH2), 53.6 (CH), 75.6 (CH2), 81.1 (CH) (major)
$^{13}$C-NMR (125 MHz, CDCl$_3$): 14.2 (CH3), 15.9 (CH3), 20.9 (CH2), 23.3 (CH2), 25.8 (CH2), 29.7 (CH3), 35.0 (C), 37.1 (CH2), 38.1 (CH), 41.6 (CH2), 46.0 (CH2), 53.3 (CH), 74.7 (CH2), 80.5 (CH) (minor)
Fragrance note: Tuberose, Lactone, Fruity, Aquatic, white, Creamy Example 97

When Exemplary Compound Bu-4a and Exemplary Compound Bu-4c, which were isomers, were mixed and the fragrance note of the mixture was confirmed, the same fragrance note as that of Exemplary Compound Bu-4a was obtained from the mixture.

[Example 98] Synthesis of
1-iso-butyltetrahydromenthofuran (Exemplary Compound iBu-4a)

1-iso-butyltetrahydromenthofuran (596 mg, 2.83 mmol, 51% yield) was obtained as Exemplary Compound iBu-4a in the same manner as in Example 91 except that 1-iso-butyl paramenthane-3,9-diol (1.26 g, 5.517 mmol) obtained in Example 43 was used instead of 1-isopropyl paramenthane-3,9-diol.

Exemplary Compound iBu-4a:
1-iso-butyltetrahydromenthofuran $^1$H-NMR (500 MHz, CDCl$_3$): δ 0.86-0.96 (12H, m), 1.03-1.80 (9H, m), 1.91 (1H, ddd, J=11.7, 4.1, 1.8 Hz), 2.24-2.35 (1H, m), 3.33-3.45 (2H, m), 4.11-4.18 (1H, m) (major)
$^1$H-NMR (500 MHz, CDCl$_3$): δ 0.86-0.96 (12H, m), 1.03-1.80 (9H, m), 2.03 (1H, ddd, J=11.8, 4.1, 1.9 Hz), 2.24-2.35 (1H, m), 3.33-3.45 (2H, m), 4.11-4.18 (1H, m) (minor)
$^{13}$C-NMR (125 MHz, CDCl$_3$): 15.5 (CH3), 21.0 (CH2), 23.6 (CH), 24.1 (CH3), 25.7 (CH3), 25.7 (CH3), 33.9 (CH), 36.0 (C), 38.2 (CH2), 42.7 (CH2), 49.3 (CH), 55.3 (CH), 75.6 (CH2), 76.8 (CH) (major)
$^{13}$C-NMR (125 MHz, CDCl$_3$): 15.6 (CH3), 22.7 (CH2), 24.6 (CH), 25.5 (CH3), 25.7 (CH3), 30.3 (CH3), 33.9 (CH), 35.8 (C), 39.1 (CH2), 42.6 (CH2), 46.3 (CH2), 49.2 (CH), 75.6 (CH2), 77.0 (CH) (minor)
Fragrance note: Fruity, Floral, Plum, Peach

[Example 99] Synthesis of 1-n-pentyltetrahydromenthofuran (Exemplary Compound Pe-4a)

Desired 5-pentyltetrahydromenthofuran (367 mg, 30% yield) was obtained as Exemplary Compound Pe-4a in the same manner as in Example 91 except that 1-n-pentyl paramenthane-3,9-diol (0.23 g, 5.07 mmol) obtained in Example 48 was used instead of 1-isopropyl paramenthane-3,9-diol.

Exemplary Compound Pe-4a:
5-pentyltetrahydromenthofuran $^1$H-NMR (500 MHz, CDCl$_3$): δ 0.85-0.95 (9H, m), 1.00-1.37 (12H, m), 1.40-1.46 (1H, m), 1.55-1.64 (1H, m), 1.87 (1H, ddd, J=12.0, 4.0, 1.9 Hz), 2.24-2.38 (1H, m), 3.36-3.47 (2H, m), 4.16 (1H, dd, J=8.5, 7.5 Hz) (major)
$^1$H-NMR (500 MHz, CDCl$_3$): δ 0.85-0.95 (9H, m), 1.00-1.37 (12H, m), 1.51-1.55 (1H, m), 1.55-1.64 (1H, m), 2.00 (1H, ddd, J=12.0, 3.5, 1.5 Hz), 2.24-2.38 (1H, m), 3.36-3.47 (2H, m), 4.16 (1H, dd, J=8.5, 7.5 Hz) (minor)
$^{13}$C-NMR (125 MHz, CDCl$_3$): 14.1 (CH3), 15.6 (CH3), 21.1 (CH2), 22.7 (CH2), 23.0 (CH2), 23.6 (CH3), 32.8 (CH2), 34.0 (CH), 35.0 (C), 37.8 (CH2), 42.5 (CH2), 46.3 (CH2), 49.4 (CH), 74.7 (CH2), 76.3 (CH) (major)
$^{13}$C-NMR (125 MHz, CDCl$_3$): 14.1 (CH3), 15.5 (CH3), 20.9 (CH2), 22.8 (CH2), 23.2 (CH2), 29.6 (CH3), 32.8 (CH2), 33.9 (CH), 35.1 (C), 37.4 (CH2), 38.5 (CH2), 41.8 (CH2), 49.2 (CH), 76.8 (CH2), 77.0 (CH) (minor)
Fragrance note: Floral, Fruity, coumarin

[Example 100] Synthesis of 1-n-hexyl Tetrahydromenthofuran (Exemplary Compound Hx-4a)

Desired 1-n-hexyl tetrahydromenthofuran (94.1 mg, 41% yield) was obtained as Exemplary Compound Hx-4a in the same manner as in Example 91 except that 1-n-hexyl paramenthane-3,9-diol (246 mg, 0.9601 mmol) obtained in Example 50 was used instead of 1-isopropyl paramenthane-3,9-diol.

Exemplary Compound Hx-4a: 1-n-hexyl Tetrahydromenthofuran $^1$H-NMR (500 MHz, CDCl$_3$): δ 0.85-0.95 (9H, m), 1.00-1.45 (15H, m), 1.50-1.65 (1H, m), 1.87 (1H, ddd, J=11.5, 4.0, 1.5 Hz), 2.24-2.38 (1H, m), 3.36-3.47 (2H, m), 4.15 (1H, dd, J=8.5, 7.5 Hz) (major)
$^1$H-NMR (500 MHz, CDCl$_3$): δ 0.85-0.95 (9H, m), 1.00-1.37 (15H, m), 1.50-1.65 (1H, m), 2.00 (1H, ddd, J=12.0, 3.5, 1.5 Hz), 2.24-2.38 (1H, m), 3.36-3.47 (2H, m), 4.15 (1H, dd, J=8.5, 7.5 Hz) (minor)
$^{13}$C-NMR (125 MHz, CDCl$_3$): 14.1 (CH3), 15.5 (CH3), 21.1 (CH2), 22.7 (CH2), 23.3 (CH2), 23.7 (CH3), 30.2 (CH2), 31.9 (CH2), 34.0 (CH), 35.1 (C), 37.8 (CH2), 42.5 (CH2), 46.3 (CH2), 49.4 (CH), 75.7 (CH2), 76.2 (CH) (major)
$^{13}$C-NMR (125 MHz, CDCl$_3$): 14.1 (CH3), 15.6 (CH3), 20.9 (CH2), 22.7 (CH2), 23.5 (CH2), 29.6 (CH3), 30.3 (CH2), 32.0 (CH2), 33.9 (CH), 35.0 (C), 37.4 (CH2), 38.5 (CH2), 41.8 (CH2), 49.2 (CH), 76.8 (CH2), 77.0 (CH) (minor)
Fragrance note: Fruity, Coconuts

[Example 101] Synthesis of 1-n-heptyltetrahydromenthofuran (Exemplary Compound Hp-4a)

Desired 1-heptyltetrahydromenthofuran (367 mg, 30% yield) was obtained as Exemplary Compound Hp-4a in the same manner as in Example 91 except that 1-n-heptyl paramenthane-3,9-diol (2.00 g, 7.94 mmol) obtained in Example 52 was used instead of 1-isopropyl paramenthane-3,9-diol.

Exemplary Compound Hp-4a:
1-n-heptyltetrahydromenthofuran $^1$H-NMR (500 MHz, CDCl$_3$): δ 0.85-0.95 (9H, m), 1.00-1.45 (15H, m), 1.50-1.63 (1H, m), 2.00 (1H, dd, J=11.9, 2.1 Hz), 2.24-2.36 (1H, m), 3.36-3.47 (2H, m), 4.15 (1H, t, J=7.1, Hz) (major)
$^1$H-NMR (500 MHz, CDCl$_3$): δ 0.85-0.95 (9H, m), 1.00-1.45 (15H, m), 1.50-1.63 (1H, m), 1.87 (1H, dd, J=11.7, 2.7 Hz), 2.24-2.36 (1H, m), 3.36-3.47 (2H, m), 4.15 (1H, t, J=7.1, Hz) (minor)
$^{13}$C-NMR (125 MHz, CDCl$_3$): 14.1 (CH3), 15.6 (CH3), 20.9 (CH2), 22.7 (CH2), 23.5 (CH2), 23.7 (CH3), 29.4 (CH2), 30.6 (CH2), 31.9 (CH2), 33.9 (CH), 35.0 (C), 37.4 (CH2), 38.5 (CH2), 41.8 (CH2), 49.2 (CH), 75.6 (CH2), 76.2 (CH) (major)
$^{13}$C-NMR (125 MHz, CDCl$_3$): 14.1 (CH3), 15.5 (CH3), 21.1 (CH2), 22.7 (CH2), 23.3 (CH2), 29.3 (CH2), 29.6 (CH3), 30.5 (CH2), 31.9 (CH2), 33.9 (CH), 35.1 (C), 37.8 (CH2), 42.5 (CH2), 46.3 (CH2), 49.4 (CH), 76.7 (CH2), 77.0 (CH) (minor)
Fragrance note: Fruity, gluten

[Example 102] Synthesis of 1-n-octyltetrahydromenthofuran (Exemplary Compound Oc-4a)

Desired 1-n-octyltetrahydromenthofuran (724 mg, 55% yield) was obtained as Exemplary Compound Oc-4a in the same manner as in Example 91 except that 1-n-octyl paramenthane-3,9-diol (1.40 g, 4.92 mmol) obtained in Example 53 was used instead of 1-isopropyl paramenthane-3,9-diol.

Exemplary Compound Oc-4a:
1-n-octyltetrahydromenthofuran $^1$H-NMR (500 MHz, CDCl$_3$): δ 0.85-0.93 (9H, m), 1.00-1.45 (18H, m), 1.51-1.62 (2H, m), 2.00 (1H, ddd, J=12.0, 3.5, 1.5 Hz), 2.23-2.35 (1H, m), 3.38-3.45 (2H, m), 4.15 (1H, dd, J=9.5, 7.5 Hz) (major)
$^1$H-NMR (500 MHz, CDCl$_3$): 0.85-0.93 (9H, m), 1.00-1.45 (18H, m), 1.51-1.62 (2H, m), 1.87 (1H, ddd, J=12.0, 4.0, 20 Hz), 2.23-2.35 (1H, m), 3.38-3.45 (2H, m), 4.15 (1H, dd, J=9.5, 7.5 Hz) (minor)
$^{13}$C-NMR (125 MHz, CDCl$_3$): 14.1 (CH3), 15.6 (CH3), 20.9 (CH2), 22.7 (CH2), 23.3 (CH2), 23.6 (CH3), 29.3 (CH2), 29.5 (CH2), 30.6 (CH2), 31.9 (CH), 33.9 (CH), 35.0 (C), 37.4 (CH2), 38.5 (CH2), 41.8 (CH2), 49.2 (CH), 75.6 (CH2), 76.2 (CH) (major)
$^{13}$C-NMR (125 MHz, CDCl$_3$): 14.1 (CH3), 15.6 (CH3), 21.1 (CH2), 22.7 (CH2), 23.3 (CH2), 29.3 (CH2), 29.4 (CH2), 29.6 (CH3), 30.5 (CH2), 31.9 (CH), 33.9 (CH), 35.1 (C), 37.8 (CH2), 42.5 (CH2), 46.3 (CH2), 49.4 (CH), 76.7 (CH2), 77.0 (CH) (minor)
Fragrance note: Fruity, Apple, cinnamon

[Example 103] Synthesis of 1-phenyltetrahydromenthofuran (Exemplary Compound Ph-4a)

1-phenyltetrahydromenthofuran (360 mg, 1.56 mmol, 97% yield) was obtained as Exemplary Compound Ph-4a in the same manner as in Example 91 except that 1-phenyl paramenthane-3,9-diol (400 mg, 1.61 mmol) obtained in Example 54 was used instead of 1-isopropyl paramenthane-3,9-diol.

Exemplary Compound Ph-4a:
1-phenyltetrahydromenthofuran $^1$H-NMR (500 MHz, CDCl$_3$): 0.72 (3H, d, J=7.2 Hz), 1.22 (3H, s), 1.25-1.30 (1H, m), 1.40-1.70 (5H, m), 2.24-2.33 (1H, m), 2.47 (1H, ddd, J=14.0, 5.3, 2.7 Hz), 3.12 (1H, td, J=11.2, 3.3 Hz), 3.31 (1H, dd, J=8.3, 3.1 Hz), 4.14 (1H, dd, J=8.5, 7.4 Hz), 7.12-7.43 (5H, m) (major)
$^1$H-NMR (500 MHz, CDCl$_3$): δ 0.97 (3H, d, J=7.2 Hz), 1.31 (3H, s), 1.40-1.70 (4H, m), 1.75-1.83 (1H, m), 1.92-1.97 (1H, m), 2.32-2.41 (2H, m), 3.48 (1H, dd, J=8.7, 3.1 Hz), 3.62 (1H, td, J=10.9, 3.9 Hz), 4.20 (1H, dd, J=8.5, 7.4 Hz), 7.12-7.43 (5H, m) (minor)
$^{13}$C-NMR (125 MHz, CDCl$_3$): 15.4 (CH3), 21.7 (CH2), 26.2 (CH3), 33.9 (CH), 37.5 (CH2), 40.2 (C), 43.0 (CH2), 49.3 (CH), 75.9 (CH2), 76.8 (CH), 125.9 (CH×2), 128.2 (CH), 128.5 (CH×2), 147.1 (C) (major)
$^{13}$C-NMR (125 MHz, CDCl$_3$): 15.6 (CH3), 21.4 (CH2), 33.9 (CH), 35.3 (CH3), 38.2 (CH2), 39.3 (C), 42.7 (CH2), 49.0 (CH), 75.7 (CH2), 76.5 (CH), 125.1 (CH×2), 125.5 (CH×2), 125.8 (CH), 151.5 (C) (minor)
Fragrance note: Floral, Fruity, Balsamic, Rosy, Plum, Whitefloral

[Example 104] Confirmation of Fragrance Note Persistence

Each of γ-nonalactone, γ-decalactone, δ-undecalactone, and nectaryl, which were comparative compounds for confirming fragrance note persistence, and Exemplary Compound Bu-1aa obtained in Example 56 was added to a blotter by 30 μL, and the persistence of the aroma was confirmed. As a result, aromas of all the comparative compounds were not felt within 3 weeks, but the aroma of Exemplary Compound Bu-1aa lasted for 4 months, and the fragrance note thereof was almost not changed compared with the fragrance note at the time of adding Exemplary Compound Bu-1aa to the blotter.

TABLE 1

|  | Persistence of fragrance |
| --- | --- |
| γ-nonalactone | 24 hours |
| γ-decalactone | 2 weeks |
| δ-undecalactone | 2.5 weeks |
| Nectaryl | 3 weeks |
| Exemplary Compound Bu-1aa | 4 months |

[Example 105] Synthesis of 1-(4-butyl-2-hydroxy-4-methylcyclohexyl)ethane-1-one

To a 100 mL reaction flask, 5-butylisopulegol (1.20 g, 5.70 mmol) obtained in Example 25 and 1-butanol (10 mL) were added, followed by stirring the mixture inside the system at 10° C. or lower, and ozone gas was blown from an ozone generation device to allow them to react. After 2 hours, the blowing of ozone gas was stopped, and a 5% aqueous sodium bicarbonate solution was added dropwise to terminate the reaction. Ethyl acetate was added to the inside of the system, followed by washing the solution once with an aqueous sodium bicarbonate solution and twice with a saturated saline solution, and the oil layer was dried with anhydrous magnesium sulfate, and filtration and concentration were performed, thereby obtaining desired 1-(4-butyl-2-hydroxy-4-methylcyclohexyl)ethane-1-one (0.99 g, 82% yield).

[Example 106] Synthesis of 1-(4-butyl-2-((t-butyldimethylsilyl)oxy)-4-methylcyclohexyl)ethan-1-one The reaction was performed under a nitrogen atmosphere. To a 50 mL flask, 1-(4-butyl-2-hydroxy-4-methylcyclohexyl)ethane-1-one (3.00 g, 14.1 mmol) obtained in Example 105, dimethyl t-butyl silyl chloride (3.19 g, 1.5 eq.), imidazole (1.92 g, 2.0 eq.), and DMF (9 mL) were added, and the mixture was stirred at a bath temperature of 30° C. for one and a half hours. The complete consumption of the substrate was confirmed by GC, and the post-treatment was performed. The temperature of the reaction solution was lowered to room temperature, followed by adding a saturated saline solution, and the extraction was performed twice with toluene. The obtained oil layer was dried with anhydrous magnesium sulfate, and filtration and concentration were performed, thereby obtaining a desired crude silyl ether. The crude silyl ether was isolated and purified with column chromatography, thereby obtaining desired 1-(4-butyl-2-((t-butyldimethylsilyl)oxy)-4-methylcyclohexyl)ethan-1-one (7.63 g, 29.2 mmol, 80% yield).

[Example 107] Synthesis of ethyl-3-(4-butyl-2-((t-butyldimethylsilyl)oxy)-4-methylcyclohexyl)-2-butenoate The reaction was performed under a nitrogen atmosphere. To a 100 mL reactor equipped with a dropping funnel and a condenser, sodium hydride (60% oil dispersion, 735 mg, 1.5 eq.) and DMF (20 mL) were added, and the temperature was lowered to 10° C. or lower while stirring the mixture. A DMF (5 mL) solution of triethyl phosphonoacetate (3.7 mL, 1.5 eq.) was added dropwise through the dropping funnel over 30 minutes, and stirring was performed for 30 minutes to allow the reaction solution to be aged. Further, a DMF (5 mL) solution of 1-(4-butyl-2-((t-butyldimethylsilyl)oxy)-4-methylcyclohexyl)ethan-1-one (4.00 g, 12.3 mmol) obtained in Example 106 was added dropwise through the dropping funnel over 20 minutes. After the completion of dropwise addition, the temperature of the inside of the system was raised to 120° C., and the mixture was stirred. After performing stirring for 5 hours, the generation of the target product was confirmed, and the post-treatment was performed. The temperature of the inside of the system was lowered to 10° C. or lower, followed by adding 1N hydrochloric acid to perform quenching, and the solution was extracted twice with toluene. The oil layer was dried with anhydrous magnesium sulfate, and the concentration under reduced pressure was performed, thereby obtaining a crude product. The crude product was isolated and purified with column chromatography, thereby obtaining 1.64 g of desired ethyl-3-(4-butyl-2-((t-butyldimethylsilyl)oxy)-4-methylcyclohexyl)-2-butenoate (4.13 mmol, 37% yield).

[Example 108] Synthesis of ethyl-3-(4-butyl-2-((t-butyldimethylsilyl)oxy)-4-methylcyclohexyl)butanoate To a 100 mL autoclave, ethyl-3-(4-butyl-2-((t-butyldimethylsilyl)oxy)-4-methylcyclohexyl)-2-butenoate (1.64 g, 4.13 mmol) obtained in Example 107, supported palladium carbon (5% Pd wet, 10 mg), and ethanol (5 mL) were added, and the mixture was heated and stirred at 80° C. under a hydrogen pressure of 1 MPa. After 2 hours, as the post-treatment, cooling was performed, and the obtained solution was filtered and concentrated after hydrogen purge, thereby obtaining desired ethyl-3-(4-butyl-2-((t-butyldimethylsilyl)oxy)-4-methylcyclohexyl)butanoate (1.78 g, quant.).

[Example 109] Synthesis of 7-butyl-4,7-dimethyl-octahydro-2H-chromen-2-one (Exemplary Compound Bu-5)

The reaction was performed under a nitrogen atmosphere. To a 50 mL reactor, ethyl-3-(4-butyl-2-((t-butyldimethylsilyl)oxy)-4-methylcyclohexyl)butanoate (1.58 g, 3.96 mmol) obtained in Example 108 and a tetrabutylammonium fluoride/THF solution (1 mol/L, 24 mL, 6.0 eq.) were added, and the mixture was stirred at 50° C. for 24 hours. The obtained solution was washed with a saturated saline solution, and then, drying was performed with anhydrous magnesium sulfate and filtration and concentration were performed. The obtained residue was purified with column chromatography, thereby obtaining the desired Exemplary Compound Bu-5 (57 mg, 6% yield).

Exemplary Compound Bu-5

$^1$H-NMR (500 MHz, CDCl$_3$): 0.84-0.96 (6H, m), 1.03 (3H, d, J=7.2 Hz), 1.11-1.61 (10H, m), 1.86-1.93 (1H, m), 2.09 (1H, sep, J=3.5 Hz), 2.40 (2H, dt, J=17.5, 3.5 Hz), 2.69 (2H, dd, J=17.6, 6.6 Hz), 4.31 (1H, td, J=11.2, 4.4 Hz) (major)

$^1$H-NMR (500 MHz, CDCl$_3$): δ 0.84-0.96 (6H, m), 1.02 (3H, d, J=7.1 Hz), 1.11-1.61 (10H, m), 1.96-2.03 (1H, m), 2.09 (1H, sep, J=3.5 Hz), 2.40 (2H, dt, J=17.5, 3.5 Hz), 2.69 (2H, dd, J=17.6, 6.6 Hz), 4.26 (1H, td, J=11.3, 4.2 Hz) (minor)

$^{13}$C-NMR (125 MHz, CDCl$_3$): 14.1 (CH3), 15.1 (CH3), 22.5 (CH3), 23.5 (CH2), 23.8 (CH2), 25.4 (CH2), 28.9 (CH), 34.6 (C), 36.8 (CH2), 39.0 (CH2), 43.0 (CH), 43.5 (CH2), 45.5 (CH2), 75.8 (CH), 171.7 (C) (major)

$^{13}$C-NMR (125 MHz, CDCl$_3$): 14.1 (CH3), 15.1 (CH3), 23.5 (CH2), 23.6 (CH2), 25.7 (CH2), 28.9 (CH), 29.2 (CH3), 34.4 (C), 36.2 (CH2), 37.1 (CH2), 39.0 (CH2), 42.6 (CH), 43.2 (CH2), 75.3 (CH), 171.8 (C) (minor)

Fragrance note: Floral, Fruity, Lactone

[Example 110] Fragrance Composition

A flavor or fragrance composition for perfume was prepared by using Exemplary Compound Bu-1/Bu-1aa/Pr-1a or iBu-1a, which was synthesized above, or nectaryl compound or γ-decalactone compound instead of the exemplary compounds, in accordance with the prescription in the following Table 2.

The sensory evaluation was performed by four professional panelists who have worked for at least 5 years. As a result, all panelists determined that all of the floral green note flavor or fragrance compositions containing the exemplary compounds had a strong floral green aroma whose superiority was clearly recognized, high palatability, and an excellent odor quality, compared with a floral green note flavor or fragrance composition containing a nectaryl compound or a γ-decalactone compound.

TABLE 2

| Components | Blending amount (g) |
| --- | --- |
| Amber accord | 0.50 |
| Ambrettolide | 0.50 |
| Benzyl acetate | 5.00 |
| Benzyl salicylate | 3.00 |
| L-dihydrofarnesal | 1.00 |
| Dipropylene glycol | 6.00 |
| Ethyl linalool | 3.00 |
| FLOROL (registered trademark) 966458 (manufactured by Firmenich S.A.) | 9.50 |
| Galaxolide | 7.50 |
| HEDIONE (registered trademark) (manufactured by Firmenich S.A.) | 20.00 |
| HELIOBOUQUET (registered trademark) (manufactured by Takasago International Corporation) | 2.50 |
| Cis-3-hexenyl salicylate | 1.00 |
| Hexylcinnamic aldehyde | 6.00 |
| JASMODIONE (registered trademark) (manufactured by Takasago International Corporation) | 3.00 |
| Laurinal | 2.50 |
| Linalool | 6.00 |
| Exemplary Compound Bn-1/Exemplary Compound Bu-1aa/Exemplary Compound Pr-1a/Exemplary Compound iBu-1a/nectaryl/γ-decalactone | 1.00 |
| ORBITONE (registered trademark) (manufactured by Takasago International Corporation) | 6.00 |
| Polysantol | 0.50 |
| Rose base | 12.00 |
| White flower accord | 3.50 |
| Total amount | 100.00 |

[Example 111] Fragrance Composition

A flavor or fragrance composition for perfume was prepared by using Exemplary Compound Bu-1/Bu-1aa/Pr-1a or iBu-1a, which was synthesized above, in accordance with the prescription in the following Table 3.

The sensory evaluation was performed by four professional panelists who have worked for at least 5 years. As a result, all the four panelists determined that all of the orange flower note flavor or fragrance compositions containing the exemplary compounds had high palatability and an excellent odor quality.

TABLE 3

| Components | Blending amount (g) |
| --- | --- |
| Benzyl acetate | 1.50 |
| Cassis base | 1.30 |
| DEXTRAMBER (registered trademark) (manufactured by Takasago International Corporation) | 0.05 |
| L-dihydrofarnesal | 0.40 |
| L-dihydrofarnesol | 0.80 |
| DIMETH BENZ CARB BUTY | 0.50 |
| Dipropylene glycol | 2.50 |
| Ethyl vanillin | 0.20 |
| FLOROL (registered trademark) (manufactured by Firmenich S.A.) | 5.00 |
| Galaxolide | 10.00 |
| Hedione | 15.50 |
| Cis-3-hexenyl salicylate | 0.30 |
| HINDINOL (registered trademark) (manufactured by Takasago International Corporation) | 0.90 |
| JASMODIONE (registered trademark) (manufactured by Takasago International Corporation) | 1.00 |
| Linalool | 8.00 |
| Linalyl acetate | 6.00 |
| γ-methylionone | 1.00 |
| Musk accord | 0.35 |
| Exemplary Compound Bu-1/Bu-1aa/Pr-1a/iBu-1a | 0.50 |
| Orange flower base | 3.40 |
| OR ANGE OIL PERA WHITE BRAZIL NAT EO | 4.50 |
| ORBITONE (registered trademark) (manufactured by Takasago International Corporation) | 9.00 |
| Peony accord | 9.50 |
| PHENOXY ETH ISO BUTY | 9.00 |
| THESARON (registered trademark) (manufactured by Takasago International Corporation) | 1.20 |
| TRIPLAL (registered trademark) (manufactured by IFF) | 0.50 |
| Veltol plus | 0.10 |
| VERDON (manufactured by IFF) | 7.00 |
| Total amount | 100.00 |

[Example 112] Shampoo

A shampoo (100 g) perfumed with 1.0% of the flavor or fragrance composition in the above Example 110 was prepared in accordance with the prescription in the following Table 4. The sensory evaluation of the shampoo was performed by four professional panelists who have worked for at least 5 years. All the four panelists determined that the flavor or fragrance compositions using the exemplary compounds all have high palatability and an excellent odor quality compared with the flavor or fragrance compositions using the comparative compounds.

TABLE 4

| Components | Blending amount (g) |
| --- | --- |
| Sodium polyoxyethylene lauryl ether sulfate | 14.00 |
| Lauric acid amidopropyl betaine | 4.00 |
| Coconut oil fatty acid diethanolamide | 3.00 |
| Cationic cellulose | 0.50 |
| Ethylene glycol distearate | 1.00 |
| Ethyl paraoxybenzoate | 0.25 |
| Citric acid | Proper amount |
| Flavor or fragrance composition in Example 110 | 1.00 |
| Purified water | Remainder |
| Total amount | 100.00 |

[Example 113] Body Shampoo

A body shampoo (100 g) perfumed with the flavor or fragrance composition in the above Example 11 was prepared in accordance with the prescription in the following Table 5. The sensory evaluation of the body shampoo was performed by four professional panelists who have worked for at least 5 years. All the four panelists determined that the body shampoo had a clean marine tone that can be clearly recognized, high palatability, and an excellent odor quality.

TABLE 5

| Components | Blending amount (g) |
| --- | --- |
| Triethanolamine | 9.00 |
| Lauric acid | 6.00 |
| Myristic acid | 9.00 |
| Disodium lauryl polyoxyethylene sulfosuccinate (1E.0.) (42%) | 10.00 |
| Alkyl (C8-16) glucoside | 8.00 |
| Glyceryl laurate | 1.00 |
| 2-hydroxyethyl distearate | 2.50 |
| Coconut oil fatty acid diethanolamide | 3.00 |
| Propylene glycol | 5.00 |
| Dibutyl hydroxytoluene | 0.05 |
| Disodium edetate | 0.10 |
| Ethyl paraoxybenzoate | 0.20 |
| Methyl paraoxybenzoate | 0.10 |
| Flavor or fragrance composition in Example 111 | 0.95 |
| Purified water | 45.10 |
| Total amount | 100.00 |

Although the present invention is described in detail with reference to specific embodiments, it will be apparent to those skilled in the art that various changes and modifications can be made without departing from the spirit and scope of the invention. The present application is based on U.S. provisional application No. 62/656,054 filed on Apr. 11, 2018, the contents of which are incorporated herein by reference.

INDUSTRIAL APPLICABILITY

The compounds in the present invention is useful as a fragrance agent or flavoring agent since the compounds have a strong peach-like or jasmine-like aroma.

The invention claimed is:

1. A lactone compound represented by the following general formula (A):

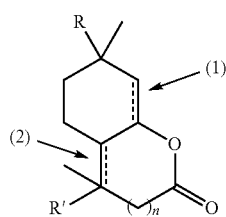

wherein R represents a hydrogen atom or R1;

R1 represents an alkyl group having 2 to 8 carbon atoms which may have substituent(s), an alkenyl group having 2 to 8 carbon atoms which may have substituent(s), an alkynyl group having 2 to 8 carbon atoms which may have substituent(s), or an aryl group;

in the case where R represents a hydrogen atom, R' represents an alkyl group having 2 to 8 carbon atoms which may have substituent(s), an alkenyl group having 2 to 8 carbon atoms which may have substituent(s), an alkynyl group having 2 to 8 carbon atoms which may have substituent(s), or an aryl group, the carbon bond (1) is a single bond or a double bond, and the carbon bond (2) is a single bond;

in the case where R represents R1, R' represents a hydrogen atom or R1, both the carbon bonds (1) and (2) are a single bond, or one of them is a double bond and the other is a single bond; and n is 0 or 1.

2. An ether compound represented by the following general formula (B):

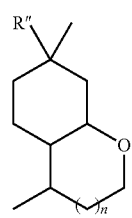

wherein R" represents an alkyl group having 1 to 8 carbon atoms which may have substituent(s), an alkenyl group having 2 to 8 carbon atoms which may have substituent(s), an alkynyl group having 2 to 8 carbon atoms which may have substituent(s), or an aryl group; and n is 0 or 1.

3. A flavor or fragrance composition comprising the compound according to claim 1.

4. A product comprising the flavor or fragrance composition according to claim 3, the product being a beverage, food, fragrance or cosmetic, toiletry product, air care product, daily necessities and household goods, oral composition, hair care product, skin care product, body care product, detergent for cloth, soft finishing agent for cloth, quasi-drug, or pharmaceutical.

5. A method for improving an aroma of a flavor or fragrance, the method comprising adding the compound according to claim 1 to a flavor or fragrance.

6. A flavor or fragrance composition comprising the compound according to claim 2.

7. A product comprising the flavor or fragrance composition according to claim 6, the product being a beverage, food, fragrance or cosmetic, toiletry product, air care product, daily necessities and household goods, oral composition, hair care product, skin care product, body care product, detergent for cloth, soft finishing agent for cloth, quasi-drug, or pharmaceutical.

8. A method for improving an aroma of a flavor or fragrance, the method comprising adding the compound according to claim 2 to a flavor or fragrance.

* * * * *